(12) United States Patent
Brunner et al.

(10) Patent No.: US 7,348,357 B2
(45) Date of Patent: Mar. 25, 2008

(54) ARYLAMIDES

(75) Inventors: Nina Brunner, Essen (DE); Christoph Freiberg, Wuppertal (DE); Thomas Lampe, Düsseldorf (DE); Peter Nell, Wuppertal (DE); Ben Newton, Bucks (GB); Michael Otteneder, Arlesheim (CH); Josef Pernerstorfer, Hilden (DE); Jens Pohlmann, Basel (CH); Guido Schiffer, Wuppertal (DE); Mitsuyuki Shimada, Nara (JP); Niels Svenstrup, Wuppertal (DE); Rainer Endermann, Wuppertal (DE)

(73) Assignee: Bayer HealthCare AG, Leverkusen (DE)

( * ) Notice: Subject to any disclaimer, the term of this patent is extended or adjusted under 35 U.S.C. 154(b) by 0 days.

(21) Appl. No.: 10/524,080

(22) PCT Filed: Jul. 28, 2003

(86) PCT No.: PCT/EP03/08300

§ 371 (c)(1),
(2), (4) Date: Feb. 2, 2006

(87) PCT Pub. No.: WO2004/020432

PCT Pub. Date: Mar. 11, 2004

(65) Prior Publication Data

US 2006/0173040 A1 Aug. 3, 2006

(30) Foreign Application Priority Data

Aug. 8, 2002 (DE) ................ 102 36 340

(51) Int. Cl.
*A61K 31/4015* (2006.01)
*C07D 207/12* (2006.01)
(52) U.S. Cl. ..................... 514/425; 548/546
(58) Field of Classification Search ........... 548/546; 514/425

See application file for complete search history.

(56) References Cited

FOREIGN PATENT DOCUMENTS

EP 0250115 12/1987

OTHER PUBLICATIONS

Needham, et al. Andrimid and Moiramides A-C, Metabolites Produced in Culture by a Marine Isolate of the Bacterium *Pseudomonas fluorescens*: Structure Elucidation and Biosynthesis, J. Org. Chem., 59: 2058-2063 (1994).

*Primary Examiner*—Rebecca Anderson
*Assistant Examiner*—Michael P. Barker

(57) ABSTRACT

The present invention relates to compounds, to processes for preparing them, to pharmaceutical compositions comprising them, and to their use in the therapy and/or prophylaxis of diseases in people or animals, especially diseases of bacterial infection.

18 Claims, No Drawings

ARYLAMIDES

The present invention relates to compounds, to processes for preparing them, to pharmaceutical compositions comprising them, and to their use in the therapy and/or prophylaxis of diseases in people or animals, especially diseases of bacterial infection.

The natural substances moiramide B ($R^a$=hydrogen, $R^b$=methyl) and andrimid ($R^a$=hydrogen, $R^b$=propenyl) have been described as having antibacterial activity, whereas moiramide C ($R^a$=hydroxyl, $R^b$=propenyl) is inactive. (A. Fredenhagen, S. Y. Tamura, P. T. M. Kenny, H. Komura, Y. Naya, K. Nakanishi, *J. Am. Chem. Soc.*, 1987, 109, 4409-4411; J. Needham, M. T. Kelly, M. Ishige, R. J. Andersen, *J. Org. Chem.*, 1994, 59, 2058-2063; M. P. Singh, M. J. Mroczenski-Wildey, D. A. Steinberg, R. J. Andersen, W. M. Maiese, M. Greenstein, *J. Antibiot.*, 1997, 50(3), 270-273). The isolation and antibacterial activity of andrimid is also desccribed in EP-A-250 115. JP 01301657 describes the use of andrimid and certain amide-type derivatives as agrochemical antibiotics.

The synthesis of andrimid is described in A. V. Rama Rao, A. K. Singh, Ch. V. N. S. Varaprasad, *Tetrahedron Letters*, 1991, 32, 4393-4396, that of moiramide B and andrimid in S. G. Davies, D. J. Dixon, *J. Chem. Soc., Perkin Trans. 1*, 1998, 2635-2643.

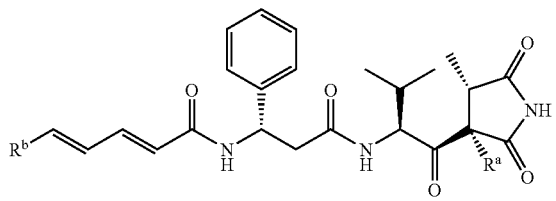

Although antibacterial products with different structures are on the market, a regular possibility is the development of resistance. New products for improved and effective therapy are therefore desirable.

It is an object of the present invention, therefore, to provide new and alternative compounds having equal or improved antibacterial action for treating bacterial diseases in people and animals.

Surprisingly it has been found that derivatives of this class of compound in which the beta-phenylalanine amide group is replaced by a heteroaromatic or substituted aromatic amide have antibacterial activity.

The present invention provides compounds of the formula

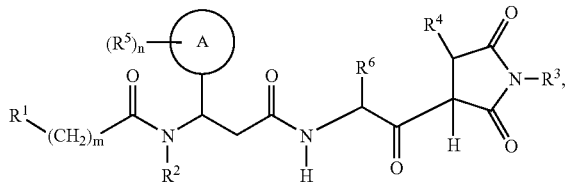

(I)

in which $R^1$ is heteroaryl,
where heteroaryl can be substituted by 0, 1, 2 or 3 substituents $R^{1-1}$, the substituents $R^{1-1}$ being selected independently of one another from the group consisting of halogen, alkyl, nitro, amino, alkylamino, cyano, trifluoromethyl, cycloalkyl, heterocyclyl, aryl, heteroaryl, hydroxyl, alkoxy, aryloxy, benzyloxy, carboxyl, alkoxycarbonyl, aminocarbonyl, alkylcarbonylamino, alkylaminocarbonyl and aminosulfonyl, or $R^1$ is aryl,
where aryl is substituted by 1, 2 or 3 substituents $R^{1-2}$, the substituents $R^{1-2}$ being selected independently of one another from the group consisting of halogen, alkyl, nitro, amino, alkylamino, cyano, trifluoromethyl, cycloalkyl, heterocyclyl, aryl, heteroaryl, hydroxyl, alkoxy, aryloxy, benzyloxy, carboxyl, alkoxycarbonyl, aminocarbonyl, alkylcarbonylamino, arylcarbonylamino, alkylaminocarbonyl and aminosulfonyl, or two substituents $R^{1-2}$, together with the carbon atoms to which they are attached, form a cycloalkyl or heterocyclyl which can be substituted by 0, 1 or 2 substituents $R^{1-2-1}$, the substituents $R^{1-2-1}$ being selected independently of one another from the group consisting of halogen, nitro, amino, trifluoromethyl, hydroxyl, alkyl and alkoxy, $R^2$ is hydrogen or methyl, $R^3$ is hydrogen, hydroxyl, amino, $C_1$-$C_3$ alkyl, benzyl, $C_1$-$C_3$ alkoxy, benzyloxy, $C_1$-$C_3$ alkylamino, $C_1$-$C_3$ alkylcarbonylamino, phenylcarbonylamino or benzylcarbonylamino, $R^4$ is hydrogen or $C_1$-$C_3$ alkyl, $R^5$ is halogen, trifluoromethyl, trifluoromethoxy, nitro, amino, alkylamino, hydroxyl, alkyl, alkoxy, carboxyl, alkoxycarbonyl, aminocarbonyl, alkylaminocarbonyl, aryl or heteroaryl, or two substituents $R^5$ together with the carbon atoms to which they are attached form a cycloalkyl or heterocyclyl each of which may be substituted by 0, 1 or 2 substituents $R^{5-1}$, the substituents $R^{5-1}$ being selected independently of one another from the group consisting of halogen, nitro, amino, trifluoromethyl, hydroxyl, alkyl and alkoxy, $R^6$ is alkyl, cycloalkyl, cycloalkenyl or heterocyclyl, it being possible for $R^6$ to be substituted by 0, 1 or 2 substituents $R^{6-1}$, the substituents $R^{6-1}$ being selected independently of one another from the group consisting of halogen, nitro, amino, trifluoromethyl, hydroxyl, alkyl and alkoxy, n is a number 0, 1, 2 or 3,
it being possible for the radicals $R^5$ to be identical or different when n is 2 or 3, m is a number 0, 1, 2, 3 or 4, A is aryl or heteroaryl, and their salts, their solvates and the solvates of their salts.

Compounds of the invention are the compounds of the formula (I) and their salts, solvates and solvates of the salts, the compounds of the formula (Ia), mentioned below, that are embraced by formula (I), and their salts, solvates and solvates of the salts, and also the compounds embraced by formula (D) and (Ia) and referred to below as implementation example(s), and their salts, solvates and solvates of the salts, where the compounds referred to below and embraced by formula (I) and/or (Ia) are not already salts, solvates and solvates of the salts.

Depending on their structure the compounds of the invention may exist in stereoisomeric forms (enantiomers, diastereomers). The invention therefore relates to the enantiomers or diastereomers and their respective mixtures. From such mixtures of enantiomers and/or diastereomers it is possible to isolate the stereoisomerically uniform constituents in a known way.

The invention relates also, depending on the structure of the compounds, to tautomers of the compounds.

Salts preferred in the context of the invention are physiologically acceptable salts of the compounds of the invention.

Physiologically acceptable salts of the compounds (I) embrace acid addition salts of mineral acids, carboxylic acids and sulfonic acids, e.g., salts of hydrochloric acid, hydrobromic acid, sulfuric acid, phosphoric acid, methanesulfonic acid, ethanesulfonic acid, toluenesulfonic acid, benzenesulfonic acid, naphthalenedisulfonic acid, acetic acid, propionic acid, lactic acid, tartaric acid, malic acid, citric acid, fumaric acid, maleic acid and benzoic acid.

Physiologically acceptable salts of the compounds (I) also embrace salts of customary bases, such as, by way of example and preferably, alkali metal salts (e.g., sodium and potassium salts), alkaline earth metal salts (e.g. calcium and magnesium salts) and ammonium salts derived from ammonia or organic amines having 1 to 16 carbon atoms, such as, by way of example and preferably, ethylamine, diethylamine, triethylamine, ethyldiisopropylamine, monoethanolamine, diethanolamine, triethanolamine, dicyclo-hexylamine, dimethylaminoethanol, procaine, dibenzylamine, n-methylmorpholine, dihydroabietylamine, arginine, lysine, ethylenediamine and methylpiperidin.

Solvates in the context of the invention are those forms of the compounds which in the solid or liquid state form a complex by coordination with solvent molecules. Hydrates are one specific form of the solvates, in which the coordination is with water.

In the context of the present invention the signification of the substituents, unless specified otherwise, is as follows Alkyl per se and "alk" and "alkyl" in alkoxy, alkylamino, alkylaminocarbonyl, alkylcarbonylamino and alkoxycarbonyl are a linear or branched alkyl radical having generally 1 to 8, preferably 1 to 6, more preferably 1 to 4, very preferably 1 to 3 carbon atoms, by way of example and preferably methyl, ethyl, n-propyl, isopropyl, tert-butyl, n-pentyl and n-hexyl.

Alkoxy is by way of example and preferably methoxy, ethoxy, n-propoxy, isopropoxy, tert-butoxy, n-pentoxy and n-hexoxy.

Alkylamino is an alkylamino radical having one or two alkyl substituents (chosen independently of one another), the alkyl substituents independently of one another having generally 1 to 6, preferably 1 to 4, more preferably 1 to 3 carbon atoms, by way of example and preferably methylamino, ethylamino, n-propylamino, isopropylamino, tert-butylamino, n-pentylamino, n-hexylamino, N,N-dimethylamino, N,N-diethylamino, N-ethyl-N-methylamino, N-methyl-N-n-propylamino, N-isopropyl-N-n-propylamino, N-t-butyl-N-methylamino, N-ethyl-N-n-pentylamino and N-n-hexyl-N-methylamino. Thus $C_1$-$C_3$ alkylamino is for example a monoalkylamino radical having 1 to 3 carbon atoms or a dialkylamino radical having 1 to 3 carbon atoms in each alkyl substituent.

Alkylaminocarbonyl is an alkylaminocarbonyl radical having one or two alkyl substituents (chosen independently of one another), the alkyl substituents independently of one another having generally 1 to 6, preferably 1 to 4, more preferably 1 to 3 carbon atoms, by way of example and preferably methylaminocarbonyl, ethylaminocarbonyl, n-propylaminocarbonyl, isopropylaminocarbonyl, tert-butylaminocarbonyl, n-pentylaminocarbonyl, n-hexylaminocarbonyl, N,N-dimethylaminocarbonyl, N,N-diethylaminocarbonyl, N-ethyl-N-methylaminocarbonyl, N-methyl-N-n-propylaminocarbonyl, N-isopropyl-N-n-propylaminocarbonyl, N-t-butyl-N-methylaminocarbonyl, N-ethyl-N-n-pentylaminocarbonyl and N-n-hexyl-N-methylaminocarbonyl. $C_1$-$C_3$ alkylaminocarbonyl is for example a monoalkylaminocarbonyl radical having 1 to 3 carbon atoms or a dialkylaminocarbonyl radical having 1 to 3 carbon atoms in each alkyl substituent.

Alkylcarbonylamino is by way of example and preferably methylcarbonylamino, ethylcarbonylamino, n-propylcarbonylamino, isopropylcarbonylamino, tert-butylcarbonylamino, n-pentylcarbonylamino and n-hexylcarbonylamino.

Alkoxycarbonyl is by way of example and preferably methoxycarbonyl, ethoxycarbonyl, n-propoxycarbonyl, isopropoxycarbonyl, tert-butoxycarbonyl, n-pentoxycarbonyl and n-hexoxycarbonyl.

Cycloalkyl is a cycloalkyl group having generally 3 to 8, preferably 5 to 7 carbon atoms; specified by way of example and preferably for cycloalkyl are cyclopropyl, cyclobutyl, cyclopentyl, cyclohexyl and cycloheptyl. In the case of a cycloalkyl formed by two aryl substituents together with the aryl carbon atoms to which they are attached, two carbon atoms of the cycloalkyl group are $sp^2$ hybridized.

Cycloalkenyl is a cycloalkyl group having generally 3 to 8, preferably 5 to 7 carbon atoms; specified by way of example and preferably for cycloalkenyl are cyclopropenyl, cyclobutenyl, cyclopentenyl, cyclohexenyl and cycloheptenyl.

Aryl is a mono- to tricyclic aromatic radical having generally 6 to 14 carbon atoms; specified by way of example and preferably for aryl are phenyl, naphthyl and phenanthrenyl.

Aryloxy is a mono- to tricyclic aromatic radical, attached via an oxygen atom, and having generally 6 to 14 carbon atoms, by way of example and preferably phenoxy, naphthyloxy and phenanthrenyloxy.

Arylcarbonylamino is by way of example and preferably phenylcarbonylamino, naphthylcarbonylamino and phenanthrenylcarbonylamino.

Heteroaryl is an aromatic, mono- or bicyclic radical having generally 5 to 10, preferably 5 to 6 ring atoms and up to 5, preferably up to 4, heteroatoms from the series S, O and N; by way of example and preferably thienyl, furyl, pyrrolyl, thiazolyl, oxazolyl, oxadiazolyl, pyrazolyl, imidazolyl, pyridyl, pyrimidyl, pyridazinyl, pyrazinyl, indolyl, indazolyl, benzofuranyl, benzothiophenyl, quinolinyl, isoquinolinyl.

Heterocyclyl is a mono- or polycyclic, preferably mono- or bicyclic, heterocyclic radical having generally 4 to 10, preferably 5 to 8 ring atoms and up to 3, preferably up to 2, heteroatoms and/or hetero-groups from the series N, O, S, SO, $SO_2$. The heterocyclyl radicals may be saturated or partly unsaturated. Preference is given to 5-to 8-membered, monocyclic saturated heterocyclyl radicals having up to two heteroatoms from the series O, N and S, such as, by way of example and preferably, tetrahydrofuran-2-yl, tetrahydrothienyl, pyrrolidin-2-yl, pyrrolidin-3-yl, pyrrolinyl, pyranyl, piperidin-1-yl, piperidin-2-yl, piperidin-3-yl, piperidin-4-yl, thiopyranyl, morpholin-1-yl, morpholin-2-yl, morpholin-3-yl, perhydroazepinyl, piperazin-1-yl, piperazin-2-yl.

Halogen is fluorine, chlorine, bromine and iodine, preferably fluorine and chlorine.

If radicals in the compounds of the invention are substituted, the radicals, unless specified otherwise, may be substituted by one or more identical or different substituents. Substitution by up to three identical or different substituents is preferred. Very particular preference is given to substitution by one substituent.

Preference is given in the context of the present invention to compounds of the formula

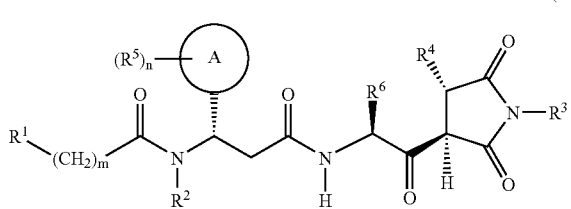

(Ia)

in which $R^1$ to $R^6$, A, m and n are as defined for formula (I), and their salts, their solvates and the solvates of their salts.

Preference is given in the context of the present invention to compounds of the invention in which $R^1$ is 5-, 6-, 9- or 10-membered heteroaryl,
  where $R^1$ can be substituted by 0, 1 or 2 substituents $R^{1-1}$, the substituents $R^{1-1}$ being selected independently of one another from the group consisting of halogen, alkyl, amino, alkylamino, cyano, trifluoromethyl, aryl, heteroaryl, alkoxy, alkoxycarbonyl and aminocarbonyl, or $R^1$ is phenyl or naphthyl,
  where phenyl or naphthyl are substituted by 1, 2 or 3 substituents $R^{1-2}$, the substituents $R^{1-2}$ being selected independently of one another from the group consisting of halogen, alkyl, nitro, amino; alkylamino, cyano, trifluoromethyl, cycloalkyl, heterocyclyl, aryl, heteroaryl, alkoxy, aryloxy, benzyloxy,
alkoxycarbonyl, aminocarbonyl, alkylcarbonylamino, arylcarbonylamino, alkylaminocarbonyl and aminosulfonyl, or two substituents $R^{1-2}$, together with the carbon atoms to which they are attached, form a 5- or 6-membered cycloalkyl or a 5- or 6-membered heterocyclyl, $R^2$ is hydrogen,
$R^3$ is hydrogen, hydroxyl, amino, methyl, benzyl, $C_1$-$C_3$ alkoxy, benzyloxy or $C_1$-$C_3$ alkylamino,
$R^4$ is methyl,
$R^5$ is fluoro, chloro, trifluoromethyl, trifluoromethoxy, nitro, amino, alkylamino, hydroxyl, alkoxy, aminocarbonyl, alkoxycarbonyl, alkyl, phenyl or 5- or 6-membered heteroaryl, or two substituents $R^5$, together with the carbon atoms to which they are attached, form a 5- or 6-membered cycloalkyl or 5- or 6-membered heterocyclyl,
$R^6$ is $C_2$-$C_7$ alkyl or 3- to 7-membered cycloalkyl,
  where $R^6$ can be substituted by 0, 1 or 2 substituents $R^{6-1}$, the substituents $R^{6-1}$ being selected independently of one another from the group consisting of halogen, alkoxy, alkyl and trifluoromethyl,
n is a number 0, 1 or 2,
  where, if n is 2, the radicals $R^5$ can be identical or different,
m is a number 0, 1, 2 or 3, and A is phenyl, naphthyl or 5-, 6-, 9- or 10-membered heteroaryl.

Preference in the context of the present invention is also given to compounds of the invention in which $R^1$ is pyridyl, imidazolyl, thienyl, furyl, oxadiazolyl, pyrazolyl, pyrazinyl, pyridazinyl, pyrimidinyl, quinolinyl or isoquinolinyl,
  where $R^1$ can be substituted by 0, 1 or 2 substituents $R^{1-1}$, the substituents $R^{1-1}$ being selected independently of one another from the group consisting of halogen, alkyl, amino, trifluoromethyl, phenyl and alkoxy, or $R^1$ is phenyl or naphthyl,
  where phenyl or naphthyl are substituted by 1, 2 or 3 substituents $R^{1-2}$, the substituents $R^{1-2}$ being selected independently of one another from the group consisting of halogen, $C_1$-$C_4$ alkyl, dimethylamino, cyano, trifluoromethyl, 3- to 7-membered cycloalkyl, 5- or 6-membered heterocyclyl, phenyl, 5- or 6-membered heteroaryl, $C_1$-$C_3$ alkoxy, phenyloxy, benzyloxy, phenylcarbonylamino and aminosulfonyl, or two substituents $R^{1-2}$, together with the carbon atoms to which they are attached, form a 1,3-benzodioxole or a 1,4-benzodioxane,
$R^2$ is hydrogen,
$R^3$ is hydrogen, amino, methyl, methoxy, ethoxy, methylamino or dimethylamino,
$R^4$ is methyl,
$R^5$ is fluoro, chloro, trifluoromethyl, $C_1$-$C_4$ alkoxy, methoxycarbonyl, $C_1$-$C_4$ alkyl, phenyl or pyridyl, or two substituents $R^5$, together with the phenyl ring to which they are attached, form a 1,3-benzodioxole or a 1,4-benzodioxane,
$R^6$ is $C_3$-$C_6$ alkyl or 3- to 6-membered cycloalkyl,
n is a number 0, 1 or 2,
  and, if n is 2, the radicals $R^5$ can be identical or different,
m is a number 0, 1, 2 or 3, and A is phenyl, naphthyl, pyridyl, thienyl, furanyl, quinolinyl or isoquinolinyl.

Preference in the context of the present invention is also given to compounds of the invention in which $R^1$ is pyridyl, thienyl, furyl, quinolinyl or isoquinolinyl,
  where $R^1$ can be substituted by 0, 1 or 2 substituents $R^{1-1}$, the substituents $R^{1-1}$ being selected independently of one another from the group consisting of halogen, $C_1$-$C_4$ alkyl, trifluoromethyl, phenyl and $C_1$-$C_3$-alkoxy, or $R^1$ is phenyl or naphthyl,
  where phenyl or naphthyl are substituted by 1, 2 or 3 substituents $R^{1-2}$, the substituents $R^{1-2}$ being selected independently of one another from the group consisting of halogen, $C_1$-$C_4$ alkyl, dimethylamino, cyano, trifluoromethyl, 5- or 6-membered heterocyclyl, 5- or 6-membered heteroaryl, $C_1$-$C_3$ alkoxy, phenyloxy or benzyloxy, or two substituents $R^{1-2}$, together with the carbon atoms to which they are attached, form a 1,3-benzodioxole or a 1,4-benzodioxane,
$R^2$ is hydrogen,
$R^3$ is hydrogen, amino, methylamino or dimethylamino,
$R^4$ is methyl, $R^5$ is fluoro, chloro, trifluoromethyl, $C_1$-$C_3$ alkoxy, $C_1$-$C_4$ alkyl, phenyl or pyridyl, $R^6$ is isopropyl, tert-butyl, isopentyl, cyclopentyl or cyclohexyl, n is a number 0, 1 or 2, and, if n is 2, the radicals $R^5$ can be identical or different, m is a number 0, 1 or 2, and A is phenyl, naphthyl, pyridyl, thienyl, quinolinyl or isoquinolinyl.

Preference in the context of the present invention is also given to compounds of the invention in which $R^1$ is pyridyl, thienyl, furyl, quinolinyl or isoquinolinyl, where $R^1$ can be substituted by 0, 1 or 2 substituents $R^{1-1}$, the substituents $R^{1-1}$ being selected independently of one another from the group consisting of fluoro, chloro, trifluoromethyl, $C_1$-$C_4$ alkyl, phenyl and methoxy.

Preference in the context of the present invention is also given to compounds of the invention in which $R^1$ is phenyl or naphthyl,
where phenyl or naphthyl are substituted by 1, 2 or 3 substituents $R^{1-2}$, the substituents $R^{1-2}$ being selected independently of one another from the group consisting of halogen, $C_1$-$C_4$ alkyl, dimethylamino, cyano, trifluoromethyl, 5-or 6-membered heterocyclyl, 5- or 6-membered heteroaryl, $C_1$-$C_3$ alkoxy, phenyloxy or benzyloxy, or two substituents $R^{1-2}$, together with the carbon atoms to which they are attached, form a 1,3-benzodioxole or a 1,4-benzodioxane.

Preference in the context of the present invention is also given to compounds of the invention in which $R^2$ is hydrogen.

Preference in the context of the present invention is also given to compounds of the invention in which $R^3$ is hydrogen or amino.

Preference in the context of the present invention is also given to compounds of the invention in which $R^4$ is methyl.

Preference in the context of the present invention is also given to compounds of the invention in which n is the number zero.

Preference in the context of the present invention is also given to compounds of the invention in which n is the number 1, A is phenyl and $R^5$ is fluoro, chloro, trifluoromethyl, alkoxy, $C_1$-$C_4$ alkyl, phenyl or pyridyl, $R^5$ being positioned meta or para to the linkage site of the phenyl ring. By the linkage site of the phenyl ring is meant the carbon atom of the phenyl ring carrying $R^5$ to which the phenyl ring carrying $R^5$, in accordance with formula (I) or (Ia) as A, is attached to the remainder of the compound.

Preference in the context of the present invention is also given to compounds of the invention in which $R^6$ is $C_3$-$C_6$ alkyl or 3- to 6-membered cycloalkyl, especially isopropyl, isobutyl, 1-methylpropyl or cyclopentyl, very particularly isopropyl or cyclopentyl.

Preference in the context of the present invention is also given to compounds of the invention in which m is the number zero.

Preference in the context of the present invention is also given to compounds of the invention in which A is phenyl, naphthyl, pyridyl, thienyl, quinolinyl or isoquinolinyl.

Preference in the context of the present invention is also given to compounds of the invention in which A is phenyl.

Preference in the context of the present invention is also given to the following compounds:

6-fluoro-N-{(1S)-3-[((1S)-2-methyl-1-{[(3R,4S)-4-methyl-2,5-dioxo-3-pyrrolidinyl]-carbonyl}propyl)amino]-3-oxo-1-phenylpropyl}-2-pyridinecarboxamide N-{(1S)-3-[((1S)-2-methyl-1-{[(3R,4S)-4-methyl-2,5-dioxo-3-pyrrolidinyl]carbonyl}-propyl)amino]-3-oxo-1-phenylpropyl}-3-quinolinecarboxamide N-{(1S)-3-[((1S)-2-methyl-1-{[(3R,4S)$_4$-methyl-2,5-dioxo-3-pyrrolidinyl]-carbonyl}propyl)amino]-3-oxo-1-phenylpropyl}4-phenyl-2-pyridinecarboxamide N-[(1S)-3-({(1S)-1-cyclohexyl-2-[(3R,4S)-4-methyl-2,5-dioxo-3-pyrrolidinyl]-2-oxoethyl}amino)-3-oxo-1-phenylpropyl]-6-fluoro-2-pyridinecarboxamide N-[(1S)-3-({1-cyclopentyl-2-[(3R,4S)$_4$-methyl-2,5-dioxo-3-pyrrolidinyl]-2-oxoethyl}amino)-3-oxo-1-phenylpropyl]-2-pyridinecarboxamide (3S)-N-((1S)-2-methyl--{[(3R,4S)$_4$-methyl-2,5-dioxo-3-pyrrolidinyl]-carbonyl}propyl)-3-phenyl-3-[(2-thienylacetyl)amino]propanamide N-[(1S)-3-({(1S)-1-cyclopentyl-2-[(3R,4)$_4$-methyl-2,5-dioxo-3-pyrrolidinyl]-2-oxoethyl}amino)-3-oxo-1-phenylpropyl]-4-phenyl-2-pyridinecarboxamide N-[(1S)-3-({(1S)-1-cyclopentyl-2-[(3R,4)-4-methyl-2,5-dioxo-3-pyrrolidinyl]-2-oxoethyl}amino)-3-oxo-1-phenylpropyl]-3-quinolinecarboxamide N-[(1S)-3-({(1S)-1-cyclopentyl-2-[(3R,4S)$_4$-methyl-2,5-dioxo-3-pyrrolidinyl]-2-oxoethyl}amino)-3-oxo-1-phenylpropyl]-5-fluoro-1H-indole-2-carboxamide The invention further provides a process for preparing compounds of the formula (I), where

[A] compounds of the formula

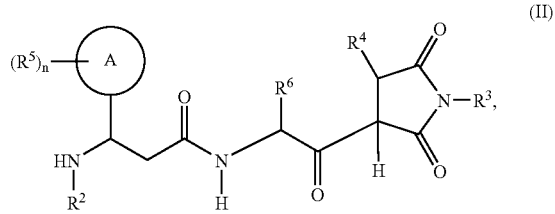

(II)

in which $R^2$ to $R^6$, A and n are as defined above, are reacted with compounds of the formula

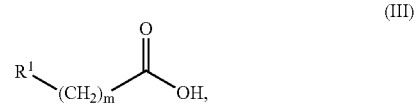

(III)

in which $R^1$ and m are as defined above, it being possible for these to be in activated form if desired, or

[B] compounds of the formula

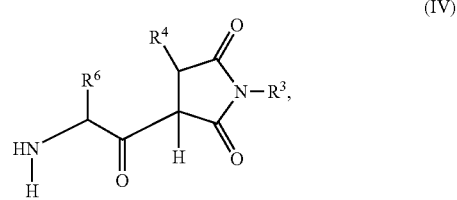

(IV)

in which $R^3$, $R^4$ and $R^6$ are as defined above, are reacted with compounds of the formula

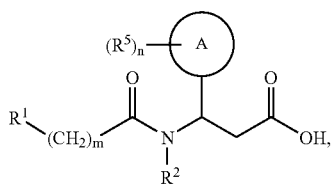

(V)

in which $R^1$, $R^2$, $R^5$, A, m and n are as defined above, it being possible for these to be in activated form if desired.

Suitable for converting the compounds into the activated form in the abovementioned processes are, for example, carbodiimides such as N,N'-diethyl-, N,N,'-dipropyl-, N,N'-diisopropyl-, N,N'-dicyclohexylcarbodiimide, N-(3-dimethylaminoisopropyl)-N'-ethylcarbodiimide hydrochloride (EDC) (optionally in the presence of pentafluorophenol (PFP)), N-cyclohexylcarbodiimide-N'-propyloxymethyl-polystyrene (PS-carbodiimide) or carbonyl compounds such as carbonyldiimidazole, or 1,2-oxazolium compounds such as 2-ethyl-5-phenyl-1,2-oxazolium-3-sulfate or 2-tert-butyl-5-methyl-isoxazolium perchlorate, or acylamino compounds such as 2-ethoxy-1-ethoxycarbonyl-1,2-dihydroquinoline, or propanephosphonic anhydride, or isobutyl chloroformate, or bis(2-oxo-3-oxazolidinyl)phosphoryl chloride or benzotriazolyloxytri(dimethylamino)phosphonium hexafluorophosphate, or O-(benzotriazol-1-yl)-N,N,N',N'-tetramethyluronium hexafluorophosphate (HBTU), 2-(2-oxo-1-(2H)-pyridyl)-1,1,3,3-tetramethyluronium tetrafluoroborate (TPTU) or O-(7-azabenzotriazol-1-yl)-N,N,N',N'-tetramethyl-uronium hexafluorophosphate (HATU), or 1-hydroxybenzotriazole (HOBt), or benzotriazol-1-yloxytris(dimethylamino)phosphonium hexafluorophosphate (BOP), or mixtures of these with bases.

Bases are, for example, alkali metal carbonates, such as sodium or potassium carbonate, or hydrogencarbonate, or organic bases such as trialkylamines, e.g. triethylamine, N-methylmorpholine, N-methylpiperidine, 4-dimethylaminopyridine or diisopropylethylamine.

Preference is given to using HATU with diisopropylethylamine and using EDC with HOBt and triethylamine.

Suitable solvents in this context include inert organic solvents which do not change under the reaction conditions. These include halogenated hydrocarbons such as dichloromethane or trichloromethane, hydrocarbon such as benzene, xylene, toluene, hexane, cyclohexane, or petroleum fractions, nitromethane, dimethylformamide or acetonitrile or ethers such as diethyl ether, tetrahydrofuran or dioxane. It is also possible to use mixtures of the solvents. Particular preference is given to dichloromethane or a mixture of dichloromethane and dimethylformamide.

Process [A]

The compounds of the formula (II) are known or can be prepared by admixing compounds of the formula

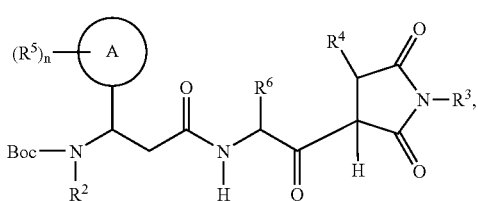

(VI)

in which $R^2$ to $R^6$, A and n are as defined above, with acid, in particular with hydrochloric acid or trifluoroacetic acid. The compounds of the formula (II) are in this case obtained in the form of the corresponding salts, e.g., in the form of their hydrochlorides, and can be used further in this form or converted by chromatographic purification into their salt-free form.

Suitable solvents in this context include inert organic solvents which do not change under the reaction conditions. These include halogenated hydrocarbons such as dichloromethane or trichloromethane, hydrocarbons such as benzene, xylene, toluene, hexane, cyclohexane, or petroleum fractions, nitromethane, dimethylformamide or acetonitrile or ethers such as diethyl ether, tetrahydrofuran or dioxane. It is also possible to use mixtures of the solvents. Particular preference is given to the use of hydrochloric acid in dioxane or trifluoroacetic acid in dichloromethane.

The compounds of the formula (VI) are known or can be prepared by reacting compounds of the formula (IV) with compounds of the formula

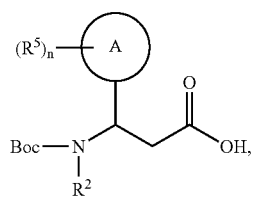

(VII)

in which $R^2$, $R^5$, A and n are as defined above, it being possible for these to be in activated form if desired.

Suitable for converting the compounds into the activated form are, for example, carbodiimides such as N,N'-diethyl-, N,N,'-dipropyl-, N,N'-diisopropyl-, N,N'-dicyclohexylcarbodiimide, N-(3-dimethylaminoisopropyl)-N'-ethylcarbodiimide hydrochloride (EDC) (optionally in the presence of pentafluorophenol (PFP)), N-cyclohexylcarbodiimide-N'-propyloxymethyl-polystyrene (PS-carbodiimide) or carbonyl compounds such as carbonyldiimidazole, or 1,2-oxazolium compounds such as 2-ethyl-5-phenyl-1,2-oxazolium-3-sulfate or 2-tert-butyl-5-methylisoxazolium perchlorate, or acylamino compounds such as 2-ethoxy-1-ethoxycarbonyl-1,2-dihydroquinoline, or propanephosphonic anhydride, or isobutyl chloroformate, or bis(2-oxo-3-oxazolidinyl) phosphoryl chloride or benzotriazolyloxytri(dimethylamino)phosphonium hexafluorophosphate, or O-(benzotriazol-1-yl)-N,N,N',N'-tetramethyluronium hexafluorophosphate (HBTU), 2-(2-oxo-1-(2H)-pyridyl)-1, 1,3,3-tetramethyluronium tetrafluoroborate (TPTU) or O-(7-azabenzotriazol-1-yl)-N,N,N',N'-tetramethyl-uronium hexafluorophosphate (HATU), or 1-hydroxybenzotriazole (HOBt), or benzotriazol-1-yloxytris(dimethylamino)phosphonium hexafluorophosphate (BOP), or mixtures of these with bases.

Bases are, for example, alkali metal carbonates, such as sodium or potassium carbonate, or hydrogencarbonate, or organic bases such as trialkylamines, e.g. triethylamine, N-methylmorpholine, N-methylpiperidine, 4-dimethylaminopyridine or diisopropylethylamine.

Preference is given to using HATU and diisopropylethylamine or EDC with HOBt and triethylamine.

Suitable solvents in this context include inert organic solvents which do not change under the reaction conditions. These include halogenated hydrocarbons such as dichloromethane or trichloromethane, hydrocarbon such as benzene, xylene, toluene, hexane, cyclohexane, or petroleum fractions, nitromethane, dimethylformamide or acetonitrile or ethers such as diethyl ether, tetrahydrofuran or dioxane. It is also possible to use mixtures of the solvents. Particular preference is given to a mixture of dichloromethane and dimethylformamide.

The compounds of the formula (IV) are known from the literature or new and can be prepared by admixing compounds of the formula

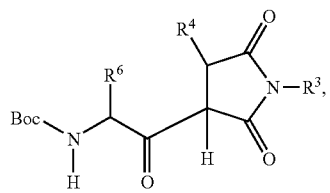

(VIII)

in which $R^3$, $R^4$ and $R^6$ are as defined above, with acid, in particular with hydrochloric acid or trifluoroacetic acid.

Suitable solvents in this context include inert organic solvents which do not change under the reaction conditions. These include halogenated hydrocarbons such as dichloromethane or trichloromethane, hydrocarbons such as benzene, xylene, toluene, hexane, cyclohexane, or petroleum fractions, nitromethane, dimethylformamide or acetonitrile or ethers such as diethyl ether, tetrahydrofuran or dioxane. It is also possible to use mixtures of the solvents. Particular preference is given to the use of hydrochloric acid in dioxane or trifluoroacetic acid in dichloromethane.

The compounds of the formula (VII) are known or can be prepared by procedures known from the literature. (With regard to the preparation of aromatic beta-amino acids see for example: S. Rault, P. Dallemagne, M. Robba, *Bull. Soc. Chim. Fr.*, 1987, 1079-1083; S. G. Davies et al., *J. Chem. Soc., Chem. Commun.* 1993, 1153-1155; V. A. Soloshonok et al., *Tetrahedron Asymmetry*, 1995, 1601-1610; regarding the reaction to form the tert-butoxycarbonyl-protected compounds see T. W. Greene, P. G. M. Wuts, Protective Groups in Organic Synthesis, 3d Edt. 1999, J. Wiley & Sons, Inc.).

The compounds of the formula (VIII) are known or can be prepared by methods known from the literature. (Cf., e.g., S. G. Davies, D. J. Dixon, *J. Chem. Soc., Perkin Trans. 1*, 1998, 17, 2635-2643; A. V. Rama Rao, A. K. Singh, Ch. V. N. S. Varaprasad, *Tetrahedron Letters*, 1991, 32, 4393-4396).

The compounds of the formula (III) are known or can be prepared by methods known from the literature (Houben-Weyl, Methoden der organischen Chemie, vol. E5, Carboxylic acids and carboxylic acid derivatives, Thieme Verlag, Stuttgart, 1985).

Process [B]

The compounds of the formula (V) are known from the literature or new and can be prepared by hydrolyzing compounds of the formula

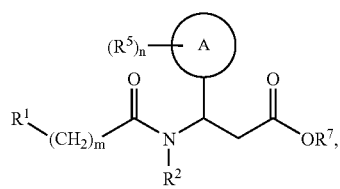

(IX)

in which $R^1$, $R^2$, $R^5$, A, m and n are as defined above and $R^7$ is an alkyl radical.

The hydrolysis can be carried out in accordance with standard methods, e.g., in a mixture of ethanol and water with 40% strength sodium hydroxide solution at room temperature or in a mixture of dioxane and water with 10% strength methanolic potassium hydroxide solution.

The compounds of the formula (IX) are known from the literature or new and can be prepared by reacting compounds of the formula

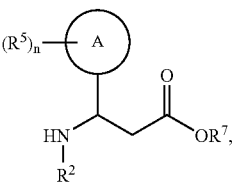

(X)

in which $R^2$, $R^5$, $R^7$, A and n are as defined above, with compounds of the formula (III), it being possible for these to be in activated form if desired.

Suitable for converting the compounds into the activated form in the abovementioned processes are, for example, carbodiimides such as N,N'-diethyl-, N,N,'-dipropyl-, N,N'-diisopropyl-, N,N'-dicyclohexylcarbodiimide, N-(3-dimethylaminoisopropyl)-N'-ethylcarbodiimide hydrochloride (EDC) (optionally in the presence of pentafluorophenol (PFP)), N-cyclohexylcarbodiimide-N'-propyloxymethylpolystyrene (PS-carbodiimide) or carbonyl compounds such as carbonyldiimidazole, or 1,2-oxazolium compounds such as 2-ethyl-5-phenyl-1,2-oxazolium-3-sulfate or 2-tert-butyl-5-methyl-isoxazolium perchlorate, or acylamino compounds such as 2-ethoxy-1-ethoxycarbonyl-1,2-dihydroquinoline, or propanephosphonic anhydride, or isobutyl chloroformate, or bis(2-oxo-3-oxazolidinyl)phosphoryl chloride or benzotriazolyloxytri(dimethylamino)phosphonium hexafluorophosphate, or O-(benzotriazol-1-yl)-N,N,N',N'-tetramethyluronium hexafluorophosphate (HBTU), 2-(2-oxo-1-(2H)-pyridyl)-1,1,3,3-tetramethyluronium tetrafluoroborate (TPTU) or O-(7-azabenzotriazol-1-yl)-N,N,N',N'-tetramethyl-uronium hexafluorophosphate (HATU), or 1-hydroxybenzotriazole (HOBt), or benzotriazol-1-yloxytris(dimethylamino)phosphonium hexafluorophosphate (BOP), or mixtures of these with bases.

Bases are, for example, alkali metal carbonates, such as sodium or potassium carbonate, or hydrogencarbonate, or organic bases such as trialkylamines, e.g., triethylamine, N-methylmorpholine, N-methylpiperidine, 4-dimethylaminopyridine or diisopropylethylamine.

Preference is given to using HATU with diisopropylethylamine and using EDC with HOBt and triethylamine.

Suitable solvents in this context include inert organic solvents which do not change under the reaction conditions. These include halogenated hydrocarbons such as dichloromethane or trichloromethane, hydrocarbon such as benzene, xylene, toluene, hexane, cyclohexane, or petroleum fractions, nitromethane, dimethylformamide or acetonitrile or ethers such as diethyl ether, tetrahydrofuran or dioxane. It is also possible to use mixtures of the solvents. Particular preference is given to dichloromethane or a mixture of dichloromethane and dimethylformamide.

The compounds of the formula (X) are known from the literature or new and can be prepared in analogy to methods known from the literature (With regard to the preparation of aromatic beta-amino acids and their conversion into the corresponding alkyl esters see for example: S. Rault, P. Dallemagne, M. Robba, *Bull. Soc. Chim. Fr.*, 1987, 1079-1083; S. G. Davies et al., *J. Chem. Soc., Chem. Commun.* 1993, 1153-1155; V. A. Soloshonok et al., *Tetrahedron Asymmetry*, 1995, 1601-1610; S. J. Faulconbridge et al., *Tetrahedron Letters*, 2000, 41, 2679-2682).

Synthesis may also take place on a polymeric support. In that case $R^2$ in the synthesis sequence is a polymer (resin), preference being given to the use of 4-(4-formyl-3-methoxyphenoxy)butyryl-aminomethyl-polystyrene or another resin in which a polymeric backbone such as polystyrene or block copolymers of polystyrene with ethylene glycol has attached to it via a linker group such as 3-methoxyphenoxyethyl, 3,5-dimethoxyphenoxyethoxymethyl or 3-methoxyphenoxybutyrylaminomethyl a formyl radical or another radical which allows amines to be attached to the polymeric support.

The preparation of the compounds of the invention can be illustrated by the following synthesis schemes:

Starting Compounds:

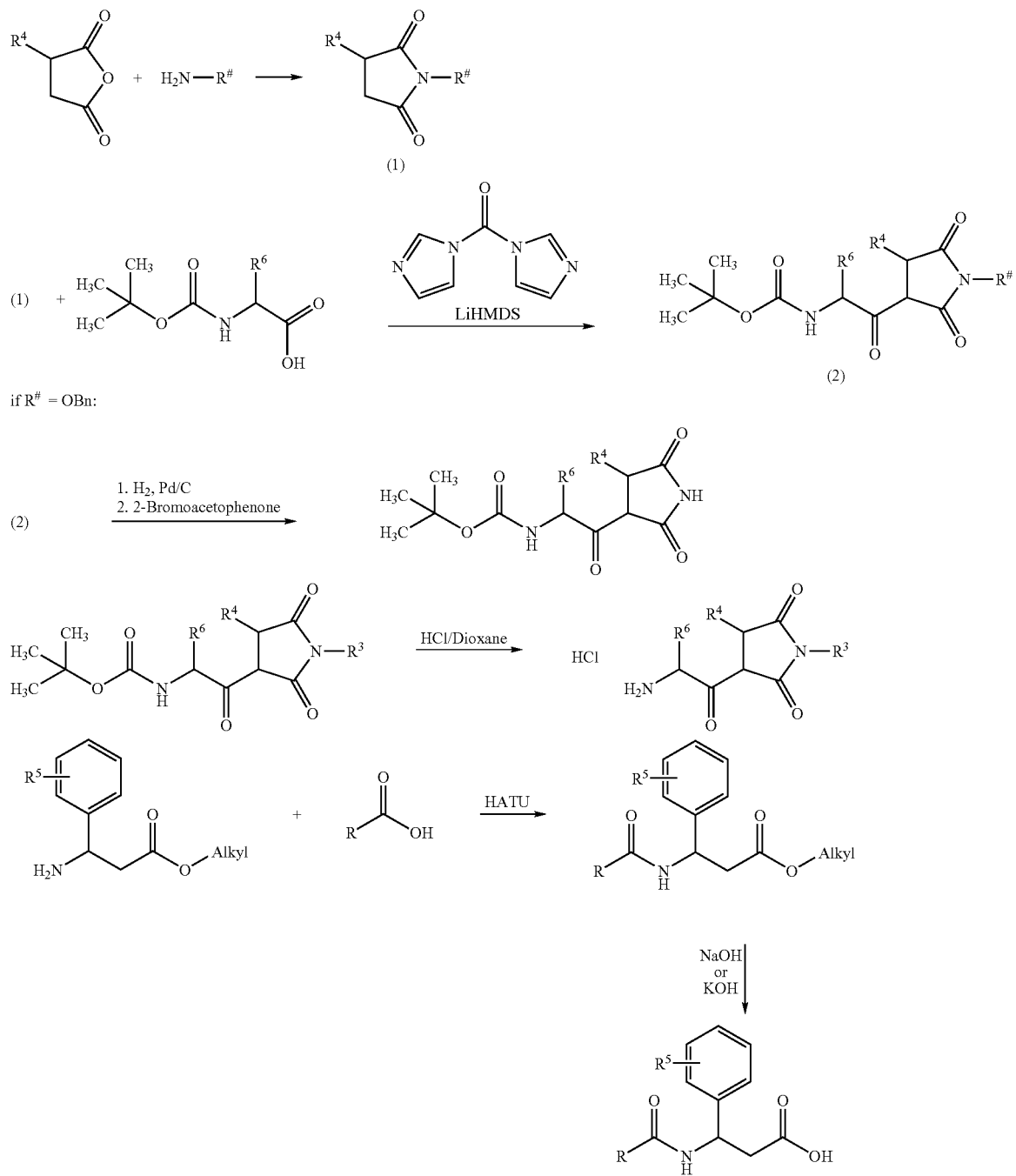

Preparation Examples:

Method A

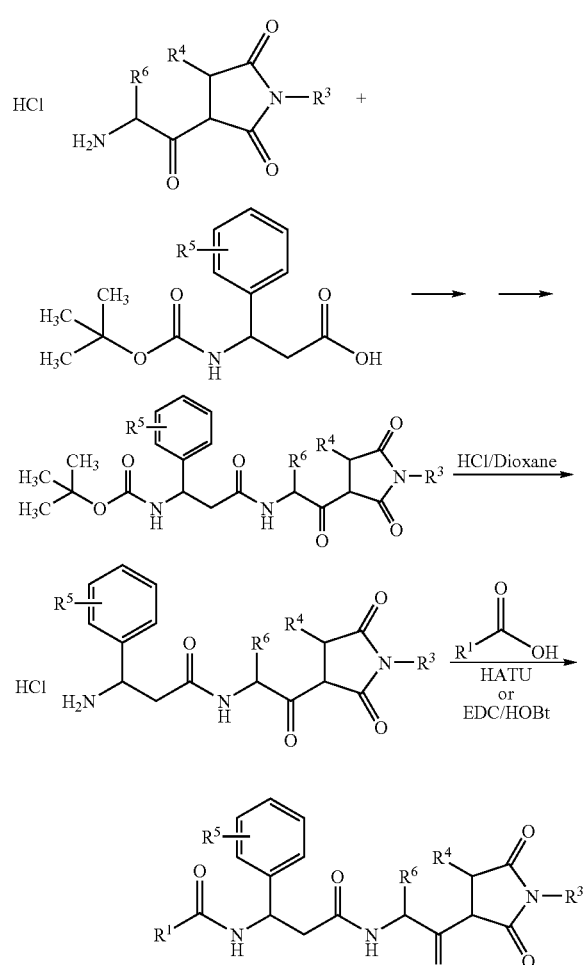

Method B

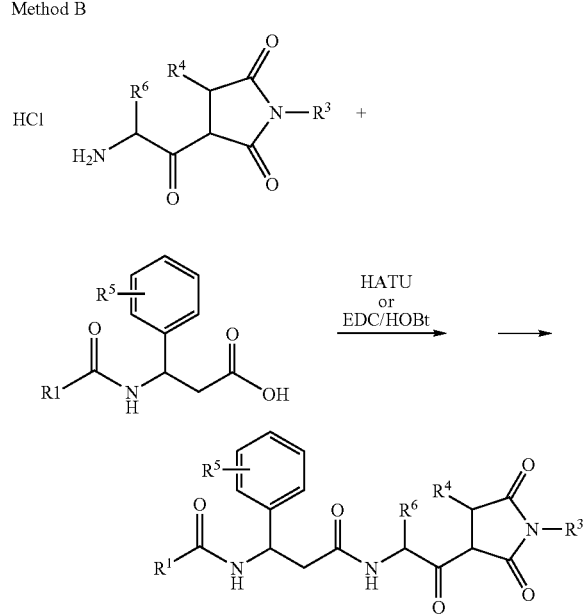

Solid Phase Synthesis:

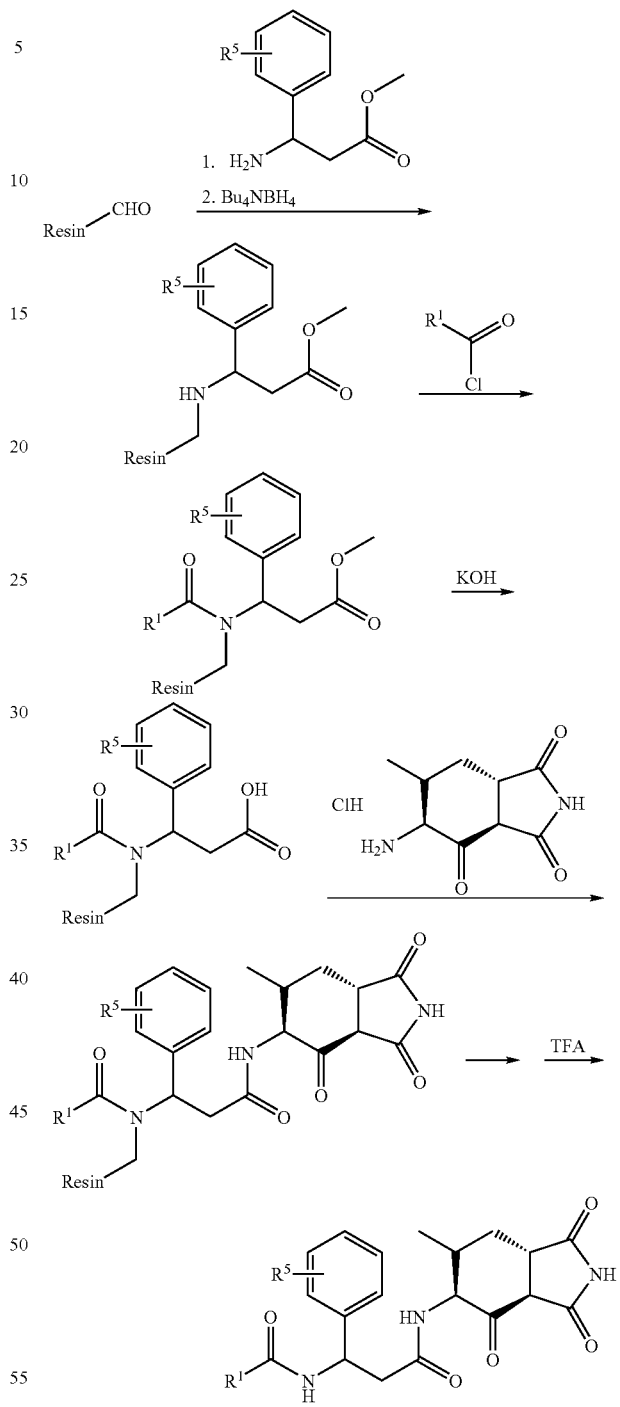

The present invention further provides compounds of the formula I for controlling diseases, particularly bacterial diseases, and also medicinal products comprising compounds of the formula I and auxiliaries, and also for the use of compounds of the formula (I) for producing a medicinal product for treating bacterial diseases.

The formulations of the invention are particularly active against bacteria and bacterialike microorganisms. They are therefore particularly suitable for the prophylaxis and chemotherapy of local and systemic infections in human and veterinary medicine that are induced by these pathogens.

By way of example it is possible to treat and/or prevent local and/or systemic diseases caused by the following pathogens or by combinations of the following pathogens:

Gram-positive cocci, e.g., staphylococci (*Staph. aureus, Staph. epidermidis*), enterococci (*E. faecalis, E. faecius*) and streptococci (*Strept. agalactiae, Strept. pneumoniae*); gram-negative cocci (*Neisseria gonorrhoeae*) and gram-negative rods such as enterobacteria, e.g., *Escherichia coli, Haemophilus influenzae*, citrobacter (*Citrob. freundii, Citrob. divernis*), *salmonella* and *shigella*; and also *klebsiellas* (*Klebs. pneumoniae, Klebs. oxytocy*), enterobacter (*Ent. aerogenes, Ent. agglomerans*), *hafnia, serratia* (*Serr. marcescens*), *providencia, yersinia*, and also the genus *Acinetobacter*. The antibacterial spectrum further embraces strictly anaerobic bacteria such as *Bacteroides fragilis*, representatives of the genus *Peptococcus, Peptostreptococcus* and the genus *Clostridium*; and also mycoplasmas (*M. pneumoniae, M. hominis, M. urealyticum*) and mycobacteria, e.g., *Mycobacterium tuberculosis*.

The above listing of pathogens should be interpreted merely as exemplary and in no way as restrictive. Examples that may be mentioned of diseases which may be caused by the stated pathogens or combination infections and which may be prevented, remedied or cured by the formulations of the invention include the following:

Infectious diseases in humans, such as septic infections, bone and joint infections, skin infections, postoperative wound infections, abscesses, phlegmons, wound infections, infected burns, burn wounds, infections in the oral region, infections following dental operations, septic arthritis, mastitis, tonsillitis, genital infections and eye infections.

As well as in humans, bacterial infections in other species too can be treated. Examples that may be mentioned include the following:

pigs: coli diarrhea, enterotoxemia, sepsis, dysenteria, salmonellosis, metritis-mastitis-agalactia syndrome, mastitis;

ruminants (cattle, sheep, goats): diarrhea, sepsis, bronchopneumonia, salmonellosis, pasteurellosis, mycoplasmosis, genital infections;

horses: bronchopneumonias, joint ill, puerperal and postpartum infections, salmonellosis;

dogs and cats: bronchopneumonia, diarrhea, dermatitis, otitis, urinary tract infections, prostatitis;

poultry (chickens, turkeys, quails, pigeons, ornamental birds and others): mycoplasmosis, *E. coli* infections, chronic respiratory tract diseases, salmonellosis, pasteurellosis, psittacosis.

It is also possible to treat bacterial diseases associated with the breeding and keeping of farmed and ornamental fish, in which case the antibacterial spectrum extends beyond the aforementioned pathogens to embrace further pathogens such as *Pasteurella, Brucella, Campylobacter, Listeria, Erysipelothris, Corynebacteria, Borellia, Treponema, Nocardia, Rickettsi, Yersinia*, for example.

The active ingredient may act systemically and/or locally. For that purpose it can be administered in appropriate manner, such as orally, parenterally, pulmonically, nasally, sublingually, lingually, buccally, rectally, transdermally, conjunctivally, otically or as an implant.

For these administration routes the active ingredient can be administered in suitable administration forms.

Administration forms suitable for oral administration are known such forms which deliver the active ingredient rapidly and/or in a modified way, such as tablets (uncoated and coated tablets, such as film-coated tablets or tablets provided with enteric coatings), capsules, sugar-coated tablets, granules, pellets, powders, emulsions, suspensions and solutions.

Parenteral administration can be made with avoidance of an absorption step (intravenously, intraarterially, intracardially, intraspinally or intralumbarly) or with inclusion of absorption (intramuscularly, subcutaneously, intracutaneously, percutaneously, or intraperitoneally). Administration forms suitable for parenteral administration include preparations for injection and infusion in the form of solutions, suspensions, emulsions, lyophilisates and sterile powders.

Preference is given to parenteral administration, more particularly intravenous administration.

Examples suitable for the other administration routes are pharmaceutical forms for inhalation (including powder inhalers, nebulizers), nasal drops/solutions, sprays; capsules or tablets to be administered lingually, sublingually or buccally, suppositories, ear and eye preparations, vaginal capsules, aqueous suspensions (lotions, shaking mixtures), lipophilic suspensions, ointments, creams, milk, pastes, dusting powders or implants.

The active ingredients can be converted in conventional manner into the stated administration forms. This is done with the use of inert, nontoxic, pharmaceutically appropriate auxiliaries (excipients). These include, among others, carriers (e.g., microcrystalline cellulose), solvents (e.g. liquid polyethylene glycols), emulsifiers (e.g., sodium dodecyl sulfate), dispersants (e.g., polyvinylpyrrolidone), synthetic and natural biopolymers (e.g., albumen), stabilizers (e.g., antioxidants such as ascorbic acid), colorants (e.g., inorganic pigments such as iron oxides) or flavor and/or odor masking agents.

It has generally proven advantageous in the case of parenteral administration to administer amounts of about 5 to 250 mg/kg body weight per 24 hours in order to achieve effective results. In the case of oral administration the amount is about 5 to 100 mg/kg body weight per 24 hours.

It may nevertheless be necessary, where appropriate, to deviate from the amounts specified, specifically as a function of body weight, administration route, individual response to the active ingredient, type of formulation, and time or interval at which administration takes place.

The percentages in the tests and examples below, unless stated otherwise, are percentages by weight; parts are parts by weight. Solvent ratios, dilution ratios and concentration figures for liquid/liquid solutions are based in each case on the volume.

A. EXAMPLES

Reaction schemes which are shown for general procedures show a selection of examples, but can be employed in each case for all of the examples which refer to them.

A. Abbreviations:
Boc tert-butoxycarbonyl
$CDCl_3$ deuterochloroform
DCI direct chemical ionization
DIEA N,N-diisopropylethylamine
DMSO dimethyl sulfoxide EDC N-(3-dimethylaminoisopropyl)-N'-ethylcarbodiimide hydrochloride
eq. equivalent
ES electrospray ionization (for MS)
Fmoc fluorenylmethoxycarbonyl
HATU O-(7-azabenzotriazol-1-yl)-N,N,N',N'-tetramethyluronium hexafluorophosphate
h hour
HOBt 1-hydroxylbenzotriazole
HPLC high-pressure, high-performance liquid chromatography
LC-MS liquid chromatography-coupled mass spectroscopy
MS mass spectroscopy
MW molecular weight [g/mol]
NMR nuclear magnetic resonance spectroscopy
PS-DIEA N,N-diisopropylethylamine-polystyrene (Resin)
$R_f$ retention index (for TLC)
RP-HPLC reverse phase HPLC
RT room temperature
$R_t$ retention time (for HPLC)
THF tetrahydrofuran HPLC and LC-MS Methods:

Method 1: column: Kromasil C18, L-R temperature: 30° C., flow rate=0.75 ml min$^{-1}$, mobile phase: A=0.01 M HClO$_4$, B=acetonitrile, gradient: →0.5 min 98% A→4.5 min 10% A→6.5 min 10% A.

Method 2: column: Kromasil C18 60*2 mm, L-R temperature: 30° C., flow rate=0.75 ml min$^{-1}$, mobile phase: A=0.01 M H$_3$PO$_4$, B=acetonitrile, gradient: →0.5 min 90% A→4.5 min 10% A→6.5 min 10% A.

Method 3: column: Kromasil C18 60*2 mm, L-R temperature: 30° C., flow rate=0.75 ml min$^{-1}$, mobile phase: A=0.005 M HClO$_4$, B=acetonitrile, gradient: →0.5 min 98% A→4.5 min 10% A→6.5 min 10% A.

Method 4: column: Symmetry C18 2.1×150 mm, column oven: 50° C., flow rate=0.6 ml min$^{-1}$, mobile phase: A=0.6 g 30% strength hydrochloric acid/1 water, B=acetonitrile, gradient: 0.0 min 90% A→4.0 min 10% A→9 min 10% A.

Method 5: Instrument: Micromass Quattro LCZ
Column: Symmetry C18, 50 mm×2.1 mm, 3.5 µm, temperature: 40° C., flow rate=0.5 ml min$^{-1}$, mobile phase A=acetonitrile+0.1% formic acid, mobile phase B=water+0.1% formic acid, gradient: 0.0 min 10% A→4 min 90% A→6 min 90% A.

Method 6: Instrument: Micromass Platform LCZ
Column: Symmetry C18, 50 mm×2.1 mm, 3.5 µm, temperature: 40° C., flow rate=0.5 ml min$^{-1}$, mobile phase A=acetonitrile+0.1% formic acid, mobile phase B=water+0.1% formic acid, gradient: 0.0 min 10% A o 4 min 90% A→6 min 90% A.

Method 7: Instrument: Micromass Quattro LCZ
Column: Symmetry C18, 50 mm×2.1 mm, 3.5 µm, temperature: 40° C., flow rate=0.5 ml min$^{-1}$, mobile phase A=acetonitrile+0.1% formic acid, mobile phase B water+0.1% formic acid, gradient: 0.0 min 5% A→1 min 5% A o 5 min 90% A→6 min 90% A.

Method 8: column: Symmetry C18 2.1×150 mm, 5 µm, column oven: 70° C., flow rate=0.9 ml min$^{-1}$, mobile phase: A=acetonitrile, B=0.3 g 30% strength hydrochloric acid/1 water, gradient: 0.0 min 2% A→2.5 min 95% A→5 min 95% A.

Method 9: column: Symmetry C18 3.9×150 mm, column oven: 40° C., flow rate=1.5 ml min$^{-1}$, mobile phase: A=water+0.05% H$_3$PO$_4$, B=acetonitrile, gradient: 0.0 min 10% B→0.6 min 10% B→3.8 min 100% B→5.0 min 100% B.

Method 10: Instrument: Waters Alliance 2790 LC; column: Symmetry C18, 50 mm×2.1 mm, 3.5 µm; mobile phase A: water+0.1% formic acid, mobile phase B: acetonitrile+0.1% formic acid; gradient: 0.0 min 5% B→5.0 min 10% B→6.0 min 10% B; temperature: 50° C., flow rate: 1.0 m/min, UV detection: 210 nm.

Method 11: Instrument type MS: Micromass ZQ; instrument type HPLC: Waters Alliance 2790; column: Symmetry C18, 50 mm×2.1 mm, 3.5 µm; mobile phase B: acetonitrile+0.05% formic acid, mobile phase A: water+0.05% formic acid; gradient: 0.0 min 10% B→3.5 min 90% B→5.5 min 90% B; oven: 50° C., flow rate: 0.8 ml/min, UV detection: 210 nm.

Method 12: Instrument: Waters Alliance 2790 LC; column: Symmetry C18, 50 mm×2.1 mm, 3.5 µm; mobile phase A: water+0.05% formic acid, mobile phase B: acetonitrile+0.05% formic acid; gradient: 0.0 min 5% B→4.5 min 10% B→5.5 min 10% B; temperature: 50° C., flow rate: 1.0 ml/min, UV detection: 210 nm.

Method 13: Instrument: Micromass Quattro LCZ, HP1100; column: Symmetry C18, 50 mm×2.1 mm, 3.5 µm; mobile phase A: water+0.05% formic acid, mobile phase B: acetonitrile+0.05% formic acid; gradient: 0.0 min 90% A→4.0 min 10% A→6.0 min 10% A; Oven: 40° C., flow rate: 0.5 ml/min, UV detection: 208-400 nm.

Method 14: Instrument: Micromass Platform LCZ, HP1100; column: Symmetry C18, 50 mm×2.1 mm, 3.5 µm; mobile phase A: water+0.05% formic acid, mobile phase B: acetonitrile+0.05% formic acid; gradient: 0.0 min 90% A→4.0 min 10% A→6.0 min 10% A; oven: 40° C., flow rate: 0.5 ml/min, UV detection: 208-400 nm.

Method 15: Instrument: Waters Alliance 2790 LC; column: Symmetry C18, 50 mm×2.1 mm, 3.5 µm; mobile phase A: water+0.05% formic acid, mobile phase B: acetonitrile+0.05% formic acid; gradient: 0.0 min 10% B→4.0 min 90% B o 6.0 min 90% B; temperature: 50° C., flow rate: 0.0 min 0.5 ml/min→4.0 min 0.8 ml/min, UV detection: 210 nm.

Method 16: Instrument type MS: Micromass ZQ; intrument type HPLC: Waters Alliance 2790; column: Symmetry C18, 50 mm×2.1 mm, 3.5 µm; mobile phase B: acetonitrile+0.05% formic acid, mobile phase A: water+0.05% formic acid; gradient: 0.0 min 5% B→4.5 min 90% B→5.5 min 90% B; oven: 50° C., flow rate: 1.0 ml/, UV detection: 210 nm.

Method 17: Instrument type MS: Micromass ZQ; instrument type HPLC: Waters Alliance 2790; column: Uptisphere C18, 50 mm×2.0 mm, 3.0 µm; mobile phase B: acetonitrile+0.05% formic acid, mobile phase A: water+0.05% formic acid; gradient: 0.0 min 5% B→2.0 min 40% B→4.5 min 90% B→5.5 min 90% B; oven: 45° C., flow rate: 0.0 min 0.75 ml/min→4.5 min 0.75 ml/min→5.5 min 1.25 ml/min, UV detection: 210 nm.

Method 18: Instrument: Micromass Platform LCZ with HPLC Agilent series 1100; column: Grom-SIL120 ODS-4 HE, 50 mm×2.0 mm, 3 µm; mobile phase A: 1 l water+1 ml 50% strength formic acid, mobile phase B: 1 l acetonitrile+1 ml 50% strength formic acid; gradient: 0.0 min 100% A→0.2 min 100% A→2.9 min 30% A→3.1 min 10% A→4.5 min 10% A; oven: 55° C., flow rate: 0.8 ml/min, UV detection: 208-400 nm.

Method 19: Instrument: Micromass Quattro LCZ, with HPLC Agilent series 1100; column: Grom-SIL120 ODS-4 HE, 50 mm×2.0 mm, 3 μm; mobile phase A: 1 l water+1 ml 50% strength formic acid, mobile phase B: 1 l acetonitrile+1 ml 50% strength formic acid; gradient: 0.0 min 100% A→0.2 min 100% A→2.9 min 30% A→3.1 min 10% A→4.5 min 10% A; oven: 55° C., flow rate: 0.8 ml/min, UV detection: 208-400 nm.

Method 20: Instrument type MS: Micromass ZQ; instrument type HPLC: Waters Alliance 2790; column: Grom-Sil 120 ODS-4 HE 50×2 mm, 3.0 μm; mobile phase B: acetonitrile+0.05% formic acid, mobile phase A: water+0.05% formic acid; gradient: 0.0 min 5% B→2.0 min 40% B→4.5 min 90% B→5.5 min 90% B; oven: 45° C.; flow rate: 0.0 min 0.75 ml/min 4.5 min 0.75 ml/min→5.5 min 1.25 ml/min; UV detection: 210 nm.

Method 21: Instrument type MS: Micromass ZQ; instrument type HPLC: Waters Alliance 2790; column: Grom-Sil 120 ODS-4 HE 50×2 mm, 3.0 μm; mobile phase B: acetonitrile+500 ul 50% strength formic acid/1; mobile phase A: water+500 μl 50% strength formic acid/1; gradient: 0.0 min 0% B+0.2 min 0% B→2.9 min 70% B→3.1 min 90% B→4.5 min 90% B, oven: 50° C., flow rate: 0.8 ml/min; UV detection: 210 nm.

Method 22: Instrument: Micromass Quattro LCZ with HPLC Agilent series 1100; column: UPTISPHERE HDO, 50 mm×2.0 mm, 3 μm; mobile phase A: 1 l water+1 ml 50% strength formic acid, mobile phase B: 1 l acetonitrile+1 ml 50% strength formic acid; gradient: 0.0 min 100% A→0.2 min 100% A→2.9 min 30% A→3.1 min 10% A→4.5 min 10% A; oven: 55° C., flow rate: 0.8 ml/min, UV detection: 208-400 nm.

Starting Compounds:

Example 1A (3S)-1,3-Dimethyl-2,5-pyrrolidinedione

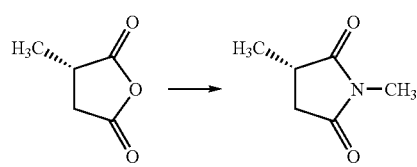

600 mg (5.26 mmol) of (3S)-3-methyldihydro-2,5-furandione (preparation: S. G. Davies, D. J. Dixon, *J. Chem. Soc., Perkin Trans.* 1, 1998, 17, 2635-2643) are introduced to a vessel together with 559 mg (0.77 ml, 5.52 mmol) of triethylamine in 5 ml of dichloromethane at 0° C., and 373 mg (5.52 mmol) of methylamine hydrochloride are added. The reaction mixture is stirred at room temperature overnight and then 938 mg (5.78 mmol) of N,N-carbonyldiimidazole are added in portions. The mixture is stirred at room temperature for 1.5 h and at reflux temperature for 30 minutes. After it has cooled to room temperature the reaction mixture is washed with 5% strength hydrochloric acid and water, the organic phase is dried over magnesium sulfate, filtered and concentrated and the product is dried under a high vacuum. This gives 605 mg of the product (88% of theory).

MS (ES+): m/z (%)=128 (M+H$^+$) (100).

HPLC (method 6): R$_t$=0.81 min.

$^1$H-NMR (300 MHz, CDCl$_3$): δ=3.10 (dd, 1H), 2.99 (s, 3H), 2.90-2.82 (m, 1H), 2.32 (dd, 1H), 1.35 (d, 3 H).

Example 2A (3R,4S)-3-[(2S)-2-(tert-Butoxycarbonyl)amino-3-methylbutanoyl]-1,4-dimethyl-2,5-pyrrolidinedione

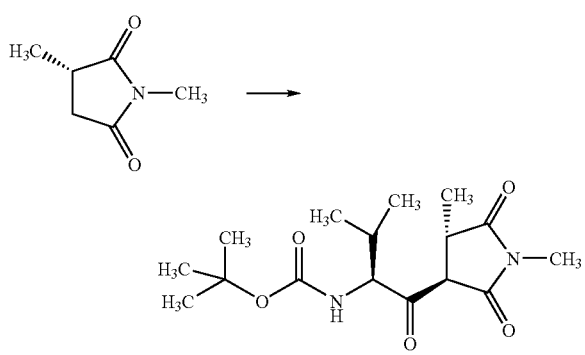

684 mg (3.15 mmol) of N-(tert-butoxycarbonyl)-L-valine and 561 mg (3.46 mmol) of N,N-carbonyldiimidazole are stirred in 4 ml of tetrahydrofuran at room temperature for 2 h. Then 400 mg (3.15 mmol) of (3S)-3-1,3-dimethyl-2,5-pyrrolidinedione are added to this mixture and the whole mixture is added dropwise over the course of 30 minutes to 6.3 ml of a 1 molar solution of lithium hexamethyldisilazide in THF, which has been cooled to −65° C. After the end of the addition stirring is continued at −65° C. for 15 minutes more, and then 6 ml of saturated aqueous ammonium chloride are added. After the reaction mixture has been warmed to room temperature it is diluted with diethyl ether and the organic phase is washed with saturated aqueous sodium chloride solution and subsequently concentrated. The crude product is purified by RP-HPLC (mobile phase: water-acetonitrile, gradient). This gives 223 mg (22% of theory) of the desired product.

MS (ES−): m/z (%)=325 (M−H$^+$) (35).

HPLC (method 5): R$_t$=3.99 min.

$^1$H-NMR (200 MHz, CDCl$_3$): δ=5.70 (br. d, 1H), 4.57 (dd, 1H), 3.78 (d, 1H), 3.47-3.30 (m, 1H), 2.98 (s, 3H), 2.50-2.32 (m, 1H), 1.46 (s, 9H), 1.32 (d, 3H), 1.02 (d, 3H), 0.80 (d, 3H).

In the same way it is possible by reacting the corresponding N-tert-butoxycarbonyl-protected amino acids with (3S)-1-(benzyloxy)-3-methyl-2,5-pyrrolidinedione (preparation: S. G. Davies, D. J. Dixon, *J. Chem. Soc., Perkin Trans.* 1, 1998, 17, 2635-2643) to prepare the following derivatives:

| Example | Structure | MW | MS | HPLC |
|---|---|---|---|---|
| 3A | 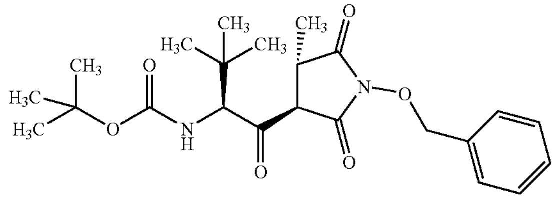 | 432.52 | MS (ES−), m/z (%): 431 (M − H)− (100) | HPLC (method 6): $R_t$ = 4.87 min |
| 4A | 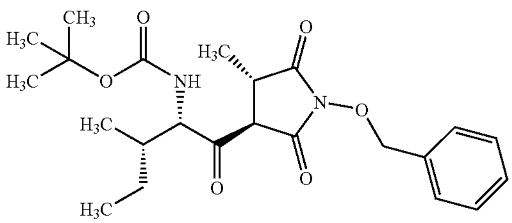 | 432.51 | MS (ES−), m/z (%): 431 (M − H)− (100) | HPLC (method 10): $R_t$ = 4.10 min |
| 5A | 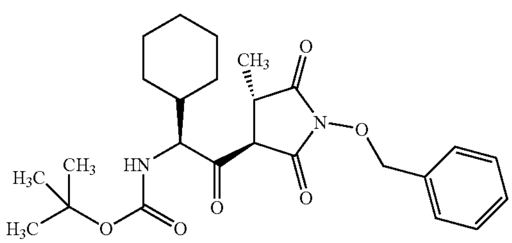 | 458.55 | MS (ES−), m/z (%): 457 (M − H)− (100) | HPLC (method 12): $R_t$ = 4.12 min |
| 6A | 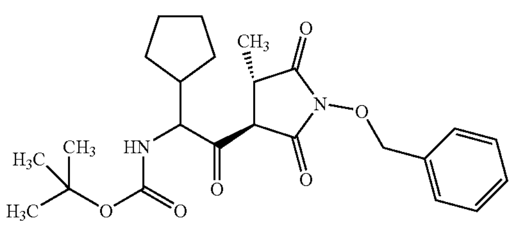 | 444.53 | MS (ES−), m/z (%): 443 (M − H)− (100) | HPLC (method 12): $R_t$ = 3.97 min |

General Instructions A: Reductive deprotection of 1-benzyloxy-2,5-pyrrolidinediones

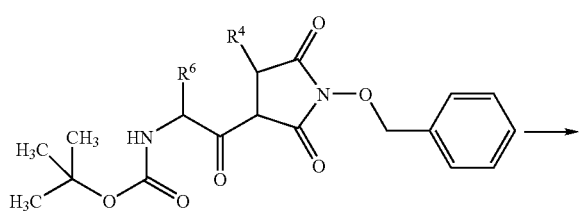

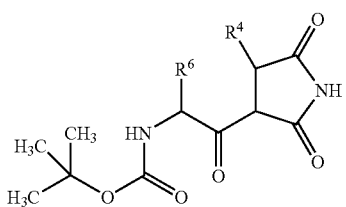

Deprotection takes place in a manner similar to that of S. G. Davies, D. J. Dixon, *J. Chem. Soc., Perkin Trans.* 1, 1998, 17, 2635-2643.

The 1-benzyloxy-2,5-pyrrolidinedione (1 eq.) is dissolved in methanol (about 0.02 mol/l), a catalytic amount of palladium-on-carbon (10%) is added, and the mixture is stirred under a hydrogen atmosphere (atmospheric pressure) for 1 h. The reaction mixture is then filtered and concentrated. The residue is dissolved in acetonitrile (about 0.05 mol/l) and added dropwise at room temperature to a solution of 2-bromoacetophenone (1 eq) in acetonitrile (about 0.03 mol/l) at room temperature. Thereafter over a period of 2 h, 1.5 eq. of triethylamine in acetonitrile (about 0.35 mol/l) are added dropwise to the reaction mixture. The reaction mixture is stirred at room temperature overnight and concentrated and the crude product is purified by means of RP-HPLC (mobile phase: acetonitrile/water+0.3 ml 37% strength hydrochloric acid/l, gradient).

In accordance with general instructions A it is possible to obtain the following compounds:

| Example | Structure | MW | MS | HPLC |
|---|---|---|---|---|
| 7A | 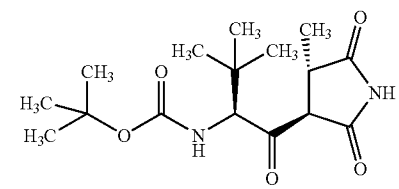 | 326.40 | MS (ES+), m/z (%): 327 (M + H)+ (100) | HPLC (method 5): R$_t$ = 3.87 min |
| 8A | 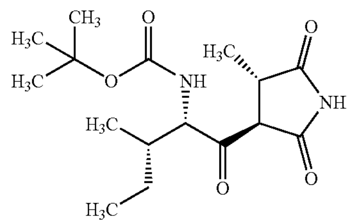 | 326.40 | MS (ES+), m/z (%): 349 (M + Na)+ (100) | HPLC (method 12): R$_t$ = 2.97 min |
| 9A | 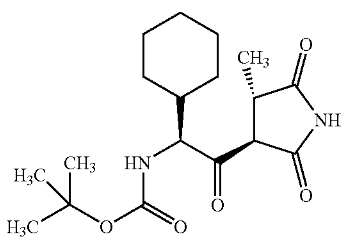 | 352.43 | MS (ES−), m/z (%): 351 (M − H)− (100) | HPLC (method 12): R$_t$ = 3.23 min |
| 10A | 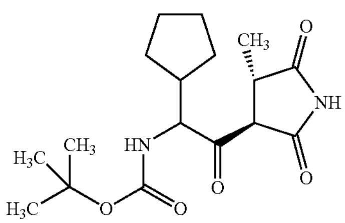 | 338.40 | MS (ES−), m/z (%): 337 (M − H)− (100) | HPLC (method 13): R$_t$ = 4.16 min |

Example 11A (3R,4S)-3-[(2S)-2-Amino-3-methylbutanoyl]-4-methyl-2,5-pyrrolidinedione hydrochloride

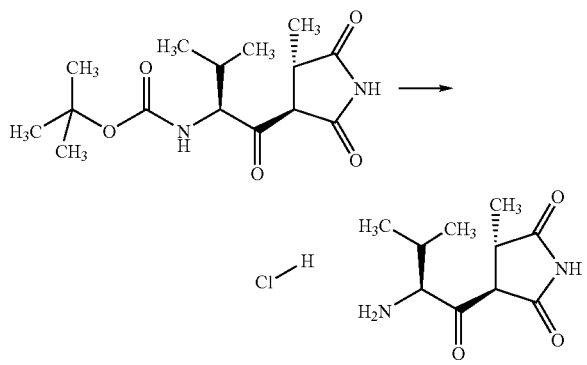

A solution, cooled at 0° C., of 4.40 g (14.09 mmol) of (3R,4S)-3-[(2S)-2-(tert-butoxycarbonyl)amino-3-methylbutanoyl]-4-methyl-2,5-pyrrolidinedione (preparation: S. G. Davies, D. J. Dixon, *J. Chem. Soc., Perkin Trans.* 1, 1998, 17, 2635-2643) in dioxane is admixed dropwise with 35 ml of 4N hydrochloric acid solution in 1,4-dioxane. When the addition is at an end the mixture is warmed to room temperature and stirred for 2 h, after which the mixture is concentrated under reduced pressure. The crude product can be used directly in the next stage. If desired the residue is treated with diethyl ether and the crystals precipitated are filtered off and dried under a high vacuum.

Yield: 2.99 g (86% of theory).

MS (ES+): m/z (%)=213 (M+H+) (100).

HPLC (method 4): R$_t$=0.41 min.

In the same way it is possible, from the corresponding tert-butoxycarbonylamino derivatives, by treatment with hydrochloric acid in dioxane, to prepare the following amines in the form of their hydrochlorides and to react them further directly:

| Example | Structure | MW | MS |
|---|---|---|---|
| 12A | [structure] | 226.28 | MS (ES+), m/z (%): 227 (M + H)+ (80) |
| 13A | [structure] | 226.28 | MS (ES+), m/z (%): 227 (M + H)+ (100) |
| 14A | [structure] | 226.28 | |
| 15A | [structure] | 252.32 | |
| 16A | [structure] | 238.29 | |

General instructions B: Preparation of the beta-amino acid methyl esters

The beta-amino [synthesis according to instructions known from the literature (e.g., S. Rault P. Dallemagne, M. Robba, Bull. Soc. Chim. Fr., 1987, 1079-1083; L. Lázár, T. Martinek, G. Bernáth, F. Fülöp, Synth. Comm., 1998, 28, 219-224)] is 0.5 to 1.0 moil) and admixed dropwise at 0° C. with 1.2 eq. of thionyl chloride. After the end of the addition the reaction mixture is stirred at room temperature overnight and then concentrated. The residue is dissolved in a little methanol and the product is precipitated with diethyl ether. The solid is filtered off with suction, washed repeatedly with diethyl ether and dried under reduced pressure.

Alternatively the workup may take place as follows: following evaporation to dryness, the residue is taken up in water and washed twice with ethyl acetate. The organic phase is discarded and the aqueous phase is neutralized with saturated sodium hydrogen carbonate solution and again extracted three times with ethyl acetate. The organic phases of the final extraction are dried over sodium sulfate or magnesium sulfate, decanted and evaporated to dryness.

In accordance with general instructions B it is possible to obtain the following compounds:

| Example | Structure | MW | MS |
|---|---|---|---|
| 17A | [structure] | 237.25 | MS (ES+), m/z (%): 238 (M + H)+ |
| 18A | [structure] | 223.23 | MS (ES+), m/z (%): 224 (M + H)+ |

Example 19A

Methyl 3-amino-3-(3-chlorophenyl)propionate

Methanol (110 ml) is cooled to −10° C. and slowly admixed with thionyl chloride (12.0 g, 101.2 mmol). 3-Amino-3-(3-chlorophenyl)propionic acid (10.1 g, 50.6 mmol) is added and the mixture is stirred at room temperature overnight. The solution is concentrated to a high extent, under reduced pressure, and partitioned between ethyl acetate (100 ml) and saturated sodium hydrogen carbonate solution (200 ml). The pH of the aqueous phase is above 7. The aqueous phase is again extracted twice with ethyl acetate (100 ml). The combined ethyl acetate phases are dried over sodium sulfate, filtered and concentrated.

Yield: 9.7 g (87%).

$^1$H NMR (300 MHz, CDCl$_3$): δ=7.37 (s, 1 H), 7.30-7.20 (m, 3 H), 4.40 (t, 1 H), 3.68 (s, 3 H), 2.67-2.60 (m, 2H).

Example 20A

Methyl (S)-3-amino-3-phenylpropionate

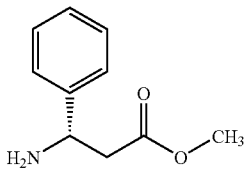

2.3 g (11.65 mmol) of (S)-3-amino-3-phenylpropionic acid are introduced in 100 ml of methanol and admixed with a catalytic amount of concentrated sulfuric acid (0.02 eq.). The reaction mixture is heated at reflux for 24 h and then concentrated. The crude product can be used without further purification in the next stage.

Yield: 2.7 g (65%).

$^1$H NMR (300 MHz, $d_6$-DMSO): δ=8.50 (s, 2 H), 7.52-7.37 (m, 5 H), 4.61 (t, 1 H), 3.58 (s, 3 H), 3.13 (dd, 1 H), 2.98 (dd, 1 H).

MS (ES+): m/z (%)=180 (M+H)$^+$ (100).

General Instructions C: Reaction of 3-amino-3-phenylpropionic acid alkyl esters with carboxylic acids

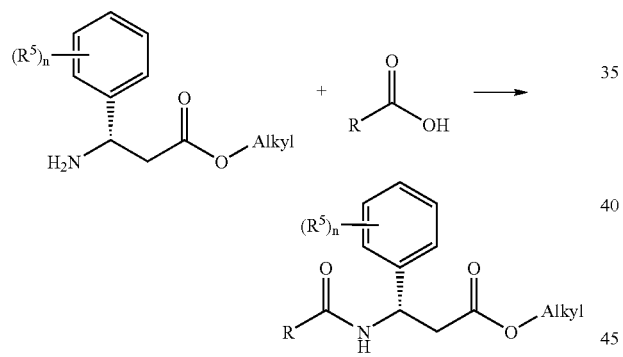

The carboxylic acid (1.3-1.5 eq.) is introduced in dichloromethane (about 0.1 mol/l) at 0° C. and admixed with 1.3-1.5 eq. of HATU. This mixture is admixed first with a solution of the 3-amino-3-phenylpropionic acid alkyl ester (1 eq.) in a 1:1 mixture of dichloromethane and N,N-dimethylformamide (about 0.1 mol/l) and subsequently dropwise, over a period of 1 h, with a solution of diisopropylethylamine (3.5 eq) in a 1:1 mixture of dichloromethane and N,N-dimethylformamide (about 1 mol/l). The mixture is stirred at 0° C. for 30 minutes and then at room temperature overnight. The reaction mixture is then concentrated and purified by means of RP-HPLC (mobile phase: water-acetonitrile, gradient).

Alternatively the reaction may also take place by the following method:

A solution of the 3-aminopropionic acid alkyl ester (1 eq.) in absolute dichloromethane or a mixture (5:1 to 1:1) of absolute dichloromethane and N,N-di-methylformamide (about 0.1 to 0.3 mol/l) is admixed with the carboxylic acid derivative (1.1-1.5 eq.), triethylamine (3 eq.), HOBt (3 eq.) and finally 1.2 eq. of EDC. The reaction mixture is stirred at room temperature (2 h to overnight), before being concentrated under reduced pressure. The residue is taken up in ethyl acetate or dichloromethane and the organic phase is washed with water, saturated sodium hydrogencarbonate solution and saturated sodium chloride solution, dried over sodium sulfate, filtered and concentrated. The product can be purified by chromatography on silica gel (mobile phases: mixtures of cyclohexane/ethyl acetate or mixtures of dichloromethane and ethanol) or by RP-HPLC (mobile phases: variable gradients of water and acetonitrile), or alternatively by a combination of both methods.

Example 21A

Methyl (3S)-3-phenyl-3-[(2-pyridinylcarbonyl)amino]propionate

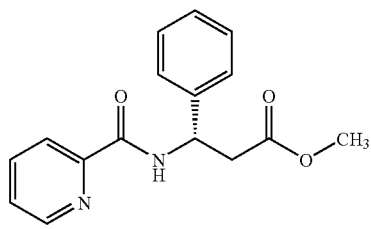

Synthesis in accordance with general instructions C.

$^1$H NMR (300 MHz, $d_6$-DMSO): δ=9.37 (d, 1 H), 8.67 (d, 1 H), 8.05-7.95 (m,2 H), 2 H), 7.66-7.57 (m, 1 H), 7.48-7.19 (m, 5 H), 5.49 (br. q, 1 H), 3.55 (s, 3H), 3.19 (dd, 1H), 2.96 (dd, 1 H).

MS (ES+): m/z (%)=285 (M+H)$^+$ (35).

HPLC (method 5): $R_f$=3.63 min.

Example 22A

Methyl (3S)-3-{[(6-fluoro-2-pyridinyl)carbonyl]amino}-3-phenylpropionate

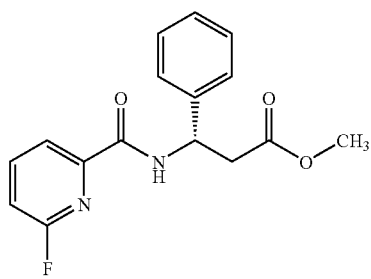

Synthesis in accordance with general instructions C.

$^1$H NMR (300 MHz, $d_6$-DMSO): δ=9.23 (d, 1H), 8.21-8.15 (m, 1H), 7.96-7.92 (m, 1 H), 7.45-7.20 (m, 6H), 5.46 (q, 1H), 3.55 (s, 3H), 3.18 (dd, 1H), 2.96 (dd, 1 H).

MS (ES+): m/z (%)=325 (M+Na)$^+$ (60).

HPLC (method 14): $R_f$=4.35 min.

In accordance with general instructions C it is possible to obtain the following compounds:

| Example | Structure | MW | MS |
|---|---|---|---|
| 23A | 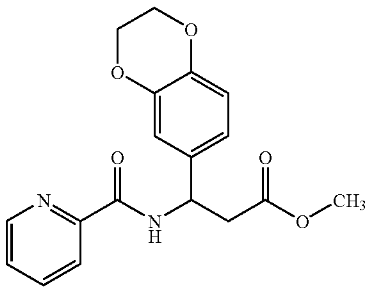 | 342.35 | MS (ES+), m/z (%): 343 (M + H)+ |
| 24A | 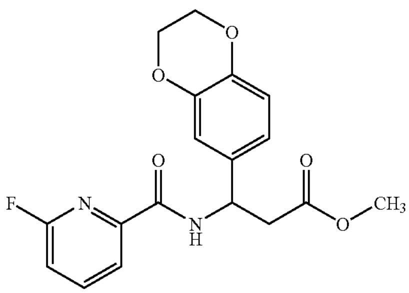 | 360.34 | MS (ES+), m/z (%): 361 (M + H)+ |
| 25A | 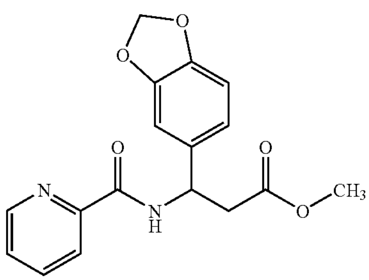 | 328.32 | MS (ES+), m/z (%): 329 (M + H)+ |
| 26A | 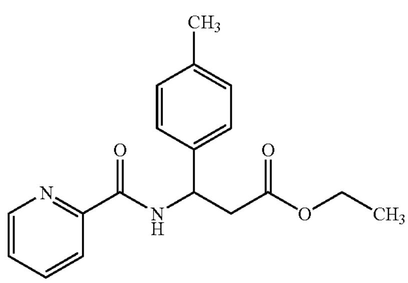 | 312.37 | MS (ES+), m/z (%): 313 (M + H)+ |

General Instructions D: Hydrolysis of the propionic acid alkyl esters

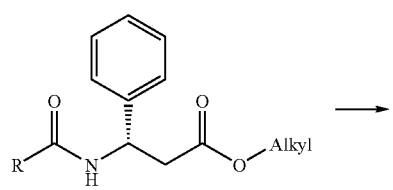

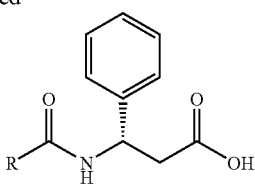

The propionic acid alkyl ester is introduced to a vessel in a 3:1 mixture of ethanol and water (about 0.1-0.15 mol/l) and 5 eq. of 40% strength sodium hydroxide solution are added. The reaction mixture is stirred at room temperature for 24 h, acidified with dilute hydrochloric acid (to a pH of about 3) and concentrated. The residue is taken up in ethyl acetate and washed with saturated aqueous sodium chloride solution. The organic phase is dried over magnesium sulfate, filtered and concentrated. The product obtained can be used without further purification in the next stage.

An alternative option is to use the following method:

The propionic acid alkyl ester is introduced to a vessel in a 1:1 mixture of dioxane and water (about 0.1-0.15 mol/l) and 3 eq. of a solution of potassium hydroxide in methanol (100 mg/ml) are added. The reaction mixture is stirred at room temperature for 2 h and then concentrated. The residue is taken up in water and acidified with dilute hydrochloric acid. The aqueous phase is extracted three times with a 1:1 mixture of dichloromethane and ethyl acetate. The combined organic phases are dried over sodium sulfate, filtered and concentrated. The product obtained can be used without further purification in the next stage.

Example 27A (3S)-3-Phenyl-3-[(2-pyridinylcarbonyl)amino]propionic acid

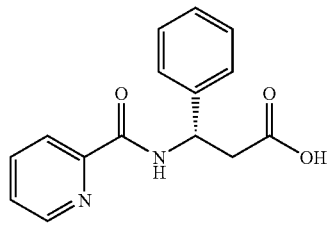

Synthesis in accordance with general instructions D.

$^1$ H NMR (300 MHz, $d_6$-DMSO): δ=12.22 (s, 1 H), 9.30 (d, 1 H), 8.68 (d, 1 H), 8.05-7.95 (m, 2 H), 7.66-7.58 (m, 1 H), 7.46-7.19 (m, 5 H), 5.45 (q, 1 H), 3.04 (dd, 1H), 2.87 (dd, 1 H).

MS (ES-): m/z (%)=269 (M-H)$^-$ (100).

HPLC (method 5): $R_t$=3.12 min.

Example 28A (3S)-3-{[(6-Fluoro-2-pyridinyl)carbonyl]amino}-3-phenylpropionic acid

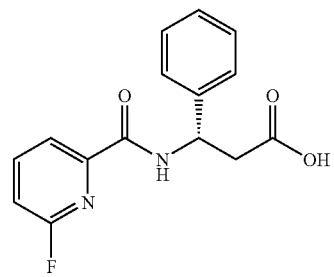

Synthesis in accordance with general instructions D.

MS (ES-): m/z (%)=287 (M-H)$^-$ (100).

HPLC (method 13): $R_t$=3.61 min.

In accordance with general instructions D it is possible to obtain the following compounds:

| Example | Structure | MW | MS | HPLC |
|---|---|---|---|---|
| 29A | 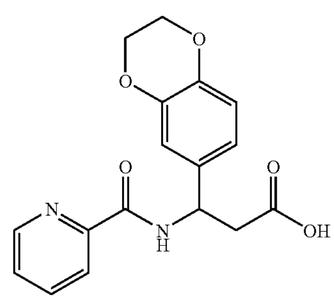 | 328.32 | MS (ES+), m/z (%): 329 (M + H)$^+$ | |
| 30A | 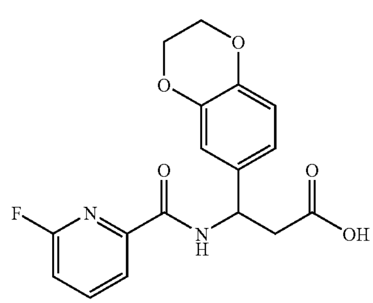 | 346.31 | MS (ES-), m/z (%): 345 (M - H)$^-$ | HPLC (method 9): $R_t$ = 3.69 min |

| Example | Structure | MW | MS | HPLC |
|---|---|---|---|---|
| 31A | 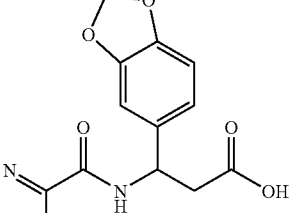 | 314.3 | MS (ES+), m/z (%): 315 (M + H)+ | |
| 32A | 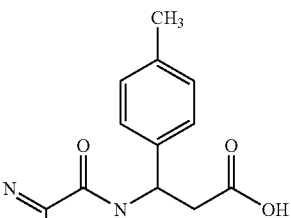 | 284.31 | MS (ES+), m/z (%): 285 (M + H)+ | HPLC (method 9): $R_t$ = 3.82 min |

The propionic acid derivatives obtained in this way can be reacted in accordance with the instructions described below (reaction of 3-[2-aminoalkanoyl]-2,5-pyrrolidinedione hydrochloride derivatives with carboxylic acid derivatives).

General Instructions E: Preparation of N-tert-butoxycarbonyl-protected beta-amino acids The beta-amino acid (1 eq.) [synthesis in accordance with instructions known from the literature (e.g., S. Rault, P. Dallemagne, M. Robba, *Bull. Soc. Chim. Fr.*, 1987, 1079-1083; L. Lázár, T. Martinek, G. Bemath, F. Fülöp, *Synth. Comm.*, 1998, 28, 219-224)] is introduced in water (concentration about 0.3-1 mol/l) and admixed with triethylamine (1.5-3 eq.). Then a solution of 2-(tert-butoxycarbonyloximino)-phenylacetonitrile (1.1 eq.) in dioxane (0.3-1 mol/l) is added. The reaction mixture is stirred at room temperature for 3 h, diluted with water and washed with diethyl ether. The aqueous phase is acidified with 5% strength citric acid (to a pH of about 2) and extracted three times with ethyl acetate. The combined organic phases are washed with saturated sodium chloride solution, dried over sodium sulfate, filtered and concentrated. The crude product can if desired be recrystallized from ethyl acetate/n-hexane.

In accordance with general instructions E it is possible to obtain the following compounds:

| Example | Structure | MW | MS | HPLC |
|---|---|---|---|---|
| 33A | 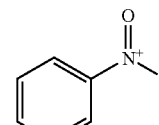 | 310.3 | MS (ES+), m/z (%): 311 (M + H)+ | HPLC (method 8): $R_t$ = 3.87 min |
| 34A | 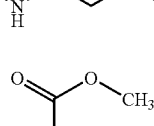 | 323.34 | MS (ES+), m/z (%): 324 (M + H)+ | HPLC (method 8): $R_t$ = 2.39 min |

-continued

| Example | Structure | MW | MS | HPLC |
|---|---|---|---|---|
| 35A | 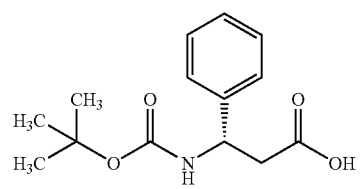 | 323.39 | MS (ES−), m/z (%): 322 (M − H)⁻ | HPLC (method 14): $R_t$ = 4.35 min |

Example 36A (3S)-3-[(tert-Butoxycarbonyl)amino]-3-phenylpropionic acid

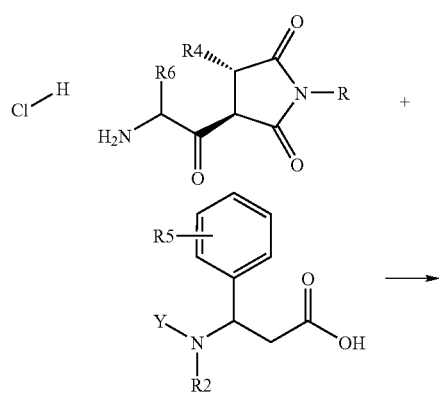

2.82 g (17 mmol) of (S)-3-amino-3-phenylpropionic acid are slurred in 60 ml of dioxane and at 0° C. 4.1 g (18.8 mmol) of di-tert-butyl dicarbonate (Boc anhydride) and 43 ml of a 1N sodium hydroxide solution in water are added to the slurry. The reaction mixture is stirred at 0° C. for 30 minutes and then at room temperature for 3 h. Subsequently the reaction mixture is concentrated and the residue is taken up in methylene chloride. The organic phase is washed with 1N hydrochloric acid and saturated sodium chloride solution, dried over magnesium sulfate and concentrated. The crude product (3.12 g) can be reacted further without additional purification.

MS (ES−): m/z (%)=264 (M−H)⁻ (100).

HPLC (method 14): $R_t$=3.89 min.

General Instructions F: Acylation of 3-[2-aminoalkanoyl]-2,5-pyrrolidinedione hydrochloride derivatives with carboxylic acid derivatives

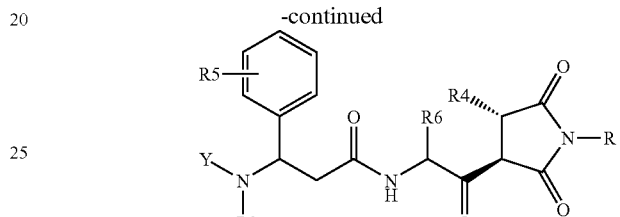

-continued

A solution of carboxylic acid derivative (1.2-1.5 eq.) in absolute dichloromethane or a mixture (5:1 to 1:1) of absolute dichloromethane and N,N-dimethylformamide (about 0.1 to 0.3 mol/l) is admixed at 0° C. first with an equimolar amount of HATU and then with the 3-[2-aminoalkanoyl]-2,5-pyrrolidinedione hydrochloride derivative (1 eq., optionally as a solution in N,N-dimethylformamide or dichloromethane/N,N-dimethylformamide mixtures). Subsequently at 0° C. a solution of 2.5-3.5 eq. of diisopropylethylamine in a 1:1 mixture of absolute dichloromethane and N,N-dimethylformamide (0.2-1 mol/l) is added dropwise over a period of 1 h. After the end of the addition the reaction mixture is stirred at 0° C. for 30 minutes more and then at room temperature overnight, before being concentrated under reduced pressure. The product can be obtained by chromatography on silica gel (mobile phases: mixtures of cyclohexane/ethyl acetate or mixtures of dichloromethane and ethanol) or by RP-HPLC (mobile phases: variable gradients of water and acetonitrile), or alternatively by a combination of both methods.

Alternatively the reaction may also take place by the following method:

A solution of the 3-[2-aminoalkanoyl]-2,5-pyrrolidinedione hydrochloride derivative (1 eq.) in absolute dichloromethane or a mixture (5:1 to 1:1) of absolute dichloromethane and N,N-dimethylformamide (about 0.1 to 0.3 mol/l) is admixed with the carboxylic acid derivative (1.1-1.5 eq.), triethylamine (3 eq.), HOBt (3 eq.) and finally 1.2 eq. of EDC. The reaction mixture is stirred at room temperature (2 h to overnight) before being concentrated under reduced pressure. The residue is taken up in ethyl acetate or dichloromethane and the organic phase is washed with water, saturated sodium hydrogencarbonate solution and saturated sodium chloride solution, dried over sodium sulfate, filtered and concentrated. The product can be purified by chromatography on silica gel (mobile phases: mixtures of cyclohexane/ethyl acetate or mixtures of dichloromethane and ethanol) or by RP-HPLC (mobile phases: variable gradients of water and acetonitrile), or alternatively by a combination of both methods.

Example 37A tert-Butyl ((S)-2-{(S)-2-methyl-1-[1-((3R,4S)-4-methyl-2,5-dioxo-pyrrolidin-3-yl)-methanoyl]-propylcarbamoyl}-1-phenylethyl)carbamate

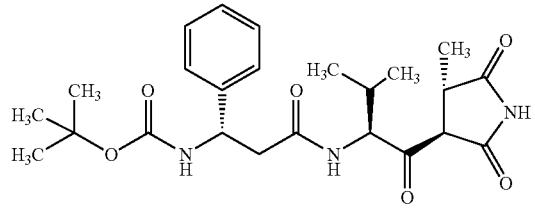

Synthesis in accordance with general instructions F.

$^1$H-NMR (400 MHz, $d_6$-DMSO): δ=11.45 (s, 1H), 7.98 (d, 1H), 7.31-7.24 (m, 5H), 7.20 (br. s, 1 H), 4.88-4.82 (br. s, 1 H), 4.69 (br. s, 1 H), 3.98 (d, 1H), 2.95-2.89 (m, 1H), 2.77-2.69 (m, 1H), 2.51-2.44 (m, 1H), 2.35-2.29 (m, 1H), 1.10 (d, 3 H), 0.85 (d, 3 H), 0.78 (d, 3 H).

MS (ES+): m/z (%)=460 (M+H$^+$) (100).
HPLC (method 6): R$_t$=3.90 min.

In accordance with general instructions F it is possible to obtain the following compounds:

| Example | Structure | MW | MS | HPLC |
|---|---|---|---|---|
| 38A | 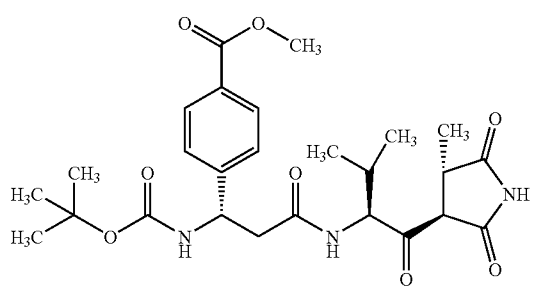 | 517.58 | MS (ES+), m/z (%): 518 (M + H)$^+$ | HPLC (method 8): R$_t$ = 2.60 min |
| 39A | 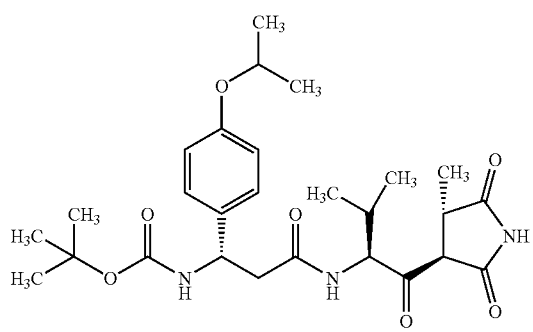 | 517.62 | MS (ES+), m/z (%): 518 (M + H)$^+$ | HPLC (method 14): R$_t$ = 4.42 min |
| 40A | 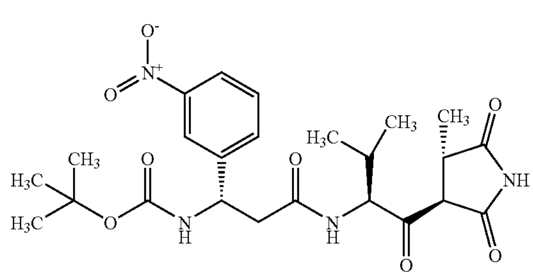 | 504.54 | MS (ES−), m/z (%): 503 (M − H)$^-$ | HPLC (method 6): R$_t$ = 3.99 min |

General Instructions G: Deblocking of Boc-protected derivatives

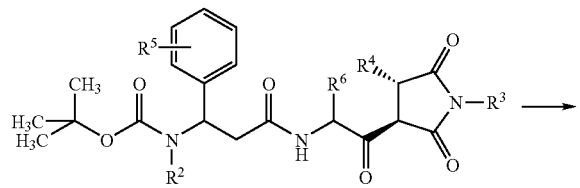

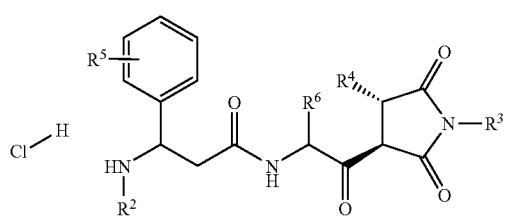

The tert-butyloxycarbonyl (BOC) protected amine derivative (optionally as a solution in dioxane) is admixed at 0° C. or room temperature with 4N hydrochloric acid solution in 1,4-dioxane (about 0.1 mol/l) and stirred at room temperature for 2 to 24 h before being concentrated under reduced pressure. The residue can be reacted further without additional purification or if desired is treated with dichloromethane and diethyl ether. The precipitated crystals are filtered off with suction and dried under a high vacuum. This gives the product as the hydrochloride.

Example 41A (S)-3-Amino-{(S)-2-methyl-1-[1-((3R,4S)-4-methyl-2,5-dioxopyrrolidin-3-yl)-methanoyl]-propyl}-3-phenylpropionamide hydrochloride

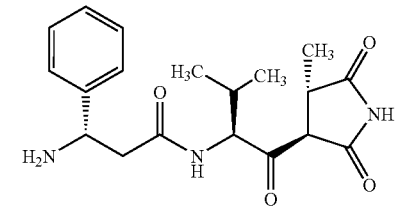

Synthesis in accordance with general instructions G.

$^1$H-NMR (200 MHz, d$_6$-DMSO): δ=11.49 (br. s, 1 H), 8.5 (br. s, about 3 H), 7.54-7.32 (m, 5 H), 4.69-4.55 (m, 2 H), 3.89 (d, 1 H), 3.06-2.80 (m, 3 H), 2.39-2.25 (m, 1H), 1.01 (d, 3 H), 0.81 (d, 3 H), 0.75 (d, 3 H).

MS (ES+): m/z (%)=360 (M+H)$^+$ (100).

HPLC (method 4): R$_t$=1.44 min.

In accordance with general instructions G it is possible to obtain the following compounds:

| Example | Structure | MW | MS | HPLC |
|---------|-----------|-----|-----|------|
| 42A | (structure shown) | 417.46 | MS (ES−), m/z (%): 416 (M − H)$^-$ | HPLC (method 5): R$_t$ = 2.23 min |
| 43A | (structure shown) | 417.51 | MS (ES−), m/z (%): 416 (M − H)$^-$ | HPLC (method 9): R$_t$ = 2.97 min |

| Example | Structure | MW | MS | HPLC |
|---|---|---|---|---|
| 44A | 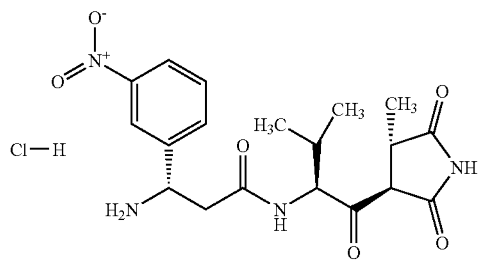 | 404.42 | | |

In the same way as for Example 1A the following compounds are obtained by reacting (3S)-3-methyldihydro-2,5-furandione with the corresponding primary amines, hydroxylamine derivatives or hydrazine derivatives. The crude products can be purified by RP-HPLC (mobile phase: water-acetonitrile, gradient).

| Example | Structure | MW | MS | HPLC |
|---|---|---|---|---|
| 45A | 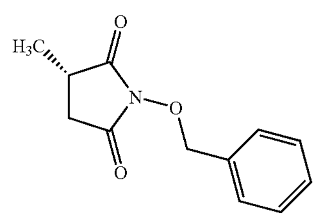 | 219.24 | | HPLC (method 6): $R_t = 3.37$ min |
| 46A | 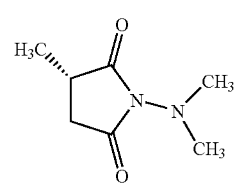 | 156.18 | MS (ESI+), m/z: 157 (M + H)$^+$ | HPLC (method 19): $R_t = 2.62$ min |
| 47A | 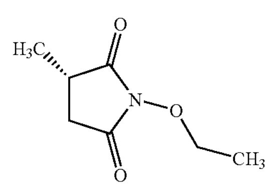 | 157.17 | MS (DCI), m/z: 175 (M + NH$_4$)$^+$ | HPLC (method 20): $R_t = 1.70$ min |
| 48A | 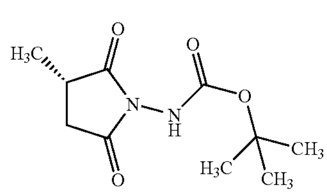 | 228.25 | MS (DCI), m/z: 246 (M + NH$_4$)$^+$ | HPLC (method 20): $R_t = 2.09$ min |
| 49A | 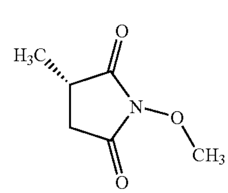 | 143.14 | MS (ESI+), m/z: 144 (M + H)$^+$ | |

-continued

| Example | Structure | MW | MS | HPLC |
|---|---|---|---|---|
| 50A | 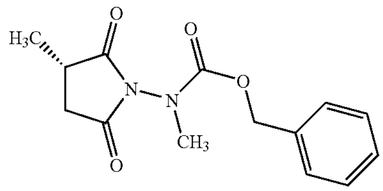 | 276.29 | MS (DCI), m/z: 294 (M + NH₄)⁺ | HPLC (method 21): $R_t$ = 2.80 min |

General Instructions J: Reaction of N-tert-butoxycarbonyl-protected amino acids with 2,5-pyrrolidinedione derivatives

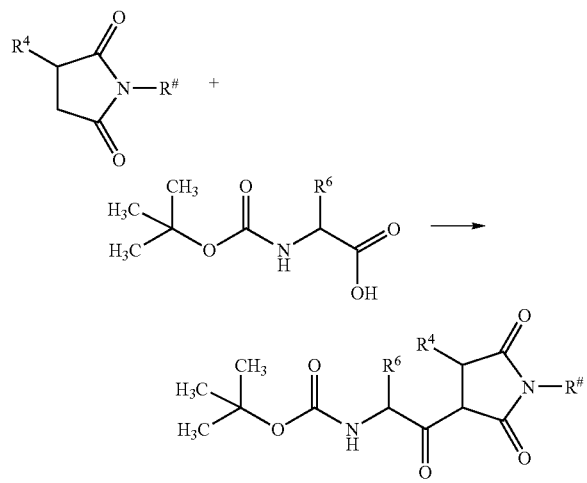

The N-tert-butoxycarbonyl-protected amino acid (1 eq.) and N,N-carbonyldiimidazole (1.1 eq.) are stirred in tetrahydrofuran (about 0.1-1 mol/l) at room temperature for 2 h. The 2,5-pyrrolidinedione (1 eq.) is then added to this mixture and the total mixture is added dropwise over the course of 30 minutes to a 1 molar solution of lithium hexamethyldisilazide (2 eq.) in THF, which is cooled at −65° C. After the end of the addition stirring is continued at −65° C. for 15 minutes more, and then saturated aqueous ammonium chloride solution is added. After the reaction mixture has been warmed to room temperature it is diluted with diethyl ether and the organic phase is washed with saturated aqueous sodium chloride solution, dried over magnesium sulfate, filtered and subsequently concentrated. The crude product is purified by RP-HPLC (mobile phase: water-acetonitrile, gradient).

In accordance with general instructions J it is possible by reacting the corresponding N-tert-butoxycarbonyl-protected amino acids (for the preparation of non-natural alpha-amino acids see, for example, A. A. Cord et al., *J. Med. Chem.* 2001, 44, 787-805; K. Mai, G. Patil, *Tetrahedron Lett*. 1984, 25, 4583-4586; N. A. Hassan, E. Bayer, J. C. Jochims, *J. Chem. Soc., Perkin Trans.* 1 1998, 3747-3757; for the tert-butoxycarbonyl protection see, e.g., T. W. Greene, P. G. M. Wuts, Protective Groups in Organic Synthesis, 3$^{rd}$ Edt. 1999, J. Wiley & Sons, Inc.) with 2,5-pyrrolidinediones to obtain the following derivatives:

| Example | Structure | MW | MS | HPLC |
|---|---|---|---|---|
| 51A | 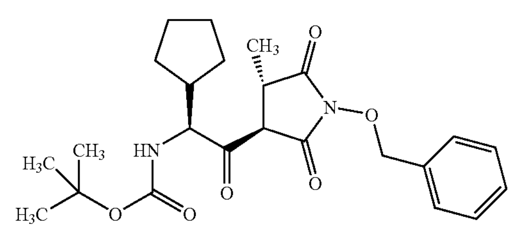 | 444.53 | MS (ES−), m/z: 443 (M − H)⁻ | HPLC (method 18): $R_t$ = 4.11 min |
| 52A | 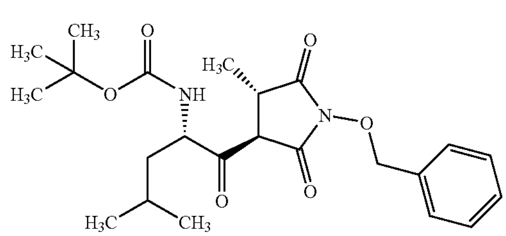 | 432.51 | MS (ES−), m/z: 431 (M − H)⁻ | HPLC (method 6): $R_t$ = 4.88 min |

-continued
| Example | Structure | MW | MS | HPLC |
|---|---|---|---|---|
| 53A | 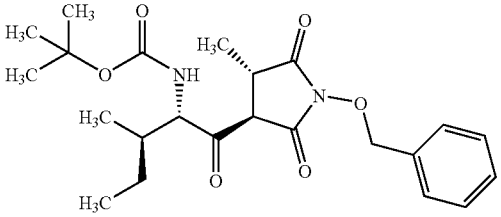 | 432.51 | MS (ES−), m/z: 431 (M − H)− | HPLC (method 13): R$_t$ = 5.08 min |
| 54A | 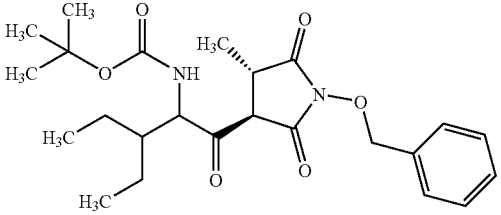 | 446.54 | MS (ES−), m/z: 445 (M − H)− | HPLC (method 17): R$_t$ = 4.42 min |
| 55A | 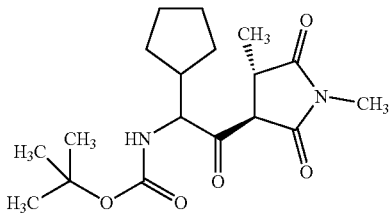 | 352.43 | MS (ES−), m/z: 351 (M − H)− | HPLC (method 14): R$_t$ = 4.61 min |
| 56A | 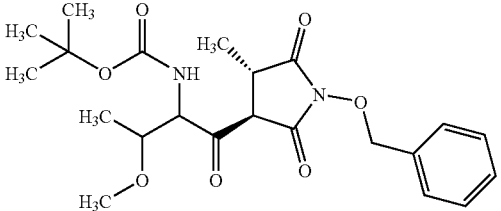 | 434.49 | MS (ES−), m/z: 433 (M − H)− | HPLC (method 17): R$_t$ = 3.98 min |
| 57A | 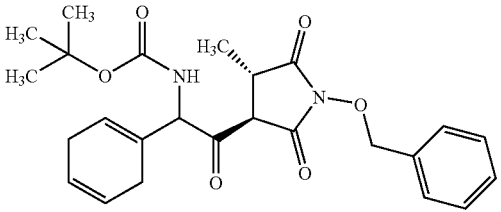 | 454.52 | MS (ES−), m/z: 453 (M − H)− | HPLC (method 22): R$_t$ = 4.41 min |
| 58A | 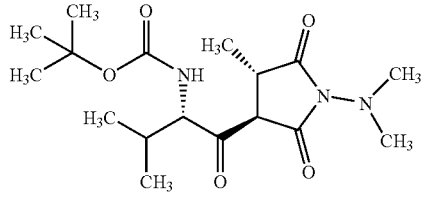 | 355.43 | MS (ES+), m/z: 378 (M + Na)+ | HPLC (method 19): R$_t$ = 4.12 min |
| 59A | 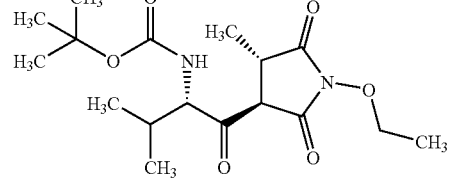 | 356.42 | MS (ES−), m/z: 355 (M − H)− | HPLC (method 20): R$_t$ = 3.64 min |

-continued

| Example | Structure | MW | MS | HPLC |
|---|---|---|---|---|
| 60A | 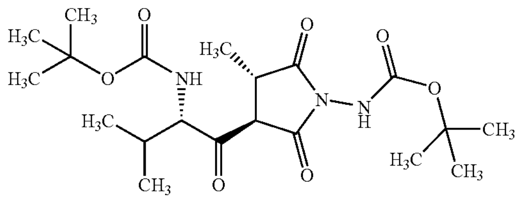 | 427.50 | MS (ES−), m/z: 426 (M − H)− | HPLC (method 20): R$_t$ = 3.73 min |
| 61A | 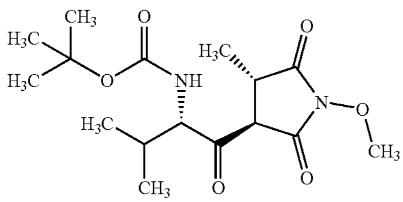 | 342.39 | MS (ES−), m/z: 341 (M − H)− | HPLC (method 19): R$_t$ = 4.18 min |
| 62A | 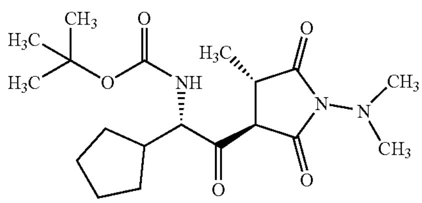 | 381.47 | MS (ES−), m/z: 380 (M − H)− | HPLC (method 21): R$_t$ = 3.43 min |
| 63A | 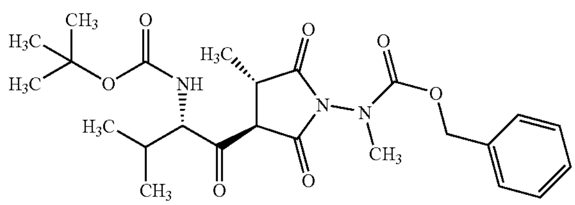 | 475.54 | MS (ES−), m/z: 474 (M − H)− | HPLC (method 20): R$_t$ = 3.91 min |
| 64A | 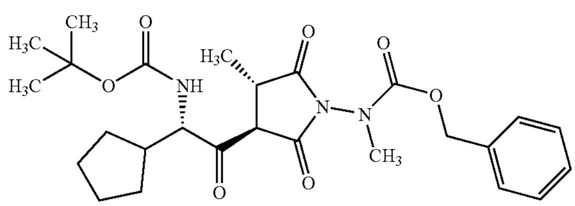 | 501.58 | MS (ES−), m/z: 500 (M − H)− | HPLC (method 21): R$_t$ = 3.93 min |
| 65A | 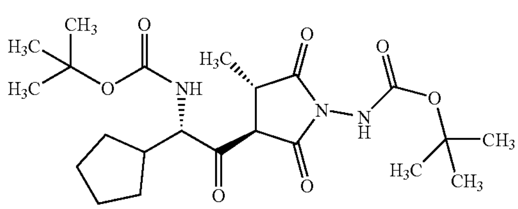 | 453.53 | MS (ES−), m/z: 452 (M − H)− | HPLC (method 21): R$_t$ = 3.61 min |
| 66A | 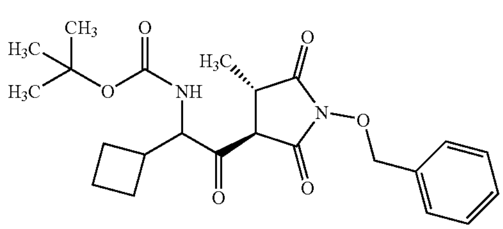 | 430.51 | MS (ES+), m/z: 453 (M + Na)+ | HPLC (method 20): R$_t$ = 4.32 min |

In accordance with general instructions A it is possible to obtain the following compounds:

| Example | Structure | MW | MS | HPLC |
|---|---|---|---|---|
| 67A | 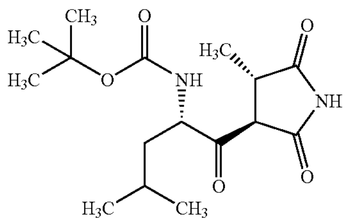 | 326.39 | MS (ES−), m/z: 325 (M − H)⁻ | HPLC (method 5): R_t = 3.91 min |
| 68A | 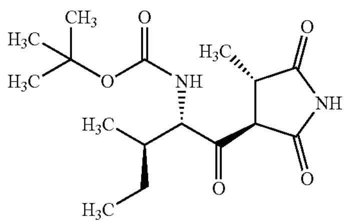 | 326.39 | MS (ES−), m/z: 325 (M − H)⁻ | HPLC (method 12): R_t = 2.88 min |
| 69A | 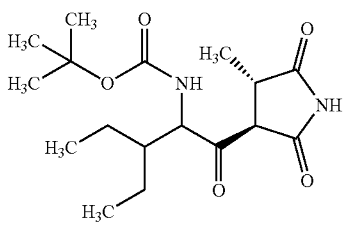 | 340.42 | MS (ES−), m/z: 339 (M − H)⁻ | HPLC (method 17): R_t = 3.59 min |
| 70A | 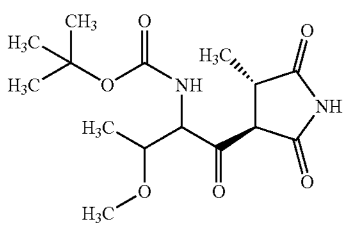 | 328.26 | MS (ES+), m/z: 351 (M + Na)⁺ | HPLC (method 20): R_t = 3.18 min |
| 71A | 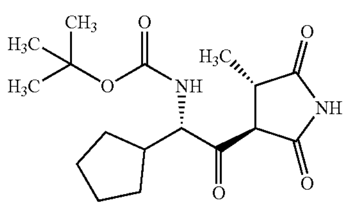 | 338.40 | MS (ES−), m/z: 337 (M − H)⁻ | HPLC (method 17): R_t = 3.57 min |
| 72A | 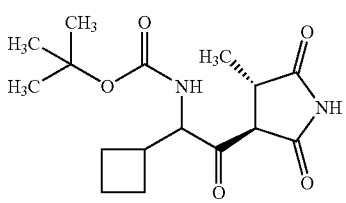 | 324.38 | MS (ES−), m/z: 323 (M − H)⁻ | HPLC (method 19): R_t = 4.02 min |

| Example | Structure | MW | MS | HPLC |
|---|---|---|---|---|
| 73A | *(structure)* | 350.41 | MS (ES−), m/z: 349 (M − H)− | HPLC (method 18): R$_t$ = 3.66 min |

Compound 73A was formed in the course of the reaction of compound 57A.

General Instructions K: Deblocking of benzyloxycarbonyl-protected hydrazine Derivatives General Instructions L: Deblocking of Boc-protected Derivatives

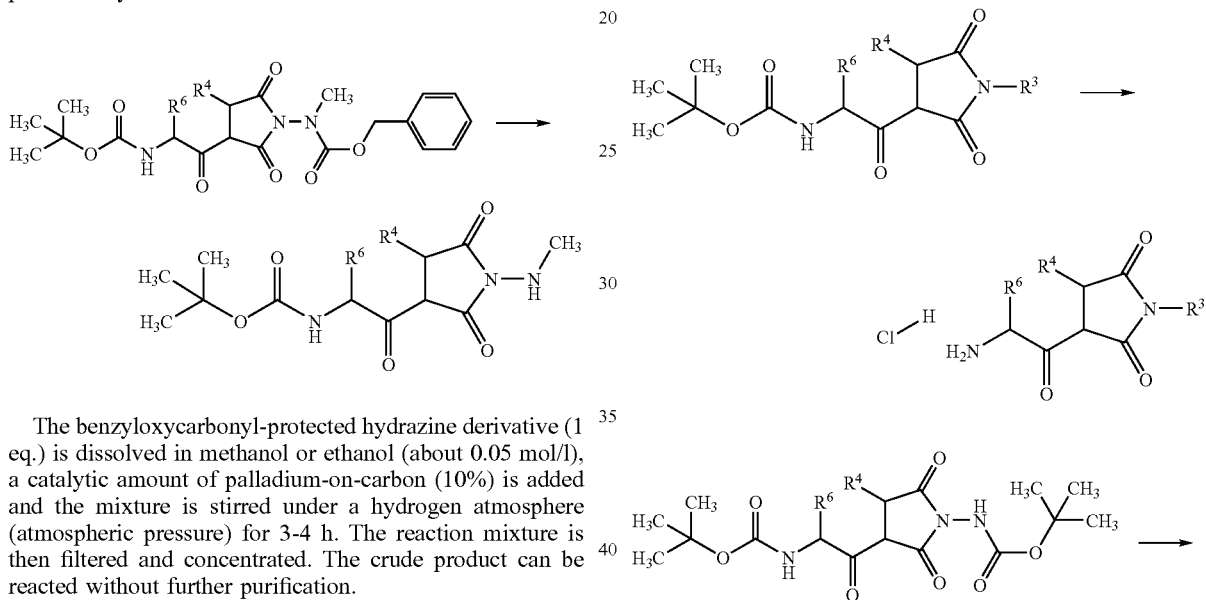

The benzyloxycarbonyl-protected hydrazine derivative (1 eq.) is dissolved in methanol or ethanol (about 0.05 mol/l), a catalytic amount of palladium-on-carbon (10%) is added and the mixture is stirred under a hydrogen atmosphere (atmospheric pressure) for 3-4 h. The reaction mixture is then filtered and concentrated. The crude product can be reacted without further purification.

In accordance with general instructions K is it possible to obtain the following compounds:

| Example | Structure | MW | MS | HPLC |
|---|---|---|---|---|
| 74A | *(structure)* | 341.41 | MS (ES−), m/z: 340 (M − H)− | HPLC (Methode 19): R$_t$ = 4.00 min |
| 75A | *(structure)* | 367.44 | MS (ES−), m/z: 366 (M − H)− | HPLC (Methode 20): R$_t$ = 3.47 min |

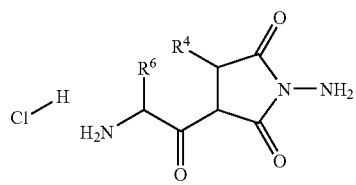

The tert-butyloxycarbonyl (BOC)-protected amine derivative (optionally as a solution in dioxane) is admixed with a 4N solution of hydrochloric acid in 1,4-dioxane (about 0.1 mol/l) and stirred at room temperature for 2-24 h before being concentrated under reduced pressure. The residue can be reacted further without additional purification or if desired is treated with dichloromethane and diethyl ether. The precipitated crystals are filtered off with suction and dried under a high vacuum. The product is obtained as the hydrochloride.

In accordance with general instruction L it is possible to obtain the following compounds:

| Example | Structure | MW |
|---|---|---|
| 76A | 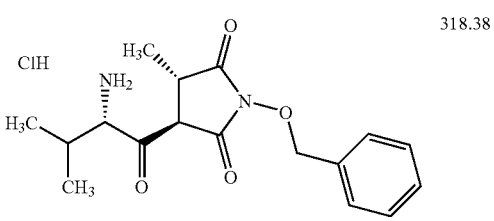 | 238.29 |
| 77A | 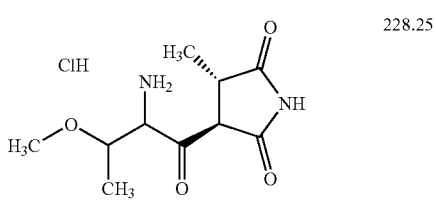 | 226.28 |
| 78A | 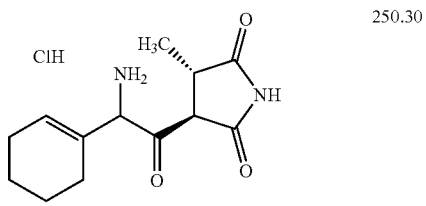 | 226.28 |
| 79A | 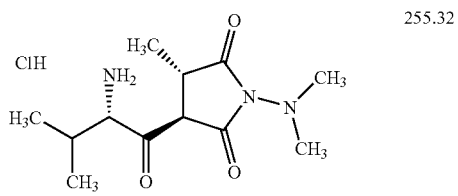 | 240.30 |

-continued

| Example | Structure | MW |
|---|---|---|
| 80A | 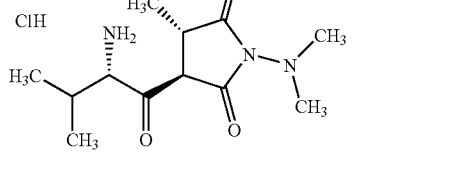 | 252.32 |
| 81A | 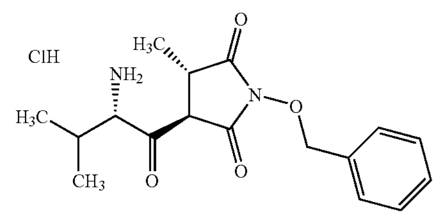 | 318.38 |
| 82A | 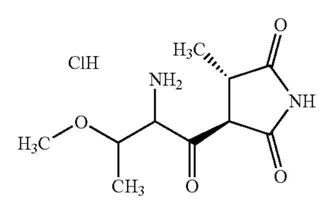 | 228.25 |
| 83A | 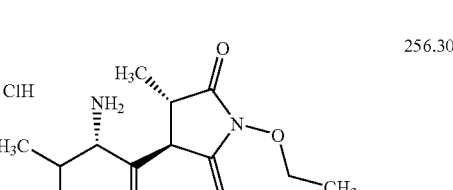 | 250.30 |
| 84A | 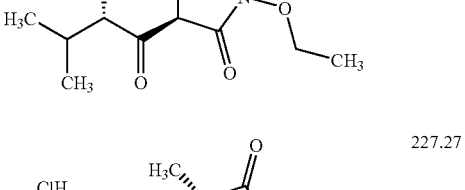 | 255.32 |
| 85A | 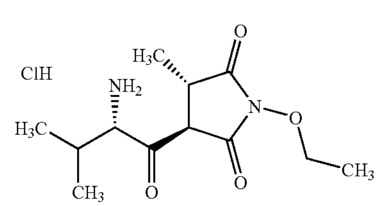 | 256.30 |
| 86A | 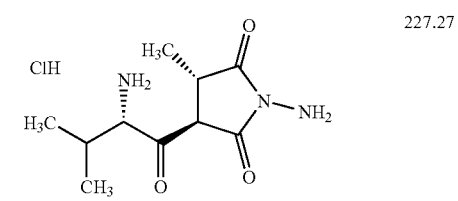 | 227.27 |

| Example | Structure | MW |
|---|---|---|
| 87A | (structure) | 242.28 |
| 88A | (structure) | 281.36 |
| 89A | (structure) | 241.29 |

| Example | Structure | MW |
|---|---|---|
| 90A | (structure) | 267.33 |
| 91A | (structure) | 253.30 |
| 92A | (structure) | 224.26 |

In accordance with general working instructions B it is possible to prepare the following compounds:

| Example | Structure | MW | MS | HPLC |
|---|---|---|---|---|
| 93A | (structure) | 180.2 | MS (ES+), m/z: 180 (M + H)+ | |
| 94A | (structure) | 230.3 | MS (ES+), m/z: 231 (M + H)+ | HPLC (method 20): $R_t$ = 1.70 min) |
| 95A | (structure) | 229.3 | MS (ES+), m/z: 230 (M + H)+ | HPLC (method 19): $R_t$ = 1.75 min) |

-continued

| Example | Structure | MW | MS | HPLC |
|---|---|---|---|---|
| 96A | (3-thienyl)-CH(NH₂)-CH₂-C(=O)-O-CH₃ | 185.3 | MS (ES+), m/z: 186 (M + H)⁺ | |
| 97A | (2-furyl)-CH(NH₂)-CH₂-C(=O)-O-CH₃ | 169.2 | MS (ES+), m/z: 170 (M + H)⁺ | |
| 98A | (5-chloro-2-thienyl)-CH(NH₂)-CH₂-C(=O)-O-CH₃ | 219.69 | MS (ES+), m/z: 220 (M + H)⁺ | |
| 99A | (4-bromo-2-thienyl)-CH(NH₂)-CH₂-C(=O)-O-CH₃ | 264.14 | MS (ES+), m/z: 264 (M + H)⁺ | |

In accordance with general instructions C it is possible to obtain the following compounds:

| Example | Structure | MW | MS |
|---|---|---|---|
| 100A | pyridine-2-C(=O)-NH-CH(3-thienyl)-CH₂-C(=O)-O-CH₃ | 290.34 | MS (ES+), m/z (%): 291 (M + H)⁺ |
| 101A | pyridine-2-C(=O)-NH-CH(2-furyl)-CH₂-C(=O)-O-CH₃ | 274.28 | MS (ES+), m/z (%): 275 (M + H)⁺ |

-continued

| Example | Structure | MW | MS |
|---|---|---|---|
| 102A | 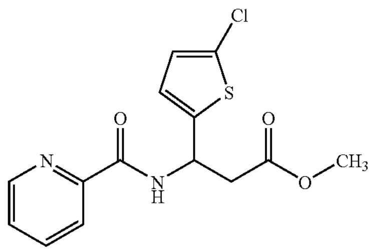 | 324.79 | MS (ES+), m/z (%): 325 (M + H)+ |
| 103A | 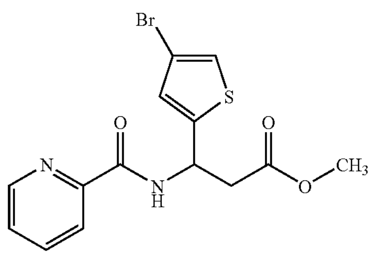 | 369.24 | MS (ES+), m/z (%): 369 (M + H)+ |

General Instructions M: Reaction of 3-aminopropionic acid alkyl esters with carbonyl chlorides

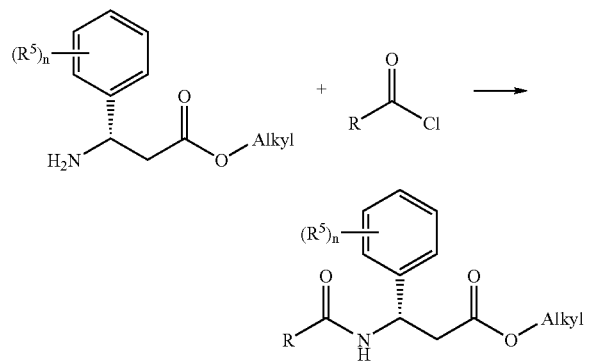

The 3-aminopropionic acid alkyl ester is introduced in dichloromethane (about 0.1-0.4 mol/l) at room temperature and 2-3 eq. of diisopropylethylamine and 1.2 eq. of the carbonyl chloride are added. The mixture is stirred at room temperature for 2-3 h. Then water is added to the reaction mixture and the organic phase is separated off, dried over sodium sulfate, filtered and concentrated. The residue can be recrystallized from dichloromethane and diethyl ether or purified by means of chromatography on silica gel (mobile phase: mixtures of dichloromethane and ethyl acetate).

In accordance with general instructions M it is possible to obtain the following compounds:

| Example | Structure | MW | MS |
|---|---|---|---|
| 104A | 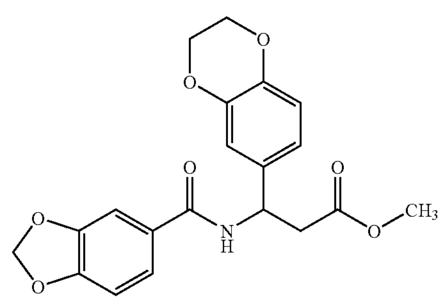 | 385.38 | MS (ES+), m/z (%): 386 (M + H)+ |

| Example | Structure | MW | MS |
|---|---|---|---|
| 105A | 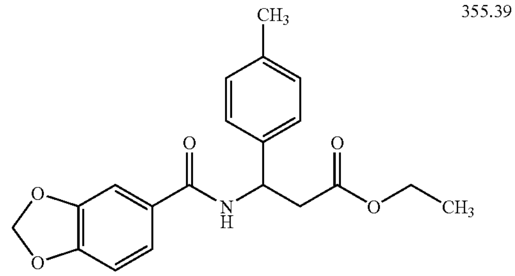 | 355.39 | MS (ES+), m/z (%): 356 (M + H)+ |
In accordance with general instructions D it is possible to obtain the following compounds:
| Example | Structure | MW | MS | HPLC |
|---|---|---|---|---|
| 106A | 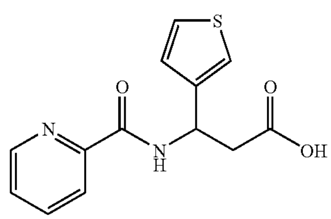 | 276.32 | MS (ES+), m/z (%): 277 (M + H)+ | HPLC (method 9): R$_t$ = 3.55 min |
| 107A | 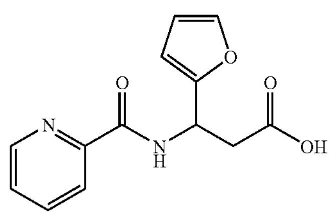 | 260.25 | MS (ES+), m/z (%): 261 (M + H)+ | HPLC (method 9): R$_t$ = 3.43 min |
| 108A | 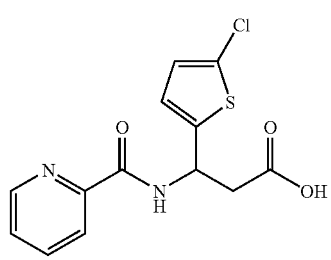 | 310.76 | MS (ES+), m/z (%): 311 (M + H)+ | HPLC (method 9): R$_t$ = 3.92 min |
| 109A | 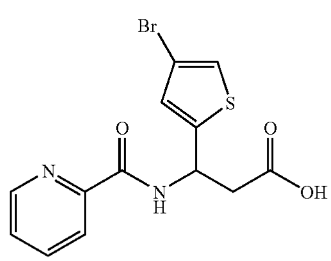 | 355.21 | MS (ES+), m/z (%): 355 (M + H)+ | HPLC (method 9): R$_t$ = 3.89 min |

-continued

| Example | Structure | MW | MS | HPLC |
|---|---|---|---|---|
| 110A | 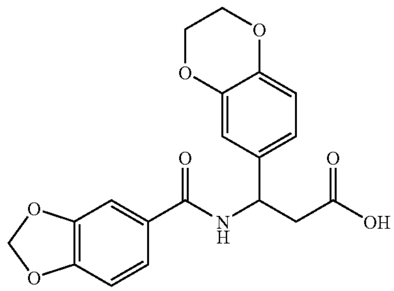 | 371.35 | MS (ES+), m/z (%): 372 (M + H)+ | HPLC (method 9): $R_t$ = 3.64 min |
| 111A | 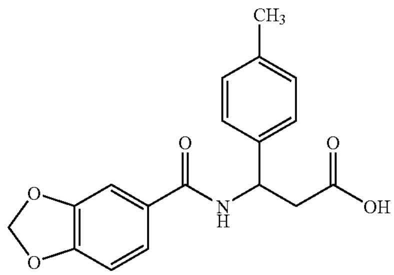 | 327.34 | MS (ES+), m/z (%): 328 (M + H)+ | |

The propionic acid derivatives obtained in this way can be reacted in accordance with the general instructions F described below (acylation of 3-[2-aminoalkanoyl]-2,5-pyrrolidinedione hydrochloride derivatives with carboxylic acid derivatives).

In accordance with general instructions E it is possible to obtain the following compounds:

| Example | Structure | MW | MS | HPLC |
|---|---|---|---|---|
| 112A | 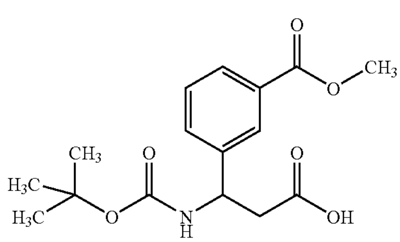 | 323.35 | | HPLC (method 9): $R_t$ = 3.96 min |
| 113A | 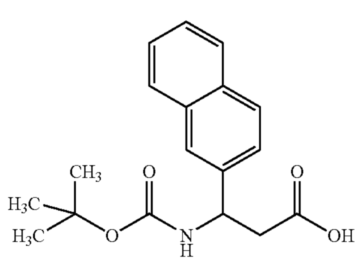 | 315.37 | MS (ESI−), m/z: 314 (M − H)− | HPLC (method 21): $R_t$ = 3.21 min |

-continued

| Example | Structure | MW | MS | HPLC |
|---|---|---|---|---|
| 114A | (3-quinolinyl, Boc-NH-CH-CH2-COOH) | 316.36 | MS (ESI+), m/z: 317 (M + H)+ | HPLC (method 19): $R_t$ = 3.47 min |
| 115A | (4-methoxyphenyl, Boc-NH-CH-CH2-COOH) | 295.33 | MS (ESI+), m/z: 296 (M + H)+ | HPLC (method 20): $R_t$ = 3.00 min |
| 116A | (3,4-dimethoxyphenyl, Boc-NH-CH-CH2-COOH) | 325.36 | | HPLC (method 9): $R_t$ = 3.76 min |
| 117A | (3-pyridyl, Boc-NH-CH-CH2-COOH) | 266.30 | MS (DCI), m/z: 167 (M − 100 + H)+ | HPLC (method 9): $R_t$ = 1.92 min |
| 118A | (3,4-methylenedioxyphenyl, Boc-NH-CH-CH2-COOH) | 309.32 | MS (ESI−), m/z: 308 (M − H)− | HPLC (method 13): $R_t$ = 3.69 min |

In accordance with general instructions F it is possible to obtain the following compounds:

| Example | Structure | MW | MS | HPLC |
|---|---|---|---|---|
| 119A | 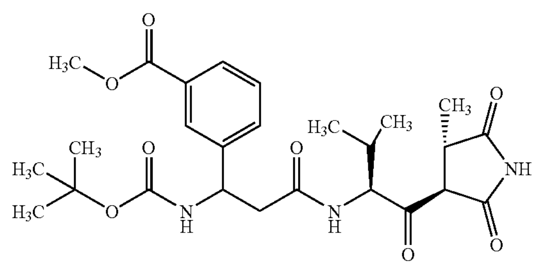 | 517.58 | MS (ESI+), m/z: 518 (M + H)+ | HPLC (method 16): $R_t$ = 2.89 min |
| 120A | 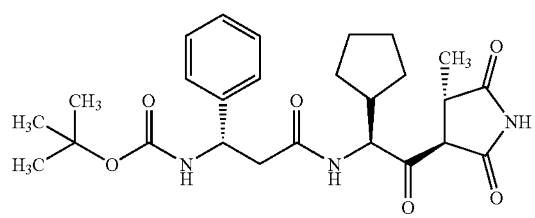 | 485.58 | MS (ESI−), m/z: 484 (M − H)− | HPLC (method 20): $R_t$ = 3.72 min |
| 121A | 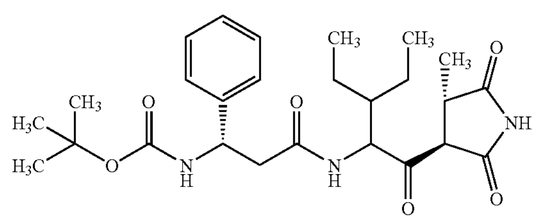 | 487.59 | MS (ESI+), m/z: 488 (M + H)+ | HPLC (method 17): $R_t$ = 3.73 min |
| 122A | 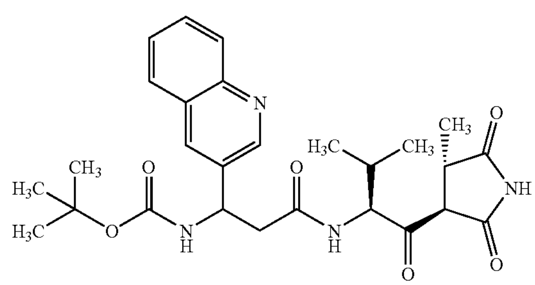 | 510.59 | MS (ESI−), m/z: 509 (M − H)− | HPLC (method 19): $R_t$ = 3.99 min |
| 123A | 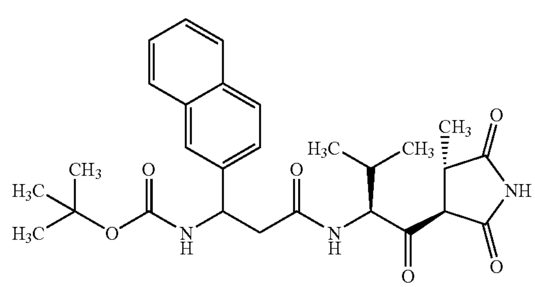 | 509.61 | MS (ESI−), m/z: 508 (M − H)− | HPLC (method 20): $R_t$ = 3.77 min |

| Example | Structure | MW | MS | HPLC |
|---|---|---|---|---|
| 124A | 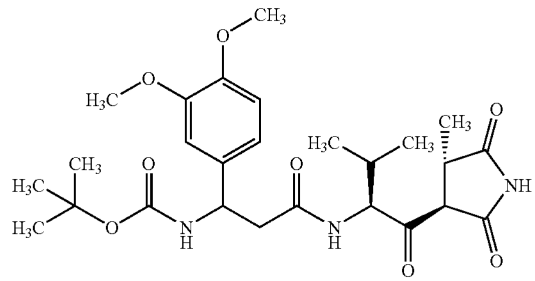 | 519.60 | MS (ESI−), m/z: 518 (M − H)− | HPLC (method 18): R_t = 3.36 min |
| 125A | 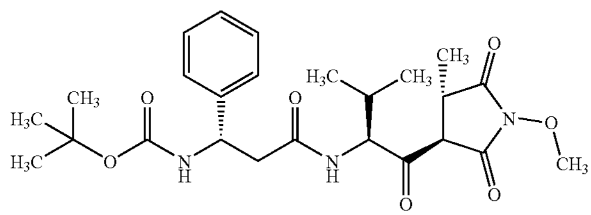 | 489.57 | MS (ESI−), m/z: 488 (M − H)− | HPLC (method 19): R_t = 4.19 min |
| 126A | 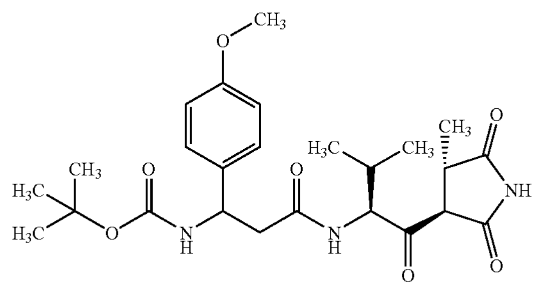 | 489.57 | MS (ESI−), m/z: 488 (M − H)− | HPLC (method 20): R_t = 3.36 min |
| 127A | 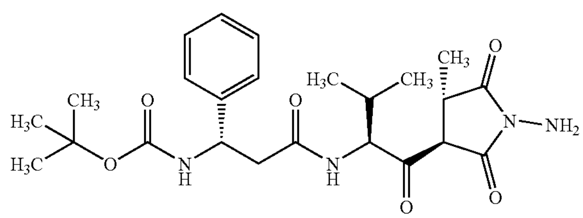 | 474.56 | MS (ESI−), m/z: 473 (M − H)− | HPLC (method 19): R_t = 2.55 min |
| 128A | 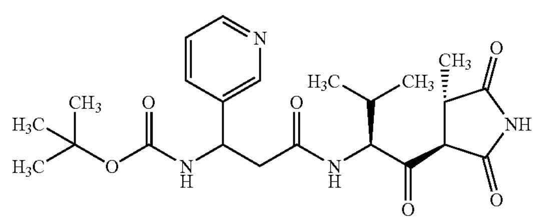 | 460.53 | MS (ESI+), m/z: 461 (M + H)+ | HPLC (method 5): R_t = 2.86 min |
| 129A | 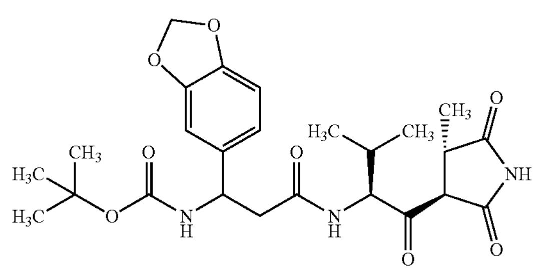 | 503.56 | MS (ESI+), m/z: 504 (M + H)+ | HPLC (method 14): R_t = 4.05 min |

In accordance with general instructions G it is possible to obtain the following compounds:

| Example | Structure | MW | MS | HPLC |
|---|---|---|---|---|
| 130A | 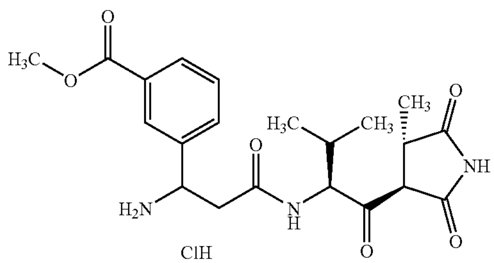 | 417.47 | | |
| 131A | 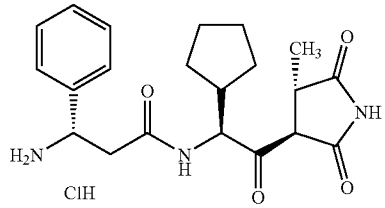 | 385.47 | MS (ESI−), m/z: 384 (M − H)− | HPLC (method 20): R$_t$ = 1.90 min |
| 132A | 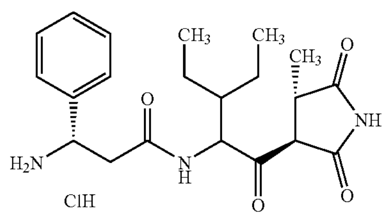 | 387.48 | | |
| 133A | 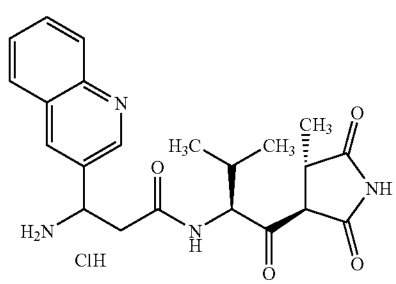 | 410.48 | | HPLC (method 9): R$_t$ = 2.79 min |
| 134A | 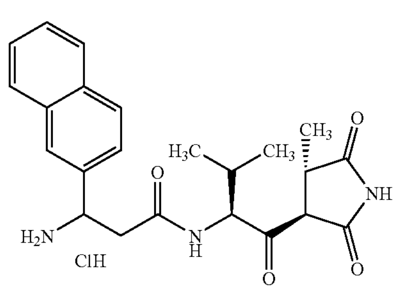 | 409.49 | MS (ESI−), m/z: 408 (M − H)− | HPLC (method 20): R$_t$ = 2.14 and 2.23 min |

| Example | Structure | MW | MS | HPLC |
|---|---|---|---|---|
| 135A | 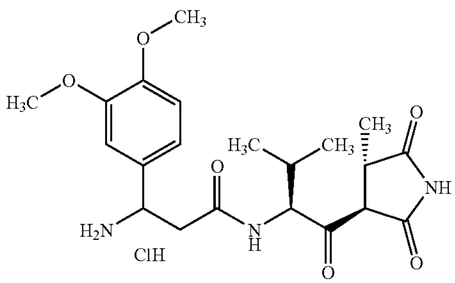 | 419.48 | | HPLC (method 9): $R_t$ = 2.80 min |
| 136A | 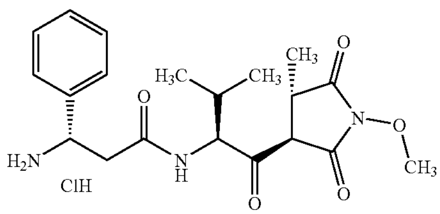 | 389.46 | MS (ESI−), m/z: 388 (M − H)⁻ | HPLC (method 19): $R_t$ = 3.17 min |
| 137A | 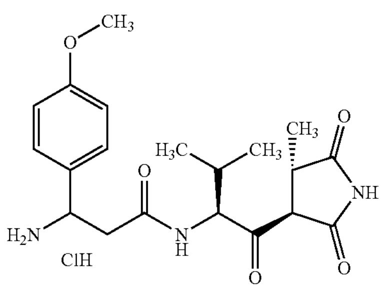 | 389.46 | | HPLC (method 9): $R_t$ = 2.86 min |
| 138A | 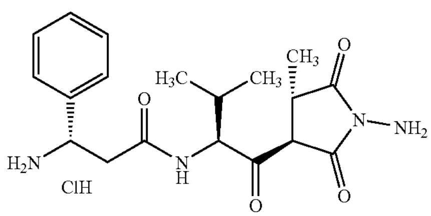 | 374.44 | | |
| 139A | 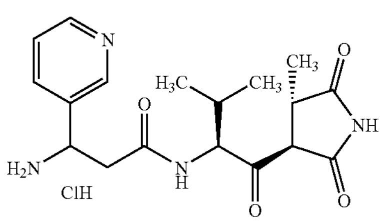 | 360.42 | MS (ESI+), m/z: 361 (M + H)⁺ | |
| 140A | 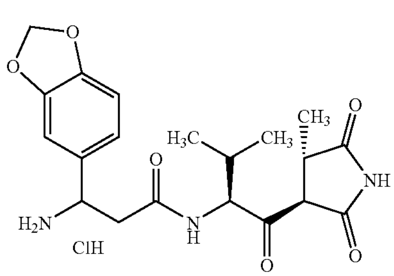 | 403.44 | MS (ESI−), m/z: 402 (M − H)⁻ | HPLC (method 14): $R_t$ = 2.40 min |

PREPARATION EXAMPLES

General Instructions H: Acylation of acylalkylamino Substituted 3-[2-amino-alkanoyl]-2,5-pyrrolidinedione hydrochloride Derivatives with carboxylic acid Derivatives

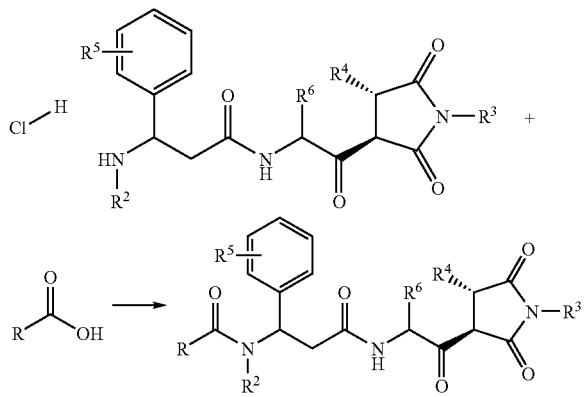

A mixture of amine hydrochloride (1.0 eq.), carboxylic acid (1.2 to 1.3 eq.) and HATU (1.2-1.4 eq.) in solution in absolute N,N-dimethylformamide or in a 1:1 mixture of N,N-dimethylformamide and dichloromethane (0.02-0.2 mol/l) is admixed dropwise at 0° C. with a 0.2-1.0 molar solution of diisopropylethylamine (2.5 to 3.5 eq.) in N,N-dimethylformamide or a 1:1 mixture of N,N-dimethylformamide and dichloromethane over a period of 1 h. When the addition is over the reaction mixture is stirred at 0° C. for another 30 minutes and at room temperature overnight, and then is concentrated under reduced pressure. The product can be obtained by chromatography on silica gel (mobile phases: mixtures of cyclohexane/ethyl acetate or mixtures of dichloromethane and ethanol) or by RP-HPLC (mobile phases: variable gradients of water and acetonitrile), or alternatively by a combination of both methods.

Alternatively the reaction may also take place. in accordance with the following method:

A mixture of amine hydrochloride (1.0 eq.), carboxylic acid (1.2 to 1.3 eq.), triethylamine (2.4-3 eq.) and HOBt (2.4-3 eq.) in absolute dichloromethane or in a mixture of N,N-dimethylformamide and dichloromethane (0.02-0.2 mol/l) is admixed finally with 1.2 eq. of EDC. The reaction mixture is stirred at room temperature (2 h to overnight) before being concentrated under reduced pressure. The residue is taken up in ethyl acetate or dichloromethane and the organic phase is washed with water, saturated sodium hydrogencarbonate solution and saturated sodium chloride solution, dried over sodium sulfate, filtered and concentrated. The product can be purified by chromatography on silica gel (mobile phases: mixtures of cyclohexane/ethyl acetate or mixtures of dichloromethane and ethanol) or by RP-HPLC (mobile phases: variable gradients of water and acetonitrile), or alternatively by a combination of both methods.

In accordance with the above-described instructions for the acylation of 3-[2-aminoalkanoyl]-2,5-pyrrolidinedione hydrochloride derivatives or of acylalkylamino substituted 3-[2-aminoalkanoyl]-2,5-pyrrolidinedione hydrochloride derivatives with carboxylic acid derivatives it is possible to obtain the following compounds.

Example 1

N-{(1S)-3-[((1S)-1-{[(3R,4S)-1,4-Dimethyl-2,5-dioxo-3-pyrrolidinyl]carbonyl}-2-methylpropyl)amino]-3-oxo-1-phenylpropyl}-2-pyridinecarboxamide

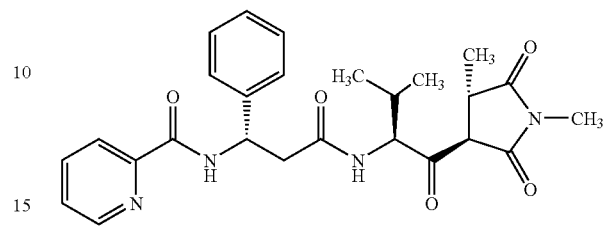

[1] H-NMR (200 MHz, $d_6$-DMSO): δ=9.59 (d, 1 H), 8.65 (d, 1 H), 8.21 (d, 1 H), 7.98 (d, 2 H), 7.61 (q, 1 H), 7.42-7.16 (m, 5H), 5.48-5.32 (m, 1H), 4.76 (dd, 1H), 3.99 (d, 1 H), 3.20-2.92 (m, 2 H), 2.82 (s, 3H), 2.61 (dd, 1H), 2.32-2.13 (m, 1H), 1.13 (d, 3 H), 0.65 (d, 3 H), 0.59 (d, 3 H).

MS (ES+): m/z (%)=479 (M+H)$^+$ (80).

HPLC (method 5): $R_t$=3.79 min.

Example 2

6-Fluoro-N-{(1S)-3-[((1S)-2-methyl-1-{[(3R,4S)-4-methyl-2,5-dioxo-3-pyrrolidinyl]-carbonyl}propyl)amino]-3-oxo-1-phenylpropyl}-2-pyridinecarboxamide

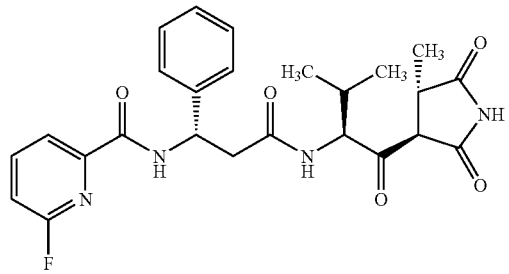

$^1$H-NMR (300 MHz, $d_6$-DMSO): δ=11.31 (s, 1H), 9.32 (d, 1H), 8.22-8.10 (m, 2H), 7.95-7.90 (m, 1 H), 7.45-7.18 (m, 6 H), 5.43-5.33 (m, 1H), 4.70 (dd, 1H), 4.02 (d, 1 H), 3.15 (dd, 1H), 3.01-2.90 (m, 1H), 2.62 (dd, 1H), 2.30-2.18 (m, 1H), 1.10 (d, 3 H), 0.62 (d, 3 H), 0.59 (d, 3 H).

MS (ES-): m/z (%)=481 (M-H)$^-$ (100).

HPLC (method 3): $R_t$=4.19 min.

Example 3

N-{(1S)-3-[((1S)-2-Methyl-1-{[(3R,4S)$_4$-methyl-2,5-dioxo-3-pyrrolidinyl]-carbonyl}propyl)amino]-3-oxo-1-phenylpropyl}-2-pyridinecarboxamide

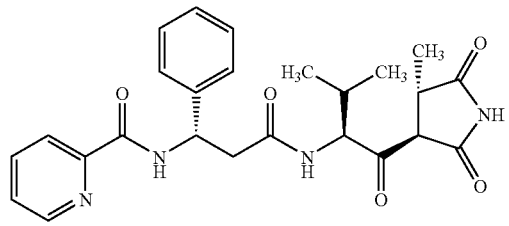

¹H-NMR (300 MHz, d₆-DMSO): δ=11.32 (s, 1H), 9.53 (d, 1H), 8.69-8.65 (m, 1H), 8.15 (d, 1H), 8.02-7.98 (m, 2H), 7.63-7.57 (m, 1H), 7.40-7.18 (m, 5H), 5.45-5.35 (m, 1 H), 4.67 (dd, 1 H), 4.00 (d, 1 H), 3.12 (dd, 1H), 2.97 (dd, 1H), 2.64 (dd, 1 H), 2.29-2.15 (m, 1 H), 1.10 (d, 3 H), 0.60 (d, 3 H), 0.56 (d, 3 H).

MS (ES+): m/z (%)=465 (M+H)⁺ (100).

HPLC (method 6): R$_t$=3.65 min.

Example 4

N-{(1S)-3-[((1S)-2-Methyl-1-{[(3R,4S)₄-methyl-2, 5-dioxo-3-pyrrolidinyl]-carbonyl}propyl)amino]-3-oxo-1-phenylpropyl}-3-quinolinecarboxamide

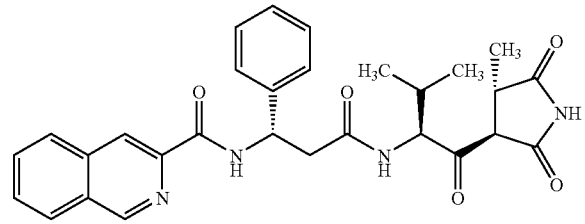

¹ H-NMR (principal conformer) (300 MHz, d₆-DMSO): δ=11.31 (s, 1 H), 9.29-9.12 (m, 2 H), 8.82-8.78 (m, 1 H), 8.15-8.07 (m, 3 H), 7.90-7.82 (m, 1 H), 7.72-7.68 (m, 1H), 7.50-7.20 (m, 5 H), 5.59-5.48 (m, 1 H), 4.71 (dd, 1 H), 3.98 (d, 1H), 3.04-2.70 (m, 3 H), 2.31-2.22 (m, 1 H), 1.09 (d, 3 H), 0.79 (d, 3 H), 0.68 (d, 3 H).

MS (ES+): m/z (%)=515 (M+H)⁺ (100).

HPLC (method 6): R$_t$=3.52 min.

Example 5

N-{(1S)-3-[((1S)-2-Methyl-1-{[(3R,4S)-4-methyl-2, 5-dioxo-3-pyrrolidinyl]-carbonyl}propyl)amino]-3-oxo-1-phenylpropyl}-1-isoquinolinecarboxamide

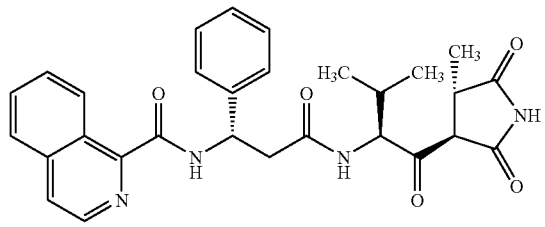

¹ H-NMR (principal conformer) (400 MHz, d₆-DMSO): δ=11.34 (s, 1 H), 9.56 (d, 1H), 9.00 (d, 1 H), 8.58 (d, 1 H), 8.13 (d, 1H), 8.04 (d, 2 H), 7.80 (t, 1 H), 7.70 (t, 1H), 7.45 (d, 2 H), 7.34 (t, 2 H), 7.23 (t, 1 H), 5.52-5.45 (m, 1 H), 4.69 (dd, 1 H), 4.00 (d, 1 H), 3.10 (dd, 1 H), 2.97-2.88 (m, 1H), 2.70-2.62 (m, 1H), 2.21-2.12 (m, 1 H), 1.10 (d, 3 H), 0.59 (d, 3 H), 0.50 (d, 3 H).

MS (ES+): m/z (%)=515 (M+H)⁺ (100).

HPLC (method 6): R$_t$=4.32 min.

Example 6

N-{(1S)-3-[((1S)-2-Methyl-1-{[(3R,4S)₄-methyl-2, 5-dioxo-3-pyrrolidinyl]-carbonyl}propyl)amino]-3-oxo-1-phenylpropyl}-4-phenyl-2-pyridinecarboxamide

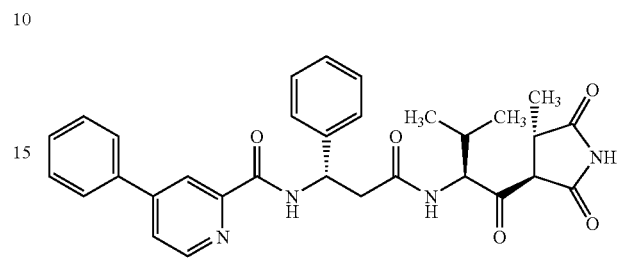

¹ H-NMR (200 MHz, d₆-DMSO): δ=11.36 (s, 1 H), 9.67 (d, 1 H), 8.72 (d, 1 H), 8.26-8.18 (m, 2 H), 7.98-7.92 (m, 1 H), 7.88-7.81 (m, 2 H), 7.60-7.50 (m, 3 H), 7.45-7.20 (m, 5 H), 5.50-5.38 (m, 1 H), 4.75-4.68 (m, 1 H), 4.02 (d, 1 H), 3.20-2.82 (m, 3H), 2.25-2.15 (m, 1 H), 1.10 (d, 3 H), 0.61 (d, 3 H), 0.57 (d, 3 H).

MS (ES+): m/z (%)=541 (M+H)⁺ (100).

HPLC (method 14): R$_t$=4.88 min.

Example 7

6-Fluoro-N-{(1S)-3-[((1S,2S)-2-methyl-1-{[(3R, 4S)-4-methyl-2,5-dioxo-3-pyrrolidinyl] carbonyl}butyl)amino]-3-oxo-1-phenylpropyl}-2-pyridinecarboxamide

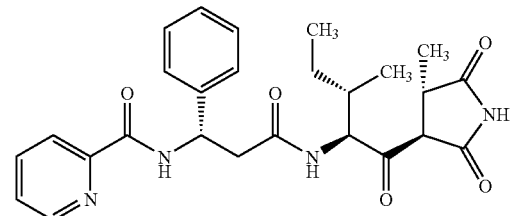

¹H-NMR (300 MHz, d₆-DMSO): δ=11.33 (s, 1H), 9.30 (d, 1H), 8.22-8.12 (m, 2H), 7.95-7.91 (m, 1 H), 7.45-7.20 (m, 6 H), 5.45-5.35 (m, 1H), 4.67 (dd, 1H), 4.03 (d, 1 H), 3.17-3.09 (m, 1 H), 2.97-2.88 (m, 1 H), 2.62-2.54 (m, 1 H), 2.02-1.90 (m, 1H), 1.30-1.15 (m, 2 H), 1.12 (d, 3 H), 0.60 (d, 3 H), 0.56 (t, 3 H).

MS (ES+): m/z (%)=497 (M+H)⁺ (100).

HPLC (method 12): R$_t$=2.95 min.

Example 8

N-[(1S)-3-({(1S)-1-Cyclohexyl-2-[(3R,4S)-4-methyl-2,5-dioxo-3-pyrrolidinyl]-2-oxoethyl}amino)-3-oxo-1-phenylpropyl]-6-fluoro-2-pyridinecarboxamide

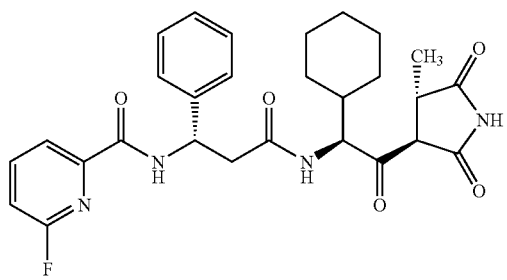

[1] H-NMR (principal conformer) (200 MHz, $d_6$-DMSO): δ=11.35 (s, 1 H), 9.40 (d, 1H), 8.27-8.10 (m, 2 H), 7.99-7.90 (m, 1 H), 7.50-7.18 (m, 6 H), 5.46-5.32 (m, 1 H), 4.73 (dd, 1 H), 4.08 (d, 1 H), 3.26-3.10 (m, 1 H), 3.00-2.80 (m, 2H), 1.98-1.80 (m, 1H), 1.60-1.25 (m, 5 H), 1.12 (d, 3 H), 1.10-0.65 (m, 5 H).

MS (ES+): m/z (%)=523 (M+H)$^+$ (100).

HPLC (method 12): $R_t$=3.12 min.

Example 9

N-[(1S)-3-({1-Cyclopentyl-2-[(3R,4S)-4-methyl-2,5-dioxo-3-pyrrolidinyl]-2-oxoethyl}amino)-3-oxo-1-phenylpropyl]-2-pyridinecarboxamide

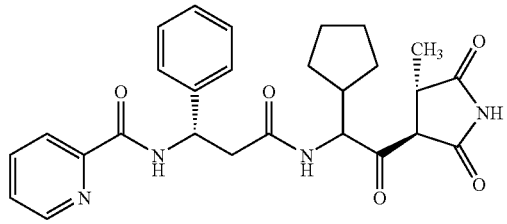

[1] H-NMR (2 diastereomers, approximately 2:1 ratio; a number of conformers) (400 MHz, $d_6$-DMSO): δ=11.35+11.31 (2×s, 1 H), 9.56+9.51-9.41 (d+m, 1 H), 8.71-8.63 (m, 1 H), 8.60-8.42+8.30 (m+d, 1 H), 8.02-7.92 (m, 2 H), 7.65-7.57 (m, 1 H), 7.42-7.18 (m, 5 H), 5.48-5.37 (m, 1 H), 4.65+4.454.28 (t+m, 1 H), 3.99+3.87+3.80 (d+t+d, 1 H), 3.13+3.07-2.98 (dd+m, 1 H), 2.95-2.80 (m, 1 H), 2.70-2.58 (m, 1 H), 2.36-2.18 (m, 1 H), 1.65-0.85 (m, 8H), 1.12+1.01 (2×d, 3 H).

MS (ES+): m/z (%)=491 (M+H)$^+$ (100).

HPLC (method 12): $R_t$=2.79 min.

Example 10

(3S)-N-((1S)-2-Methyl-1-{[(3R,4S)$_4$-methyl-2,5-dioxo-3-pyrrolidinyl]carbonyl}-propyl)-3-phenyl-3-[(2-thienylacetyl)amino]propanamide

[1] H-NMR (300 MHz, $d_6$-DMSO): δ=11.31 (s, 1 H), 8.50 (d, 1 H), 8.08 (d, 1 H), 7.34-7.18 (m, 6H), 6.95-6.90 (m, 1H), 6.89-6.85 (m, 1H), 5.25-5.16 (m, 1H), 4.61 (dd, 1 H), 3.91 (d, 1 H), 3.66 (d, 2 H), 2.90 (dd, 1 H), 2.80-2.60 (m, 2 H), 2.32-2.23 (m, 1 H), 1.07 (d, 3 H), 0.81 (d, 3 H), 0.75 (d, 3 H).

MS (ES–): m/z (%)=482 (M–H)$^-$ (100).

HPLC (method 5): $R_t$=3.72 min.

| Example | Structure | MW | MS | HPLC |
| --- | --- | --- | --- | --- |
| 11 | 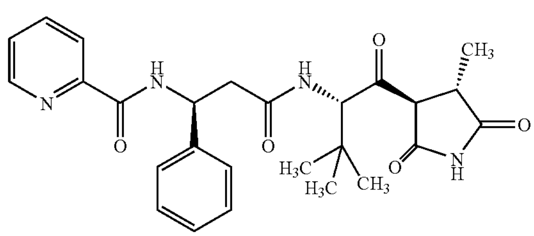 | 478.55 | MS (ES+), m/z (%): 479 (M + H)$^+$ (100) | HPLC (method 5) $R_t$ = 3.69 min |

-continued

| Example | Structure | MW | MS | HPLC |
|---|---|---|---|---|
| 12 | 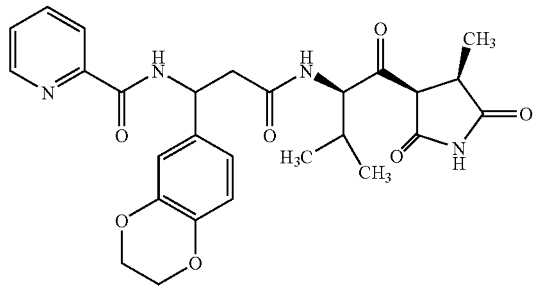 | 522.55 | MS (ES+), m/z (%): 523 (M + H)+ (75) | HPLC (method 9) R$_t$ = 3.81 min |
| 13 | 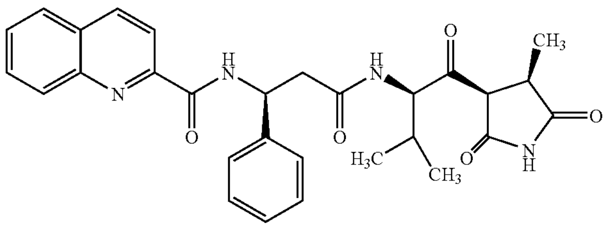 | 514.58 | MS (ES+), m/z (%): 515 (M + H)+ (100) | HPLC (method 5) R$_t$ = 3.97 min |
| 14 | 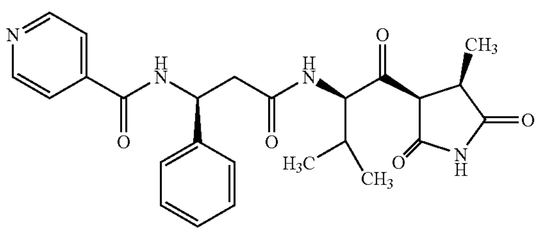 | 464.52 | MS (ES+), m/z (%): 465 (M + H)+ (100) | HPLC (method 5) R$_t$ = 3.01 min |
| 15 | 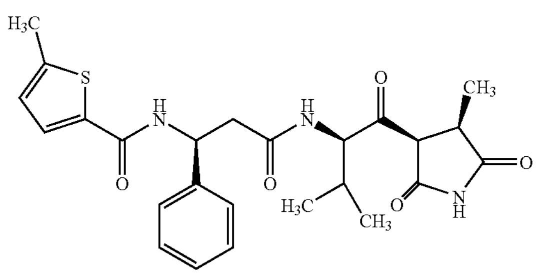 | 483.59 | MS (ES+), m/z (%): 506 (M + Na)+ (100) | HPLC (method 5) R$_t$ = 3.74 min |
| 16 | 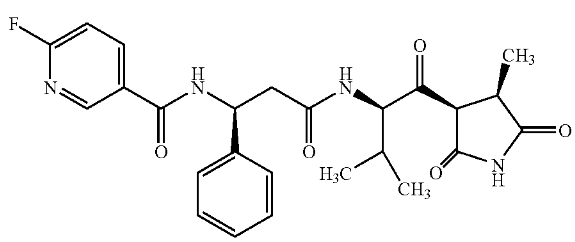 | 482.51 | MS (ES+), m/z (%): 505 (M + Na)+ (100) | HPLC (method 6) R$_t$ = 3.48 min |
| 17 | 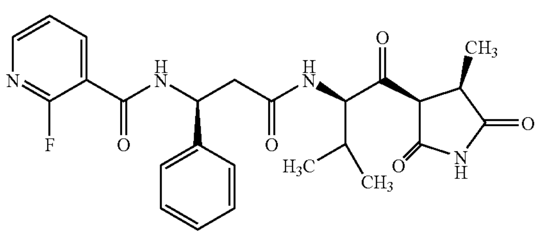 | 482.51 | MS (ES−), m/z (%): 481 (M − H+) (100) | HPLC (method 6) R$_t$ = 3.46 min |

-continued

| Example | Structure | MW | MS | HPLC |
|---|---|---|---|---|
| 18 | 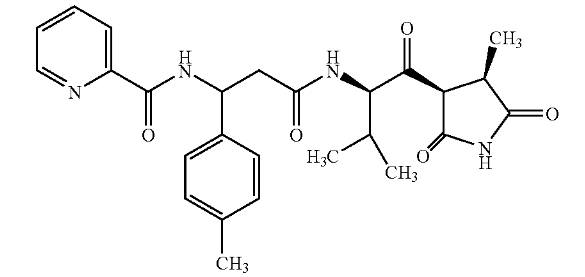 | 478.55 | MS (ES+), m/z (%): 479 (M + H)+ (45) | HPLC (method 9) R$_t$ = 4.03 min |
| 19 | 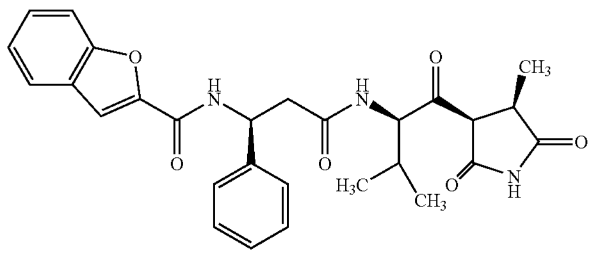 | 503.55 | MS (ES+), m/z (%): 523 (M + Na)+ (100) | HPLC (method 6) R$_t$ = 3.94 min |
| 20 | 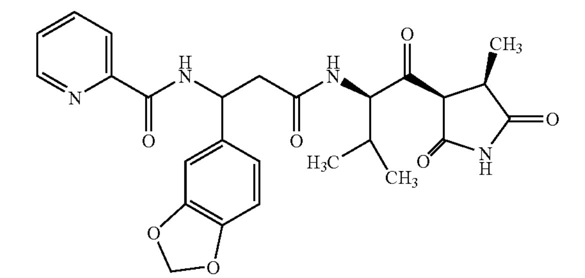 | 508.53 | MS (ES+), m/z (%): 509 (M + H)+ (90) | HPLC (method 9) R$_t$ = 3.82 min |
| 21 | 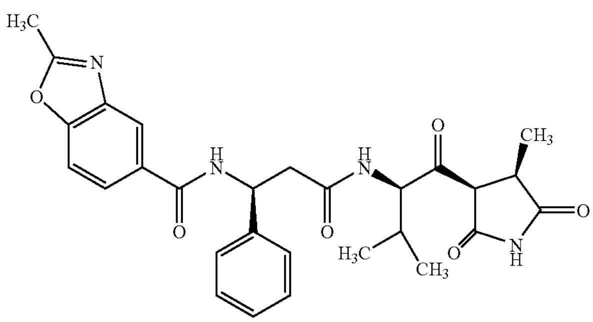 | 518.57 | MS (ES+), m/z (%): 519 (M + H)+ (100) | HPLC (method 3) R$_t$ = 3.95 min |
| 22 | 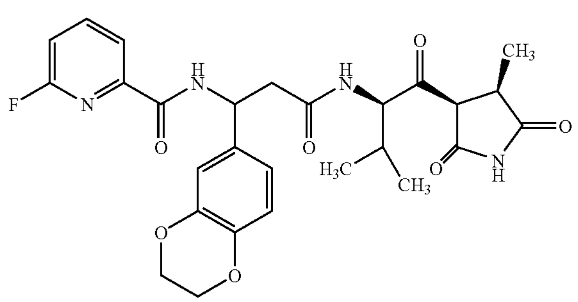 | 540.55 | MS (ES+), m/z (%): 541 (M + H)+ (35) | HPLC (method 9) R$_t$ = 3.92 min |

-continued

| Example | Structure | MW | MS | HPLC |
|---------|-----------|-----|-----|------|
| 23 | 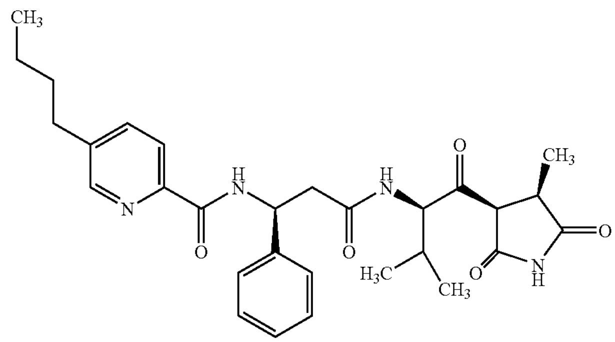 | 520.63 | MS (ES−), m/z (%): 519 (M − H)⁻ (100) | HPLC (method 5) R$_t$ = 4.6 min |
| 24 | 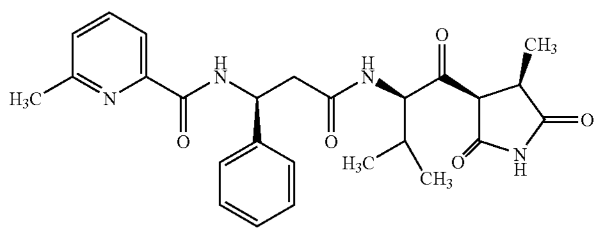 | 478.55 | MS (ES−), m/z (%): 477 (M − H)⁻ (100) | HPLC (method 5) R$_t$ = 3.9 min |
| 25 | 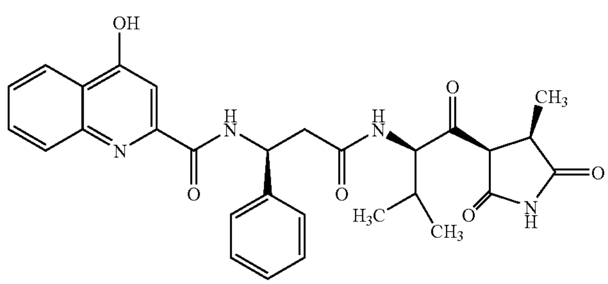 | 530.58 | MS (ES+), m/z (%): 531 (M + H)⁺ (100) | HPLC (method 6) R$_t$ = 3.70 min |
| 26 | 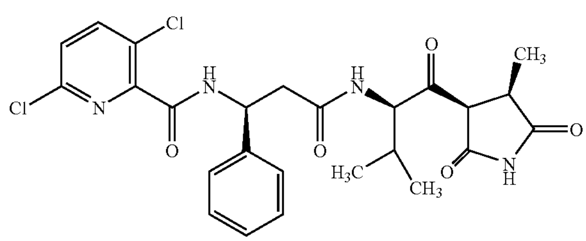 | 533.41 | MS (ES+), m/z (%): 533 (M + H)⁺ (100) | HPLC (method 6) R$_t$ = 4.20 min |
| 27 | 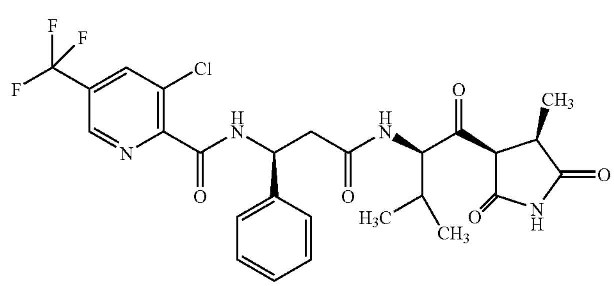 | 566.96 | MS (ES+), m/z (%): 567 (M + H)⁺ (100) | HPLC (method 6) R$_t$ = 4.42 min |

-continued

| Example | Structure | MW | MS | HPLC |
|---|---|---|---|---|
| 28 | 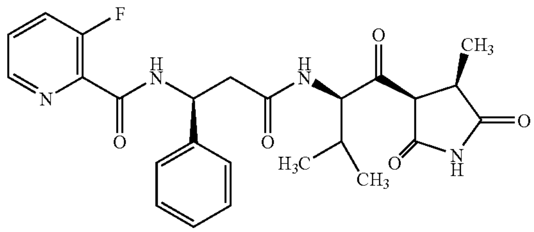 | 482.51 | MS (ES+), m/z (%): 483 (M + H)+ (100) | HPLC (method 11) R$_t$ = 2.66 min |
| 29 | 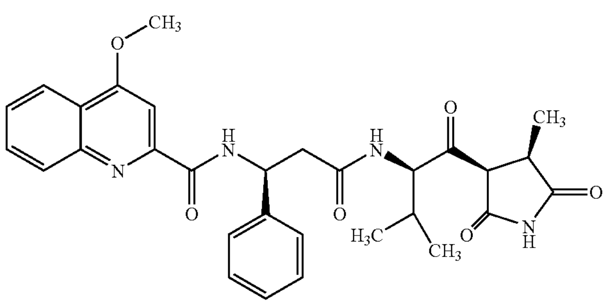 | 544.60 | MS (ES+), m/z (%): 545 (M + H)+ (100) | HPLC (method 14) R$_t$ = 4.5 min |
| 30 | 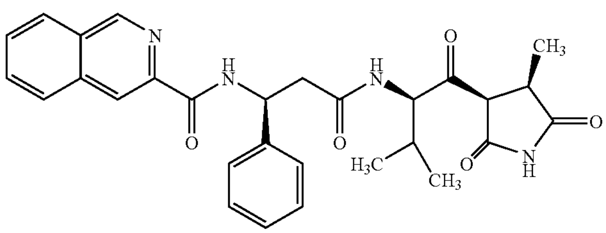 | 514.58 | MS (ES−), m/z (%): 513 (M − H)− (100) | HPLC (method 14) R$_t$ = 4.40 min |
| 31 | 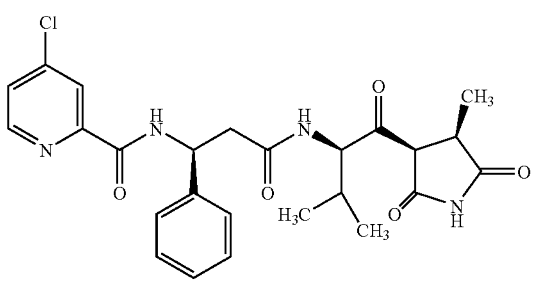 | 498.96 | MS (ES−), m/z (%): 497 (M − H)− (100) | HPLC (method 14) R$_t$ = 4.37 min |
| 32 | 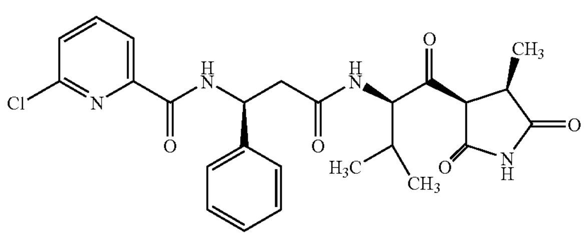 | 498.96 | MS (ES+), m/z (%): 521 (M + Na)+ (100) | HPLC (method 13) R$_t$ = 4.05 min |
| 33 | 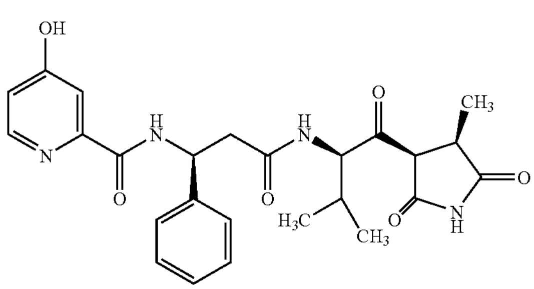 | 480.52 | MS (ES+), m/z (%): 481 (M + H)+ (100) | HPLC (method 14) R$_t$ = 3.65 min |

-continued

| Example | Structure | MW | MS | HPLC |
|---|---|---|---|---|
| 34 | 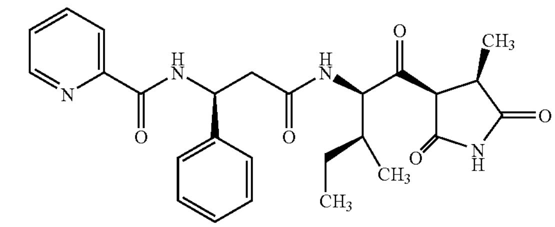 | 478.55 | MS (ES+), m/z (%): 479 (M + H)+ (100) | HPLC (method 13) R_t = 3.98 min |
| 35 | 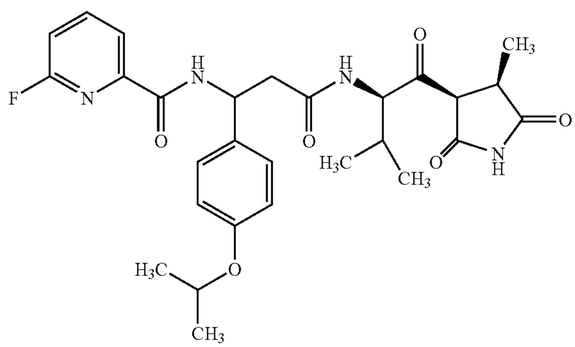 | 540.59 | MS (ES−), m/z (%): 539 (M − H)− (100) | HPLC (method 11) R_t = 2.73 min |
| 36 | 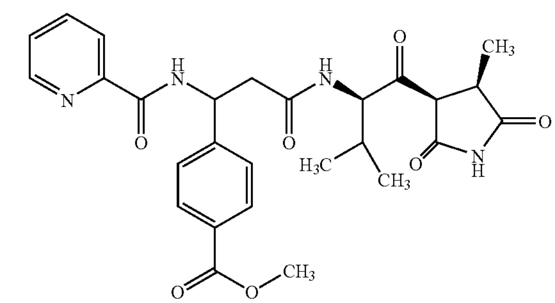 | 522.55 | MS (ES−), m/z (%): 521 (M − H)− (100) | HPLC (method 5) R_t = 3.67 min |
| 37 | 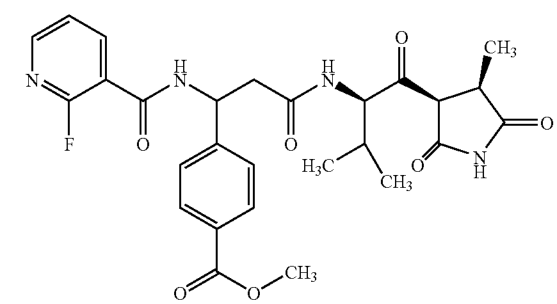 | 540.55 | MS (ES+), m/z (%): 541 (M + H)+ (100) | HPLC (method 9) R_t = 3.75 min |
| 38 | 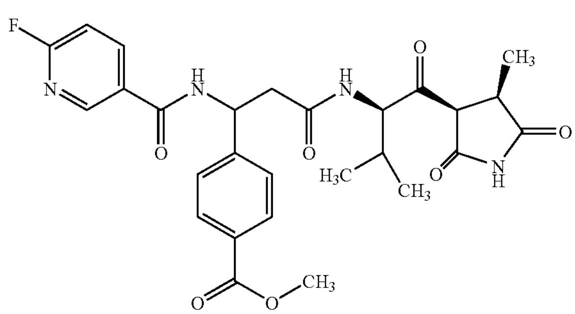 | 540.55 | MS (ES+), m/z (%): 541 (M + H)+ (100) | HPLC (method 9) R_t = 3.80 min |

-continued

| Example | Structure | MW | MS | HPLC |
|---|---|---|---|---|
| 39 | 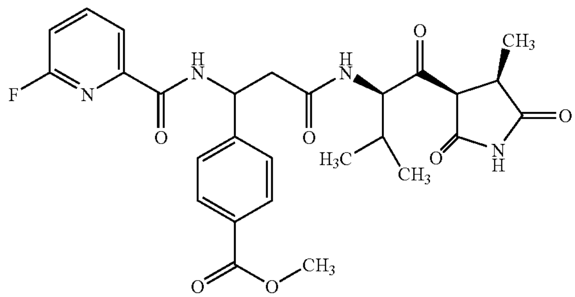 | 540.55 | MS (ES+), m/z (%): 541 (M + H)+ (100) | HPLC (method 14) R_t = 4.12 min |
| 40 | 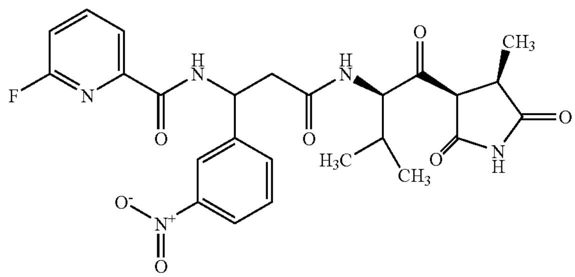 | 527.51 | MS (ES+), m/z (%): 528 (M + H)+ (100) | HPLC (method 12) R_t = 2.76 min |
| 41 | 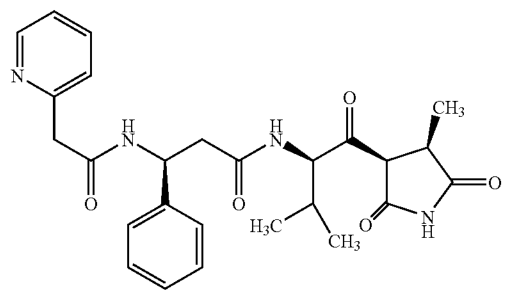 | 478.55 | MS (ES+), m/z (%): 479 (M + H)+ (100) | HPLC (method 5) R_t = 2.64 min |
| 42 | 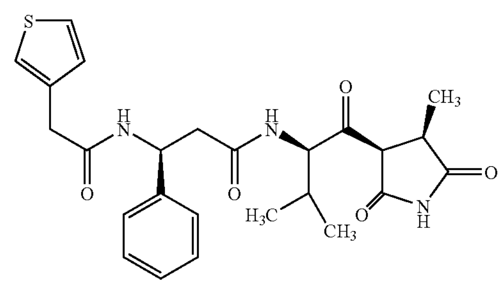 | 483.59 | MS (ES+), m/z (%): 484 (M + H)+ (100) | HPLC (method 15) R_t = 2.94 min |
| 43 | 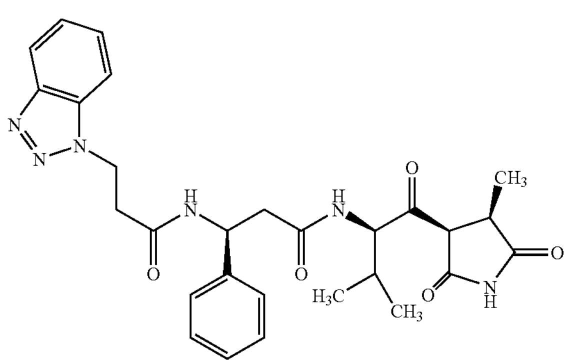 | 532.60 | MS (ES+), m/z (%): 555 (M + Na)+ (100) | HPLC (method 5) R_t = 3.52 min |

-continued

| Example | Structure | MW | MS | HPLC |
|---|---|---|---|---|
| 44 | 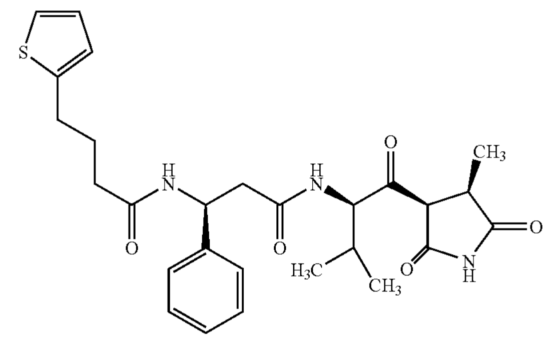 | 511.64 | MS (ES+), m/z (%): 534 (M + Na)+ (100) | HPLC (method 5) R$_t$ = 4.00 min |

General Instructions I: Solid-phase-supported Synthesis

The aldehyde resin (Nova Biochem) (0.78 mmol/g) is suspended in toluene/trimethyl orthoformate (1:1 to 4:1), admixed with the corresponding beta-amino acid methyl ester (2.5-3 eq) at room temperature and shaken overnight. The resin is washed twice with N,N-dimethylformamide, suspended in N,N-dimethylformamide and admixed with tetrabutylammonium borohydride (2-5 eq) at room temperature. After 30 minutes of shaking at room temperature the reaction mixture is slowly admixed with glacial acetic acid (100 eq) at from 40° C. to room temperature, optionally warmed to room temperature again and shaken for at least 1 h. The resin is washed repeatedly with water, methanol, dichloromethane/10% N,N-diisopropylethylamine, methanol, dichloromethane and diethyl ether and dried. The resin is suspended in dichloromethane and shaken with N,N-diisopropylethylamine (10-20 eq) and with the corresponding carbonyl chloride (5 eq) at room temperature for 1-2 h. The resin is washed repeatedly with methanol, N,N-dimethylformamide, methanol, dichloromethane and diethyl ether and dried. For hydrolysis the resin is admixed with a solution of potassium hydroxide (30 eq) in methanol/dioxane (1:2, 30 mg potassium hydroxide/ml solution) and shaken at RT for 3 h. Subsequently the resin is washed with water, methanol, dichloromethane/glacial acetic acid, dichloromethane, dichloromethane/N,N-diisopropylethylamine, methanol, N,N-dimethylformamide, methanol, dichloromethane and diethyl ether. The resin is shaken with (benzotriazol-1-yloxy)bisdimethylaminomethylium fluoroborate (5 eq) and N,N-diisopropylethylamine (20 eq) in N,N-dimethylacetamide at RT for 1 h, washed twice with N,N-dimethylacetamide, admixed with a freshly prepared solution of (3R,4S)-3-[(2S)-2-amino-3-methylbutanoyl]-4-methyl-2,5-pyrrolidinedione hydrochloride (1.5-2 eq) and N,N-diisopropylethylamine (20 eq) and shaken at RT for 3 h. Finally the resin is washed repeatedly with methanol, N,N-dimethylformamide, water, N,N-dimethylformamide, methanol, dichloromethane and diethyl ether and dried. The resin is shaken with trifluoroacetic acid or 50% strength trifluoroacetic acid in dichloromethane at from RT to 50° C. for from 30 minutes to 3 h. The crude product solution is filtered, evaporated to dryness and purifed by reversed phase HPLC using a water/acetonitrile gradient. An alternative possibility is chromatography on silica gel (mobile phases: mixtures of dichloromethane and methanol).

Example 45

N-{1-(3-Chlorophenyl)-3-[((1S)-2-methyl-1-{[(3R,4S)$_4$-methyl-2,5-dioxo-3-pyrrolidinyl]carbonyl}propyl)amino]-3-oxopropyl}-2-pyridinecarboxamide

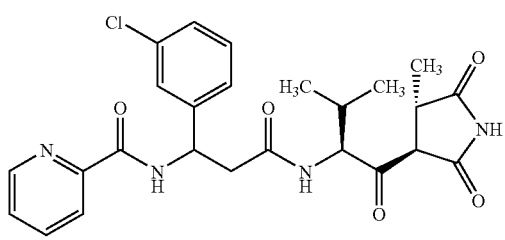

[1] H-NMR (2 diastereoisomers, ratio 1:1, 300 MHz, DMSO-d$_6$): δ=11.3 (d, 1 H), 9.64 (d, 0.5 H), 9.45 (d, 0.5 H), 8.70-8.62 (m, 1 H), 8.28 (d, 0.5H), 8.18 (d, 0.5H), 8.02-7.94 (m, 2 H), 7.65-7.56 (m, 1 H), 7.50-7.41 (m, 1 H), 7.38-7.21 (m, 3 H), 5.48-5.32 (m, 1 H), 4.69 (dd, 0.5H), 4.60 (dd, 0.5H), 4.02 (d, 0.5H), 3.93 (d, 0.5H), 3.10-2.60 (m, 3 H), 2.35-2.15 (m, 1 H), 1.15-1.03 (m, 3 H), 0.75-0.54 (m, 6 H).
MS (ES+): m/z (%)=499 (M+H)+ (100).
HPLC (method 6): R$_t$=3.95 min.

Example 46

N-[(1S)-3-({(1S)-1-Cyclopentyl-2-[(3R,4S)-4-methyl-2,5-dioxo-3-pyrrolidinyl]-2-oxoethyl}amino)-3-oxo-1-phenylpropyl]-4-phenyl-2-pyridinecarboxamide

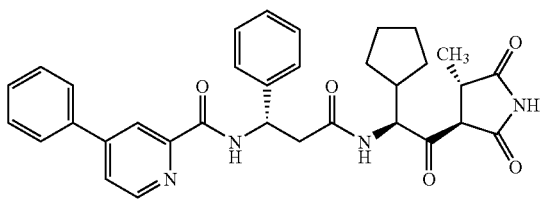

[1] H-NMR (300 MHz, d$_6$-DMSO): δ=11.33 (s, 1 H), 9.59 (d, 1 H), 8.74 (d, 1 H), 8.31 (d, 1 H), 8.23 (s, 1 H), 7.98-7.89

(m, 1 H), 7.87-7.77 (m, 2H), 7.59-7.19 (m, 8 H), 5.50-5.38 (m, 1 H), 4.62 (t, 1 H), 3.99 (d, 1 H), 3.48-3.00 (m, 2 H), 2.96-2.83 (m, 1 H), 2.75-2.18 (m, 4 H), 1.53-0.71 (m, 5 H), 1.08 (d, 3 H).

MS (ES+): m/z=567 (M+H⁺).

HPLC (method 19): R$_t$=4.28 min.

Example 47

N-[(1S)-3-({(1S)-1-Cyclopentyl-2-[(3R,4S)-4-methyl-2,5-dioxo-3-pyrrolidinyl]-2-oxoethyl}amino)-3-oxo-1-phenylpropyl]-3-quinolinecarboxamide

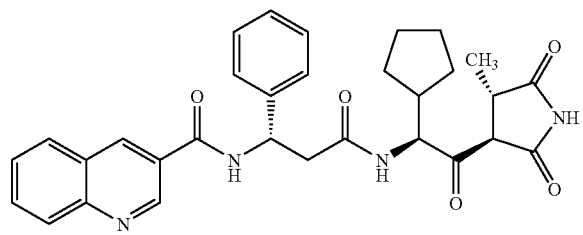

¹H-NMR (300 MHz, d$_6$-DMSO): δ=11.34 (s, 1 H), 9.32 (d, 1 H), 9.22 (d, 1 H), 8.93 (d, 1 H), 8.32 (d, 1 H), 8.11 (d, 2H), 7.89 (dt, 1H), 7.72 (t, 1H), 7.50-7.19 (m, 5 H), 5.58-5.44 (m, 1 H), 4.61 (t, 1 H), 3.93 (d, 1 H), 3.77-3.55 (m, 1 H), 3.10-2.21 (m, 5 H), 1.60-0.96 (m, 6 H), 1.09 (d, 3 H).

MS (ESI+): m/z=541 (M+H⁺).

HPLC (method 19): R$_t$=4.04 min.

Example 48

N-[(1S)-3-({(1S)-1-Cyclopentyl-2-[(3R,4S)-4-methyl-2,5-dioxo-3-pyrrolidinyl]-2-oxoethyl}amino)-3-oxo-1-phenylpropyl]-5-fluoro-1H-indole-2-carboxamide

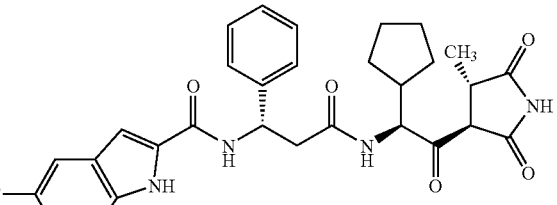

¹H-NMR (200 MHz, d$_6$-DMSO): δ=11.66 (s, 1 H), 11.37 (s, 1 H), 8.83 (d, 1H), 8.27 (d, 1 H), 7.48-6.94 (m, 9 H) 5.54-5.36 (m, 1 H), 4.71-4.61 (m, 1 H), 3.98 (d, 1 H), 3.28-3.19 (m, 1 H), 3.01-2.11 (m, 6 H), 1.54-0.97 (m, 5 H), 1.08 (d, 3 H).

MS (ESI+): m/z=547 (M+H⁺).

HPLC (method 19): R$_t$=3.44 min.

| Example | Structure | MW | MS | HPLC |
|---|---|---|---|---|
| 49 | 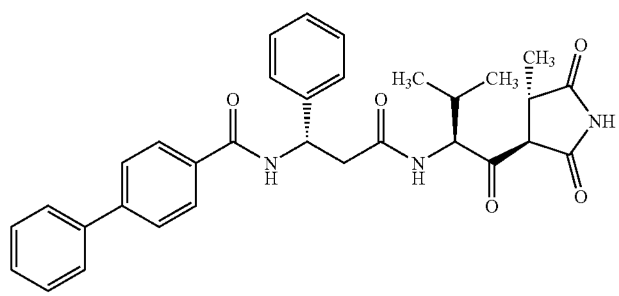 | 539.63 | MS (ES+), m/z: 540 (M + H)⁺ | HPLC (method 5): R$_t$ = 4.22 min |
| 50 | 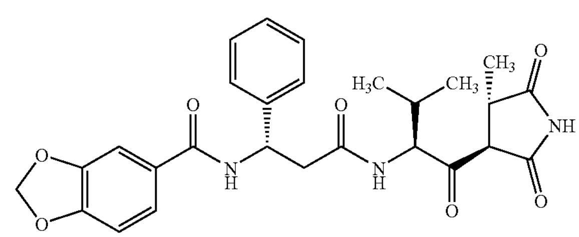 | 507.54 | MS (ES+), m/z: 508 (M + H)⁺ | HPLC (method 5): R$_t$ = 3.61 min |
| 51 | 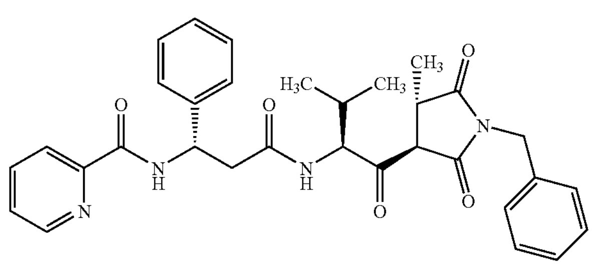 | 554.64 | MS (ES+), m/z: 555 (M + H)⁺ | HPLC (method 8): R$_t$ = 2.72 min |

-continued

| Example | Structure | MW | MS | HPLC |
|---|---|---|---|---|
| 52 | 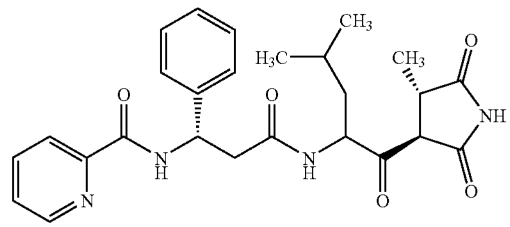 | 478.55 | MS (ES+), m/z: 479 (M + H)+ | HPLC (method 5): $R_t$ = 3.67 min |
| 53 | 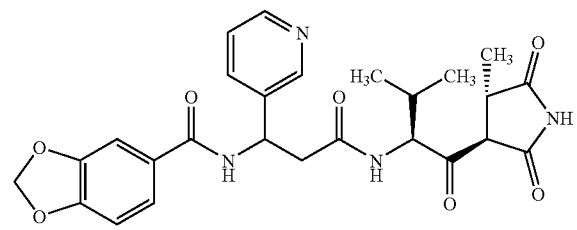 | 508.53 | MS (ES+), m/z: 509 (M + H)+ | HPLC (method 5): $R_t$ = 2.45 and 2.52 min |
| 54 | 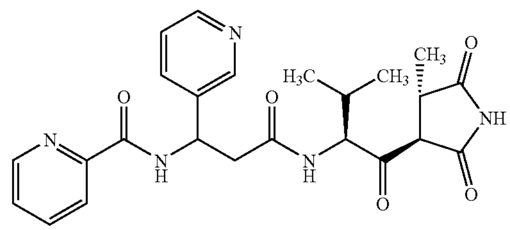 | 465.51 | MS (ES+), m/z: 466 (M + H)+ | |
| 55 | 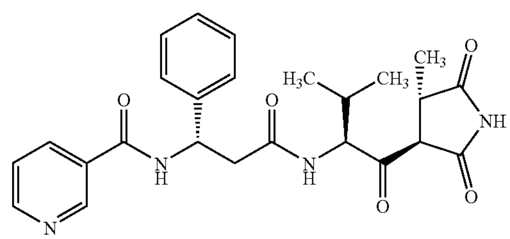 | 464.52 | MS (ES+), m/z: 465 (M + H)+ | HPLC (method 5): $R_t$ = 3.02 min |
| 56 | 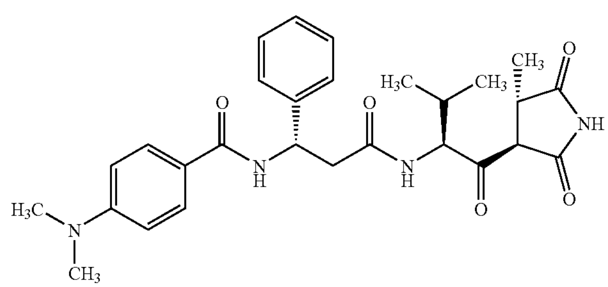 | 506.60 | MS (ES+), m/z: 507 (M + H)+ | HPLC (method 5): $R_t$ = 3.72 min |
| 57 | 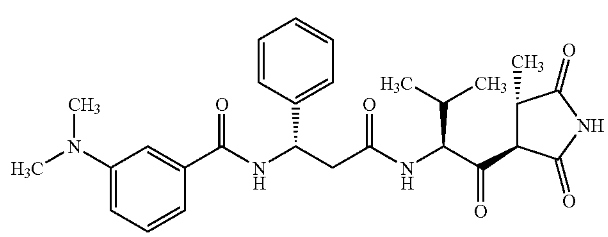 | 506.60 | MS (ES+), m/z: 507 (M + H)+ | HPLC (method 5): $R_t$ = 3.62 min |

-continued

| Example | Structure | MW | MS | HPLC |
|---|---|---|---|---|
| 58 | 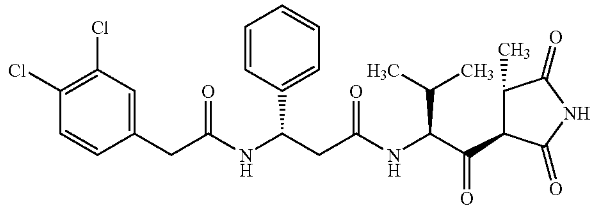 | 546.45 | MS (ES+), m/z: 546 (M + H)+ | HPLC (method 8): R$_t$ = 2.60 min |
| 59 | 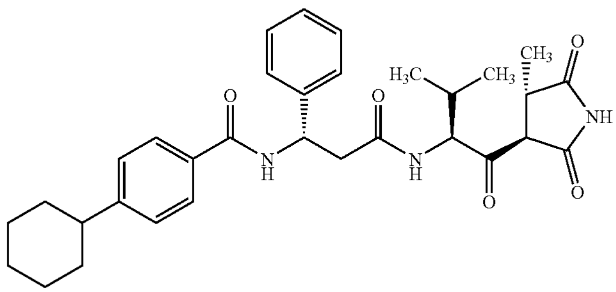 | 545.68 | MS (ES+), m/z: 546 (M + H)+ | HPLC (method 5): R$_t$ = 4.65 min |
| 60 | 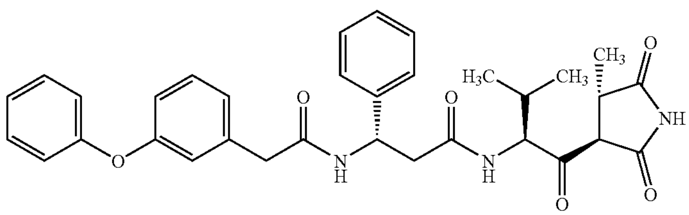 | 569.65 | MS (ES+), m/z: 570 (M + H)+ | HPLC (method 5): R$_t$ = 4.19 min |
| 61 | 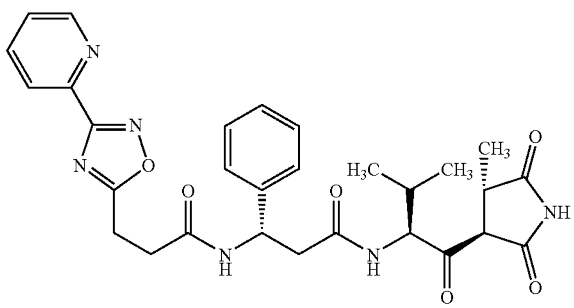 | 560.61 | MS (ES+), m/z: 561 (M + H)+ | HPLC (method 5): R$_t$ = 3.28 min |
| 62 | 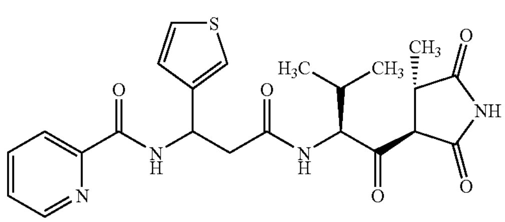 | 470.55 | MS (ES+), m/z: 471 (M + H)+ | HPLC (method 5): R$_t$ = 3.5 min |
| 63 | 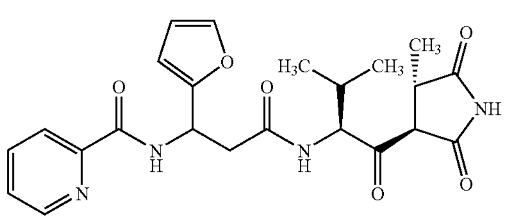 | 454.48 | MS (ES+), m/z: 455 (M + H)+ | HPLC (method 5): R$_t$ = 3.4 min |

-continued

| Example | Structure | MW | MS | HPLC |
|---|---|---|---|---|
| 64 | 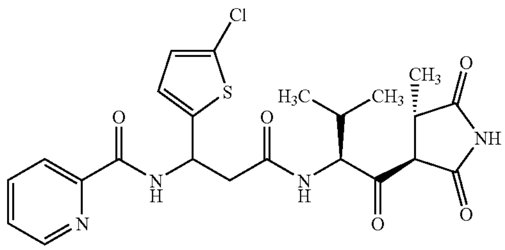 | 504.99 | MS (ES+), m/z: 505 (M + H)+ | HPLC (method 5): R$_t$ = 3.8 min |
| 65 | 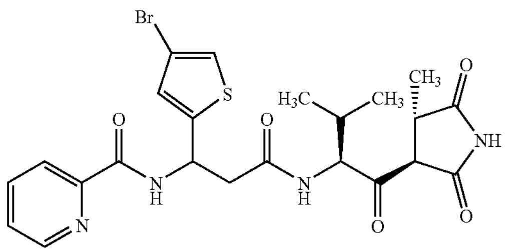 | 549.44 | MS (ES+), m/z: 551 (M + H)+ | HPLC (method 5): R$_t$ = 3.8 min |
| 66 | 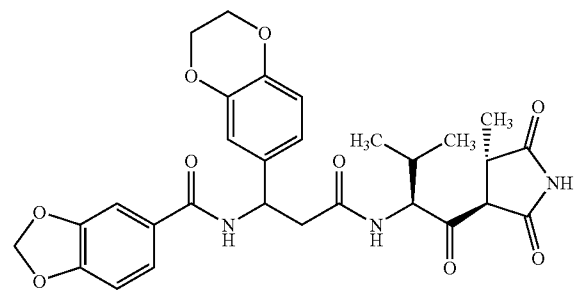 | 565.58 | MS (ES+), m/z: 566 (M + H)+ | HPLC (method 5): R$_t$ = 3.5 min |
| 67 | 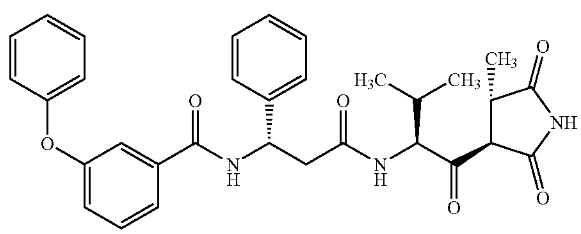 | 555.63 | MS (ES−), m/z: 554 (M − H)− | HPLC (method 6): R$_t$ = 4.28 min |
| 68 | 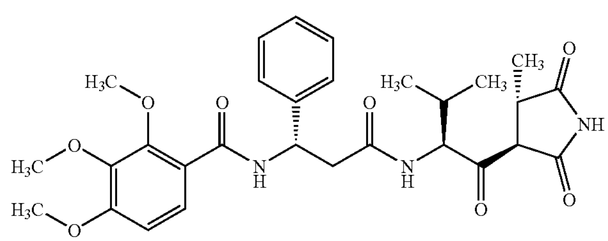 | 553.61 | MS (ES+), m/z: 554 (M + H)+ | HPLC (method 6): R$_t$ = 3.85 min |
| 69 | 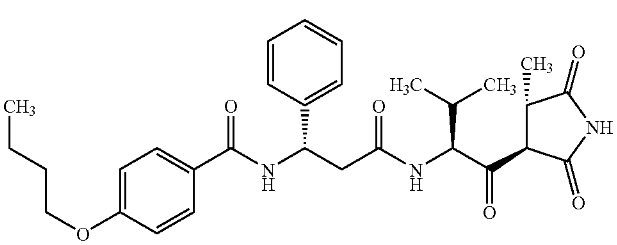 | 535.64 | MS (ES+), m/z: 536 (M + H)+ | HPLC (method 6): R$_t$ = 4.34 min |

-continued

| Example | Structure | MW | MS | HPLC |
|---|---|---|---|---|
| 70 | 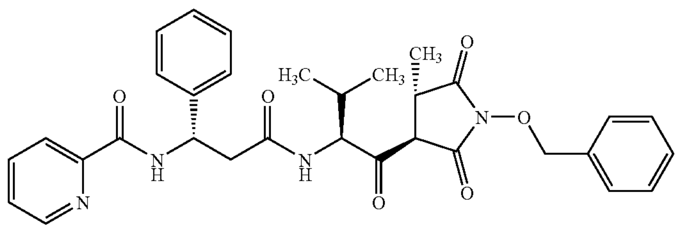 | 570.64 | MS (ES+), m/z: 571 (M + H)+ | HPLC (method 5): R_t = 4.48 min |
| 71 | 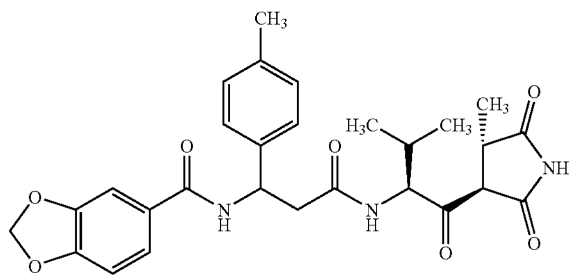 | 521.57 | MS (ES+), m/z: 522 (M + H)+ | HPLC (method 9): R_t = 4.05 min |
| 72 | 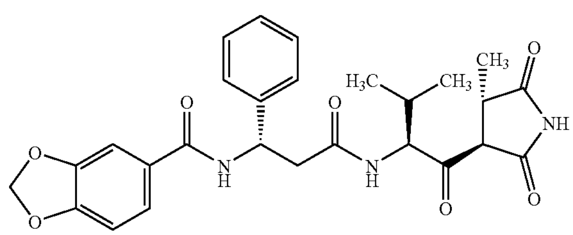 | 521.57 | MS (ES+), m/z: 522 (M + H)+ | HPLC (method 5): R_t = 3.73 min |
| 73 | 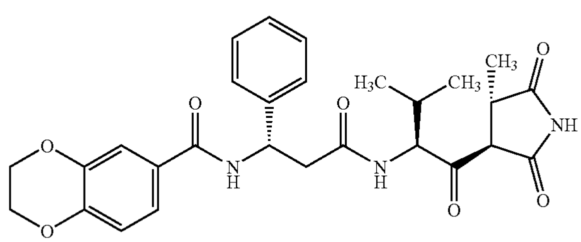 | 535.59 | MS (ES−), m/z: 534 (M − H)− | HPLC (method 5): R_t = 3.71 min |
| 74 | 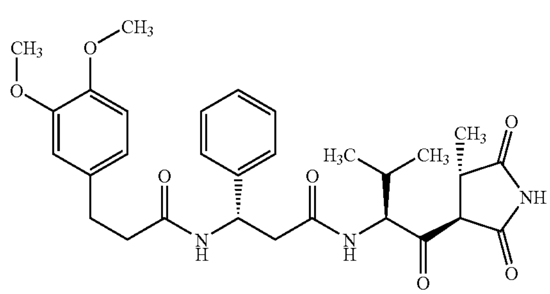 | 551.64 | MS (ES−), m/z: 550 (M − H)− | HPLC (method 5): R_t = 3.65 min |
| 75 | 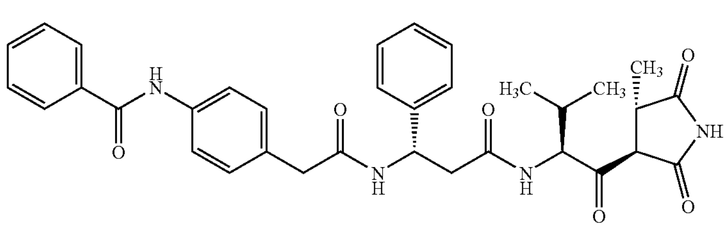 | 596.68 | MS (ES+), m/z: 597 (M + H)+ | HPLC (method 6): R_t = 3.78 min |

-continued

| Example | Structure | MW | MS | HPLC |
|---|---|---|---|---|
| 76 | 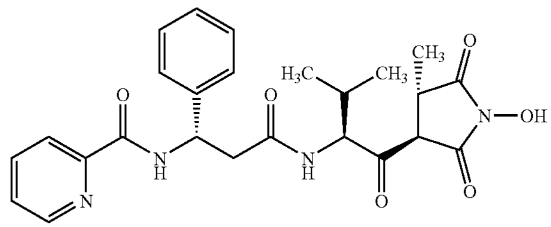 | 480.52 | MS (ES+), m/z: 481 (M + H)$^+$ | HPLC (method 5): R$_t$ = 3.63 min |
| 77 | 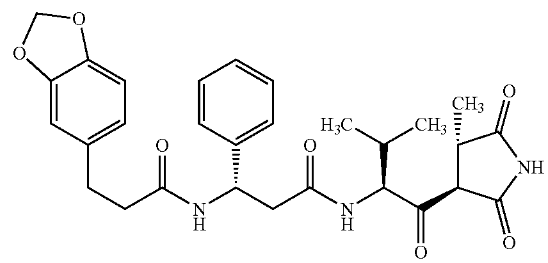 | 535.59 | MS (ES+), m/z: 536 (M + H)$^+$ | HPLC (method 6): R$_t$ = 3.76 min |
| 78 | 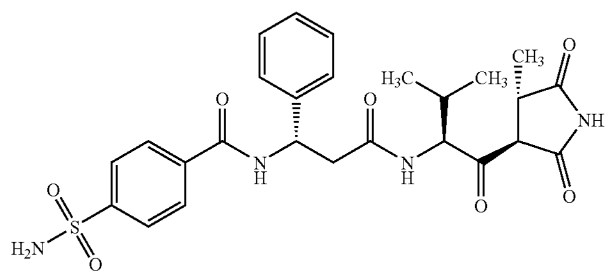 | 542.61 | MS (ES−), m/z: 541 (M − H)$^−$ | HPLC (method 5): R$_t$ = 3.39 min |
| 79 | 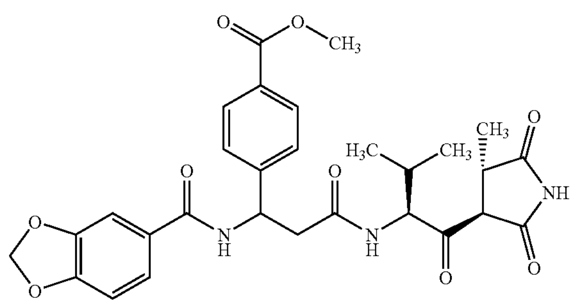 | 565.58 | MS (ES+), m/z: 566 (M + H)$^+$ | HPLC (method 14): R$_t$ = 4.19 min |
| 80 | 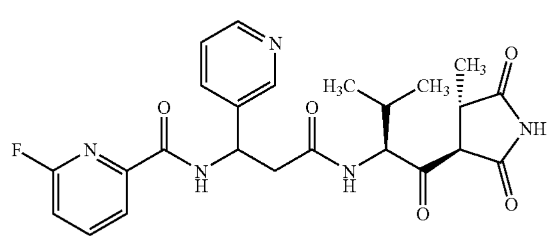 | 483.50 | MS (ES+), m/z: 484 (M + H)$^+$ | HPLC (method 9): R$_t$ = 2.93 min |
| 81 | 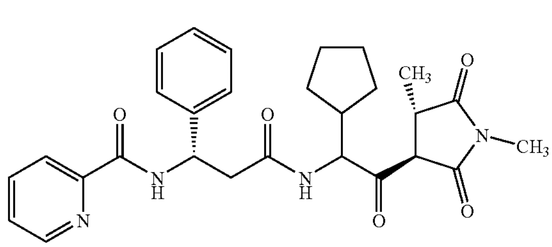 | 504.58 | MS (ES+), m/z: 505 (M + H)$^+$ | HPLC (method 17): R$_t$ = 3.57 min |

-continued

| Example | Structure | MW | MS | HPLC |
|---|---|---|---|---|
| 82 | 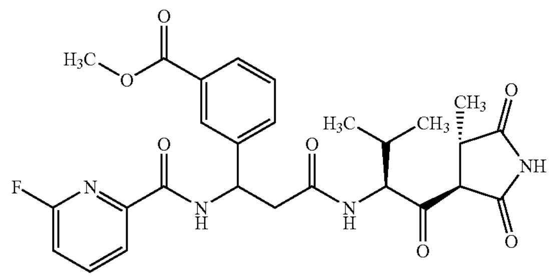 | 540.55 | MS (ES+), m/z: 563 (M + Na)+ | HPLC (method 14): $R_t$ = 4.25 min |
| 83 | 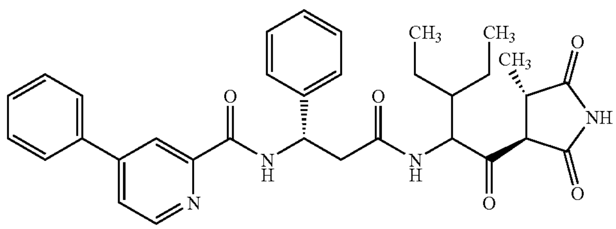 | 568.67 | MS (ES+), m/z: 570 (M + H)+ | HPLC (method 18): $R_t$ = 3.96 min |
| 84 | 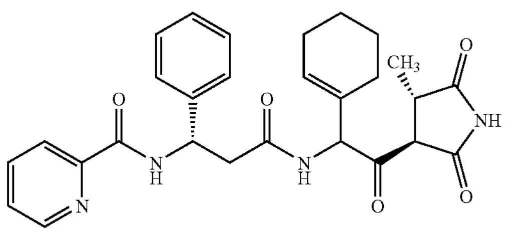 | 502.57 | MS (ES+), m/z: 503 (M + H)+ | HPLC (method 20): $R_t$ = 3.45 min |
| 85 | 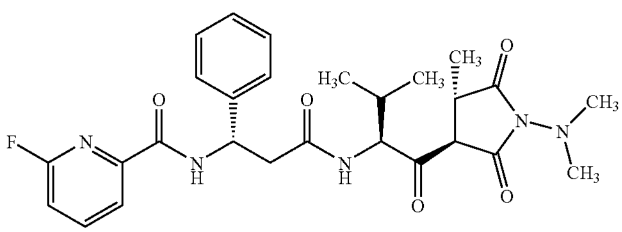 | 525.58 | MS (ES+), m/z: 526 (M + H)+ | HPLC (method 20): $R_t$ = 3.55 min |
| 86 | 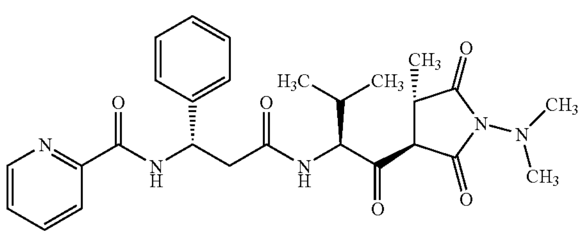 | 507.59 | MS (ES+), m/z: 508 (M + H)+ | HPLC (method 20): $R_t$ = 3.43 min |
| 87 | 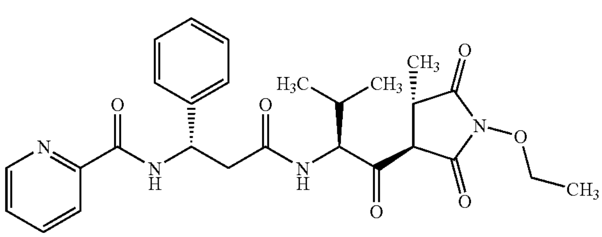 | 508.57 | MS (ES+), m/z: 509 (M + H)+ | HPLC (method 20): $R_t$ = 3.60 min |

| Example | Structure | MW | MS | HPLC |
|---|---|---|---|---|
| 88 | 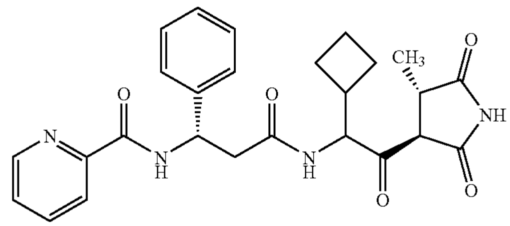 | 476.53 | MS (ES+), m/z: 477 (M + H)+ | HPLC (method 20): R<sub>t</sub> = 3.12 min |
| 89 | 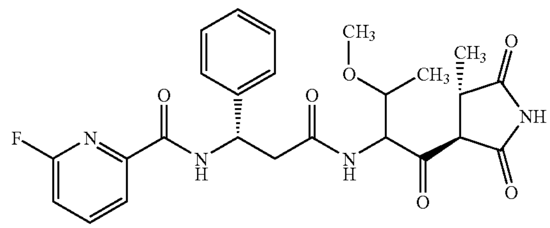 | 498.51 | MS (ES+), m/z: 499 (M + H)+ | HPLC (method 18): R<sub>t</sub> = 3.35 min |
| 90 | 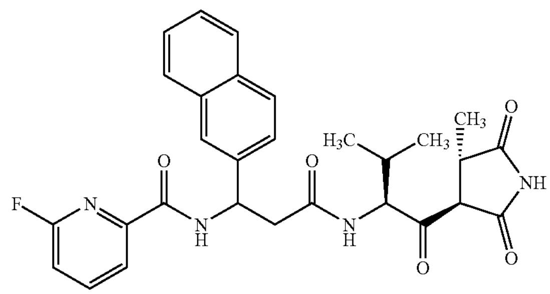 | 532.57 | MS (ES+), m/z: 533 (M + H)+ | HPLC (method 19): R<sub>t</sub> = 4.24 min |
| 91 | 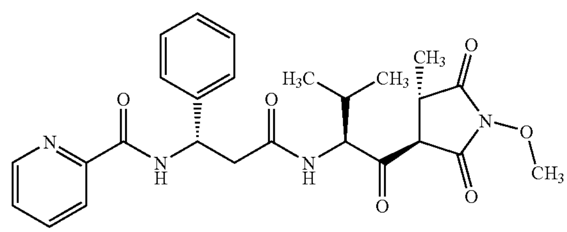 | 494.55 | MS (ES+), m/z: 495 (M + H)+ | HPLC (method 19): R<sub>t</sub> = 3.47 min |
| 92 | 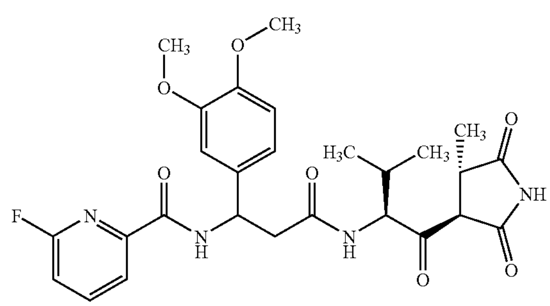 | 542.56 | MS (ES+), m/z: 543 (M + H)+ | HPLC (method 20): R<sub>t</sub> = 3.02 min |
| 93 | 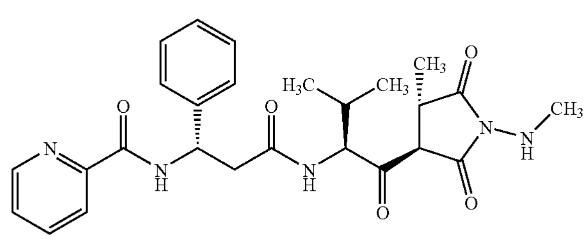 | 493.56 | MS (ES+), m/z: 494 (M + H)+ | HPLC (method 19): R<sub>t</sub> = 4.06 min |

-continued

| Example | Structure | MW | MS | HPLC |
|---|---|---|---|---|
| 94 | 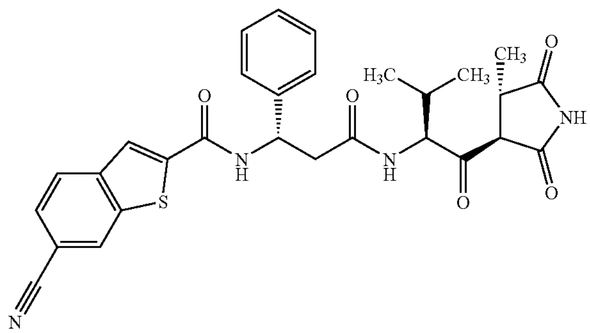 | 544.63 | MS (ES+), m/z: 545 (M + H)+ | HPLC (method 20): R$_t$ = 3.42 min |
| 95 | 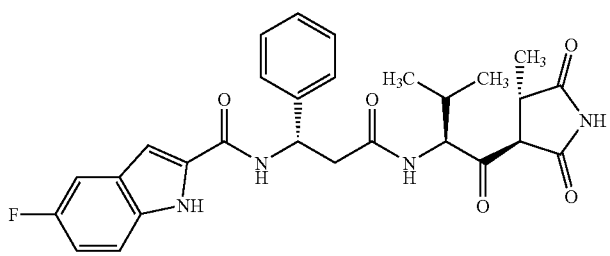 | 520.56 | MS (ES+), m/z: 521 (M + H)+ | HPLC (method 19): R$_t$ = 4.17 min |
| 96 | 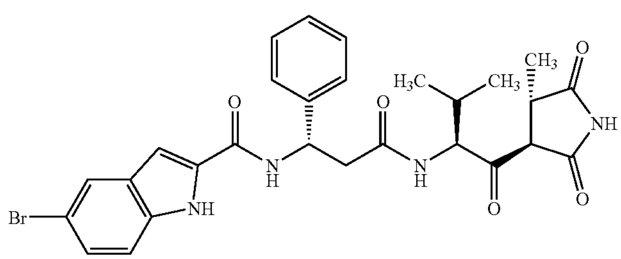 | 581.46 | MS (ES+), m/z: 583 (M + H)+ | HPLC (method 18): R$_t$ = 3.6 min |
| 97 | 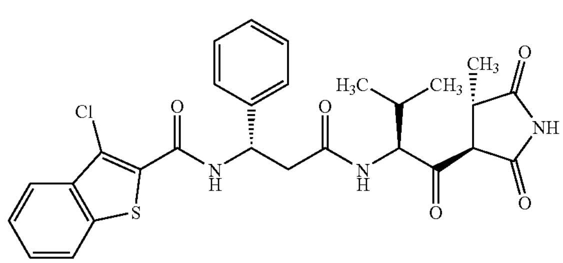 | 554.06 | MS (ES+), m/z: 554 (M + H)+ | HPLC (method 19): R$_t$ = 4.17 min |
| 98 | 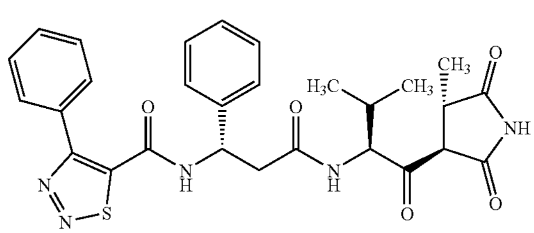 | 547.63 | MS (ES+), m/z: 548 (M + H)+ | HPLC (method 19): R$_t$ = 4.01 min |

-continued

| Example | Structure | MW | MS | HPLC |
|---|---|---|---|---|
| 99 | 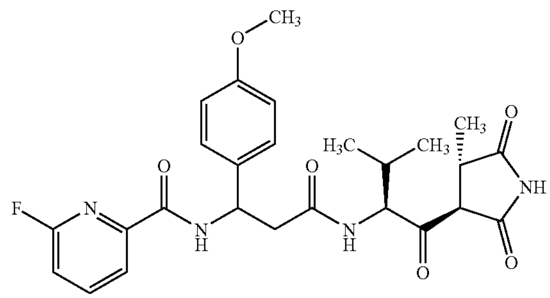 | 512.54 | MS (ES+), m/z: 513 (M + H)+ | HPLC (method 19): R$_t$ = 4.04 min |
| 100 | 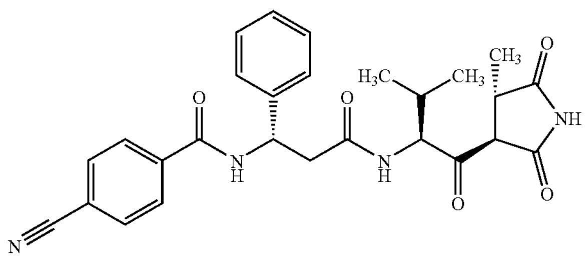 | 488.54 | MS (ES+), m/z: 489 (M + H)+ | HPLC (method 20): R$_t$ = 3.15 min |
| 101 | 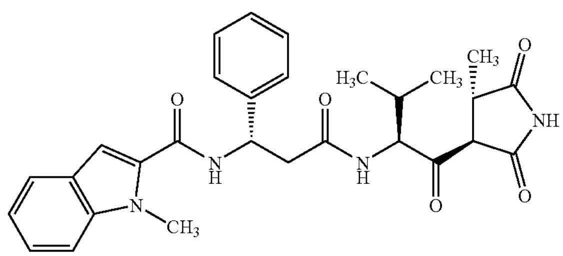 | 516.60 | MS (ES+), m/z: 517 (M + H)+ | HPLC (method 18): R$_t$ = 3.5 min |
| 102 | 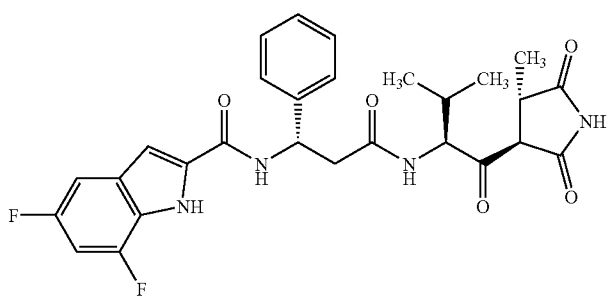 | 538.55 | MS (ES+), m/z: 539 (M + H)+ | HPLC (method 18): R$_t$ = 3.5 min |
| 103 | 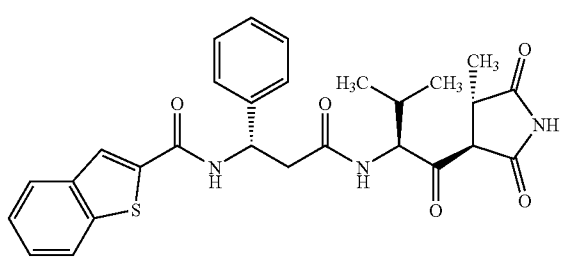 | 519.62 | MS (ES+), m/z: 520 (M + H)+ | HPLC (method 18): R$_t$ = 3.5 min |

-continued

| Example | Structure | MW | MS | HPLC |
|---|---|---|---|---|
| 104 | 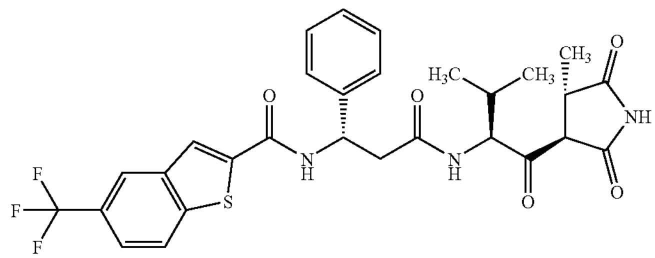 | 587.62 | MS (ES+), m/z: 588 (M + H)+ | HPLC (method 18): R$_t$ = 3.7 min |
| 105 | 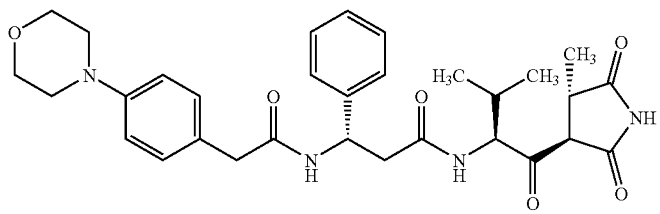 | 562.66 | MS (ES+), m/z: 563 (M + H)+ | HPLC (method 19): R$_t$ = 2.42 min |
| 106 | 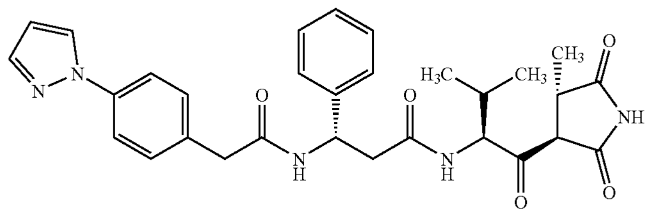 | 543.62 | MS (ES+), m/z: 544 (M + H)+ | HPLC (method 18): R$_t$ = 3.2 min |
| 107 | 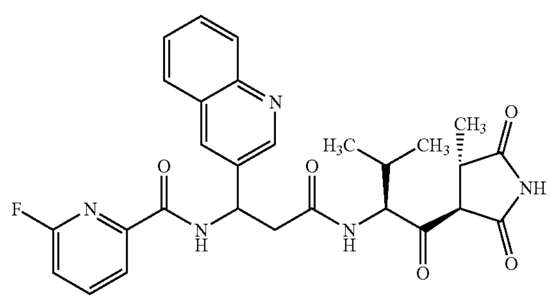 | 533.56 | MS (ES+), m/z: 534 (M + H)+ | HPLC (method 20): R$_t$ = 2.45 min |
| 108 | 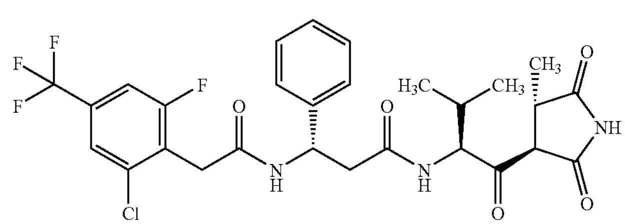 | 597.99 | MS (ES+), m/z: 598 (M + H)+ | HPLC (method 18): R$_t$ = 3.6 min |
| 109 | 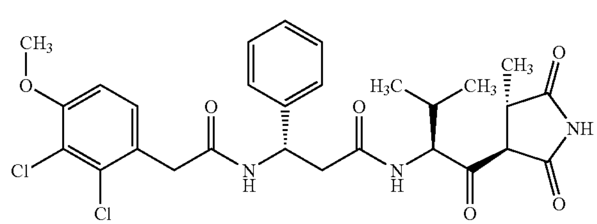 | 576.47 | MS (ES+), m/z: 576 (M + H)+ | HPLC (method 18): R$_t$ = 3.5 min |

-continued

| Example | Structure | MW | MS | HPLC |
|---|---|---|---|---|
| 110 | 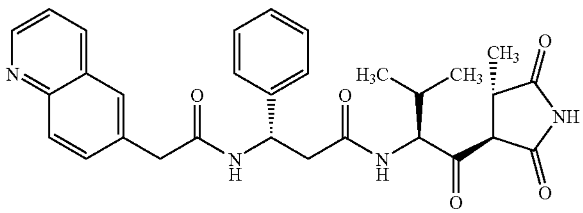 | 528.61 | MS (ES+), m/z: 529 (M + H)+ | HPLC (method 18): R_t = 2.6 min |
| 111 | 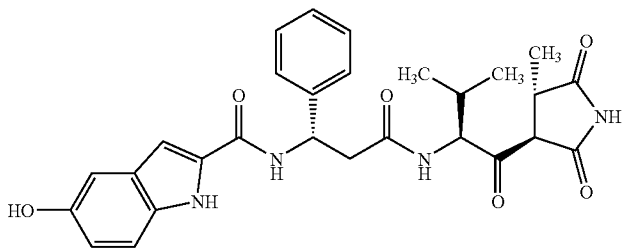 | 518.57 | MS (ES+), m/z: 519 (M + H)+ | HPLC (method 19): R_t = 2.26 min |
| 112 | 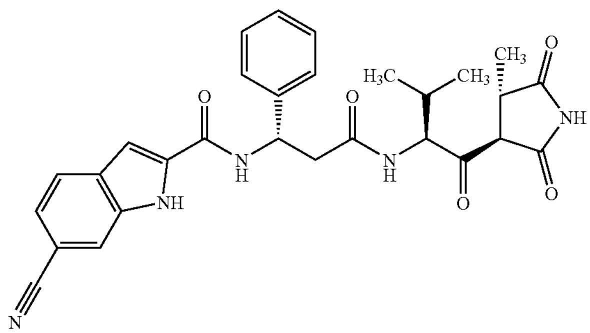 | 527.58 | MS (ES+), m/z: 528 (M + H)+ | HPLC (method 19): R_t = 2.61 min |
| 113 | 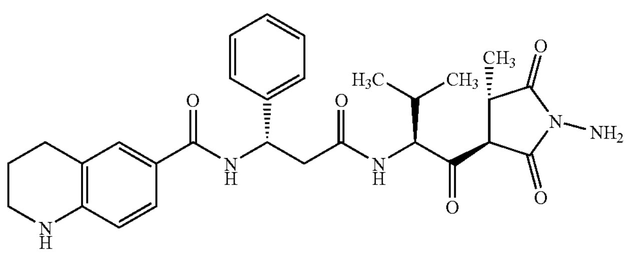 | 533.63 | MS (ES+), m/z: 534 (M + H)+ | HPLC (method 19): R_t = 2.55 min |
| 114 | 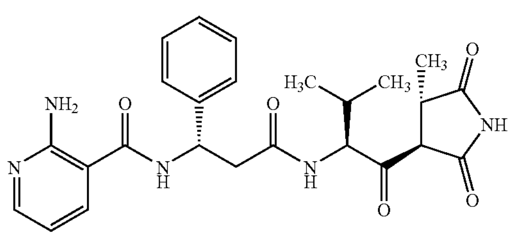 | 479.53 | MS (ES+), m/z: 480 (M + H)+ | HPLC (method 20): R_t = 1.97 min |
| 115 | 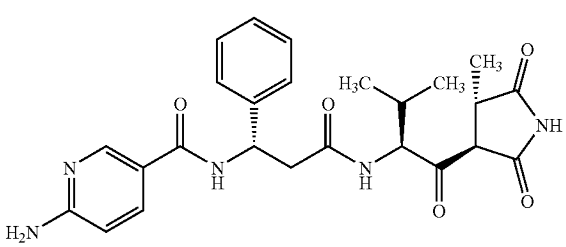 | 479.53 | MS (ES+), m/z: 480 (M + H)+ | HPLC (method 19): R_t = 1.82 min |

B) Evaluation of Physiological Activity

The suitability of the compounds of the invention for treating bacterial diseases can be demonstrated in the following animal models:

Determination of the Minimum Inhibitory Concentration (MIC):

The MIC is determined in a liquid dilution test. Overnight cultures of the test organisms are diluted to a cell count of $10^5$ organisms per ml in Isosensitest medium (Difco, Irvine, USA) and are incubated with dilutions of the test substances (1:2 dilution stages). Exceptions are the tests with *S. pneumoniae* G9A, which are conducted in BHI broth (Difco) plus 20% bovine serum, and with *H. influenzae*, which are conducted in BHI broth (Difco) plus 20% bovine serum, 10 μg/ml hemin and 1% Isovitale (Becton Dickinson, New Jersey, USA).

The cultures are incubated at 37° C. for 18-24 hours; *S. pneumoniae* and *H. influenzae* in the presence of 8-10% $CO_2$.

Results:

The lowest concentration of each substance at which there is no longer any visible bacterial growth is defined as the MIC. The MICs in μmol/l of some compounds of the invention against a series of test organisms are listed by way of example in the table below.

| Ex. No. | *Staphylococcus aureus* 133 | *Haemophilus influenzae* Spain 7 |
|---|---|---|
| 2 | 15.63 | 7.81 |
| 4 | 15.63 | 31.25 |
| 6 | 7.81 | 15.63 |
| 9 | 7.81 | 62.5 |
| 48 | 0.98 | 15.63 |
| 109 | 0.98 | 62.5 |

Systemic Infection with *S. aureus* 133

*S. aureus* 133 cells are cultured overnight in BH broth (Oxoid, N.Y., USA). The overnight culture is diluted 1:100 in fresh BH broth and spun at high speed for 3 hours. The bacteria in the logarithmic growth phase are centrifuged off and washed 2× with buffered physiological saline solution. Subsequently a photometer (Dr. Lange model LP 2W, Berlin, Germany) is used to establish a cell suspension in saline solution with an extinction of 50 units. Following a dilution step (1:15) this suspension is mixed 1:1 with a 10% mucin suspension. 0.25 ml/20 g mouse of this infection solution is administered intraperitoneally. This corresponds to a cell count of approximately $1 \times 10E^6$ organisms/mouse. The intraperitoneal or intravenous therapy is practiced 30 minutes following infection. Female CFW1 mice are used for the infection experiment. The survival of the animals is recorded over 6 days.

C) Examples of Pharmaceutical Compositions

The substances of the invention can be converted into pharmaceutical formulations as follows:

Tablet:

Composition:

100 mg of the compound from Example 1, 50 mg of lactose (monohydrate), 50 mg of corn starch, 10 mg of polyvinylpyrolidone (PVP 25) (BASF, Germany) and 2 mg of magnesium stearate.

Tablet weight 212 mg. Diameter 8 mm, radius of curvature 12 mm.

Production:

The mixture of the compound of Example 1, lactose and starch is granulated with a 5% strength solution (m/m) of the PVP in water. The granules are dried and then mixed with the magnesium stearate for 5 minutes. This mixture is compressed using a conventional tablet press (see above for tablet format).

Oral Suspension:

Composition:

1000 mg of the compound from Example 1, 1000 mg of ethanol (96%), 400 mg of Rhodigel (xanthan gum) (FMC, USA) and 99 g of water.

10 ml of oral suspension correspond to a single dose of 100 mg of the compound of the invention.

Production:

The Rhodigel is suspended in ethanol and the compound of Example 1 is added to the suspension. The water is added with stirring. The mixture is stirred for about 6 h until the Rhodigel has finished swelling.

Solution for Intravenous Administration:

Composition:

100-200 mg of the compound from Example 1, 15 g of polyethylene glycol 400 and 250 g of injection-grade water.

Production:

The compound of Example 1 is dissolved together with polyethylene glycol 400 in the water, with stirring. The solution is subjected to sterile filtration (pore diameter 0.22 μm) and dispensed under aseptic conditions into heat-sterilized infusion bottles. These bottles are sealed with infusion stoppers and crimped caps.

The invention claimed is:

1. A compound of the formula

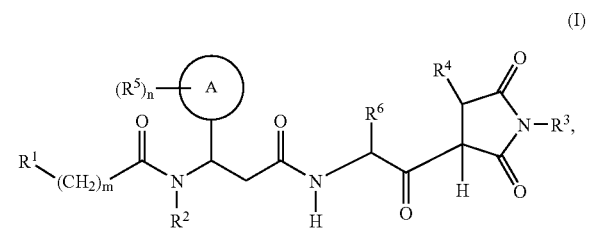

in which

R¹ is heteroaryl,
where heteroaryl can be substituted by 0, 1, 2 or 3 substituents R¹⁻¹, the substituents R¹⁻¹ being selected independently of one another from the group consisting of halogen, alkyl, nitro, amino, alkylamino, cyano, trifluoromethyl, cycloalkyl, heterocyclyl, aryl, heteroaryl, hydroxyl, alkoxy, aryloxy, benzyloxy, carboxyl, alkoxycarbonyl, aminocarbonyl, alkylcarbonylamino, alkylaminocarbonyl and aminosulfonyl, or R¹ is aryl,
where aryl is substituted by 1, 2 or 3 substituents R¹⁻², the substituents R¹⁻² being selected independently of one another from the group consisting of halogen, alkyl, nitro, amino, alkylamino, cyano, trifluoromethyl, cycloalkyl, heterocyclyl, aryl, heteroaryl, hydroxyl, alkoxy, aryloxy, benzyloxy, carboxyl, alkoxycarbonyl, aminocarbonyl, alkylcarbonylamino, arylcarbonylamino, alkylaminocarbonyl and aminosulfonyl,
or
two substituents $R^{1-2}$, together with the carbon atoms to which they are attached, form a cycloalkyl or heterocyclyl which can be substituted by 0, 1 or 2 substituents $R^{1-2-1}$, the substituents $R^{1-2-1}$ being selected independently of one another from the group consisting of halogen, nitro, amino, trifluoromethyl, hydroxyl, alkyl and alkoxy, $R^2$ is hydrogen or methyl, $R^3$ is hydrogen, hydroxyl, amino, $C_1$-$C_3$ alkyl, benzyl, $C_1$-$C_3$ alkoxy, benzyloxy, $C_1$-$C_3$ alkylamino, $C_1$-$C_3$ alkylcarbonylamino, phenylcarbonylamino or benzylcarbonylamino, $R^4$ is hydrogen or $C_1$-$C_3$ alkyl, $R^5$ is halogen, trifluoromethyl, trifluoromethoxy, nitro, amino, alkylamino, hydroxyl, alkyl, alkoxy, carboxyl, alkoxycarbonyl, aminocarbonyl, alkylaminocarbonyl, aryl or heteroaryl,
or
two substituents $R^5$ together with the carbon atoms to which they are attached form a cycloalkyl or heterocyclyl each of which may be substituted by 0, 1 or 2 substituents $R^{5-1}$, the substituents $R^{5-1}$ being selected independently of one another from the group consisting of halogen, nitro, amino, trifluoromethyl, hydroxyl, alkyl and alkoxy, $R^6$ is alkyl, cycloalkyl, cycloalkenyl or heterocyclyl,
it being possible for $R^6$ to be substituted by 0, 1 or 2 substituents $R^{6-1}$, the substituents $R^{6-1}$ being selected independently of one another from the group consisting of halogen, nitro, amino, trifluoromethyl, hydroxyl, alkyl and alkoxy, n is a number 0, 1, 2 or 3,
it being possible for the radicals $R^5$ to be identical or different when n is 2 or 3, m is a number 0, 1, 2, 3 or 4, A is aryl or heteroaryl, or a salt thereof, a solvate thereof or a solvate of a salt thereof.

2. A compound according to claim 1, characterized in that it corresponds to the formula

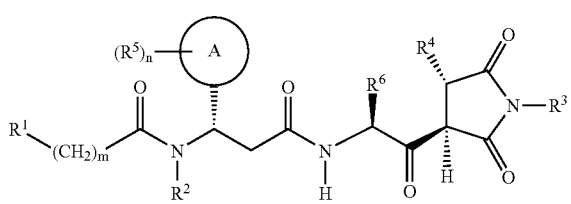

(Ia)

in which $R^1$ to $R^6$, A, m and n have the same definition as in claim 1.

3. A compound according to claim 1, characterized in that $R^1$ is pyridyl, imidazolyl, thienyl, furyl, oxadiazolyl, pyrazolyl, pyrazinyl, pyridazinyl, pyrimidinyl, quinolinyl or isoquinolinyl,
where $R^1$ can be substituted by 0, 1 or 2 substituents $R^{1-1}$, the substituents $R^{1-1}$ being selected independently of one another from the group consisting of halogen, alkyl, amino, trifluoromethyl, phenyl and alkoxy,
or $R^1$ is phenyl or naphthyl,
where phenyl or naphthyl are substituted by 1, 2 or 3 substituents $R^{1-2}$, the substituents $R^{1-2}$ being selected independently of one another from the group consisting of halogen, $C_1$-$C_4$ alkyl, dimethylamino, cyano, trifluoromethyl, 3- to 7-membered cycloalkyl, 5- or 6-membered heterocyclyl, phenyl, 5- or 6-membered heteroaryl, $C_1$-$C_3$ alkoxy, phenyloxy, benzyloxy, phenylcarbonylamino and aminosulfonyl,
or
two substituents $R^{1-2}$, together with the carbon atoms to which they are attached, form a 1,3-benzodioxole or a 1,4-benzodioxane, $R^2$ is hydrogen, $R^3$ is hydrogen, amino, methyl, methoxy, ethoxy, methylamino or dimethylamino, $R^4$ is methyl, $R^5$ is fluoro, chloro, trifluoromethyl, C 1-$C_4$ alkoxy, methoxycarbonyl, $C_1$-$C_4$ alkyl, phenyl or pyridyl,
or
two substituents $R^5$, together with the phenyl ring to which they are attached, form a 1,3-benzodioxole or a 1,4-benzodioxane, $R^6$ is $C_3$-$C_6$ alkyl or 3- to 6-membered cycloalkyl, n is a number 0, 1 or 2,
and, if n is 2, the radicals $R^5$ can be identical or different, m is a number 0, 1, 2 or 3,
and A is phenyl, naphthyl, pyridyl, thienyl, furanyl, quinolinyl or isoquinolinyl.

4. A compound according to claim 1, characterized in that $R^1$ is pyridyl, thienyl, furyl, quinolinyl or isoquinolinyl,
where $R^1$ can be substituted by 0, 1 or 2 substituents $R^{1-1}$, the substituents $R^{1-1}$ being selected independently of one another from the group consisting of halogen, $C_1$-$C_4$ alkyl, trifluoromethyl, phenyl and $C_1$-$C_3$-alkoxy,
or $R^1$ is phenyl or naphthyl,
where phenyl or naphthyl are substituted by 1, 2 or 3 substituents $R^{1-2}$, the substituents $R^{1-2}$ being selected independently of one another from the group consisting of halogen, $C_1$-$C_4$ alkyl, dimethylamino, cyano, trifluoromethyl, 5- or 6-membered heterocyclyl, 5- or 6-membered heteroaryl, $C_1$-$C_3$ alkoxy, phenyloxy or benzyloxy,
or
two substituents $R^{1-2}$, together with the carbon atoms to which they are attached, form a 1,3-benzodioxole or a 1,4-benzodioxane, $R^2$ is hydrogen, $R^3$ is hydrogen, amino, methylamino or dimethylamino, $R^4$ is methyl, $R^5$ is fluoro, chloro, trifluoromethyl, $C_1$-$C_3$ alkoxy, $C_1$-$C_4$ alkyl, phenyl or pyridyl, $R^6$ is isopropyl, tert-butyl, isopentyl, cyclopentyl or cyclohexyl, n is a number 0, 1 or 2,
and, if n is 2, the radicals $R^5$ can be identical or different, m is a number 0, 1 or 2,
and A is phenyl, naphthyl, pyridyl, thienyl, quinolinyl or isoquinolinyl.

5. A compound according to claim 1, characterized in that $R^1$ is pyridyl, thienyl, furyl, quinolinyl or isoquinolinyl, where $R^1$ can be substituted by 0, 1 or 2 substituents $R^{1-1}$, the substituents $R^{1-1}$ being selected independently of one another from the group consisting of fluoro, chloro, trifluoromethyl, $C_1$-$C_4$ alkyl, phenyl and methoxy.

6. A compound according to claim 1, characterized in that $R^1$ is phenyl or naphthyl, where phenyl or naphthyl are substituted by 1, 2 or 3 substituents $R^{1-2}$, the substituents $R^{1-2}$ being selected independently of one another from the group consisting of halogen, $C_1$-$C_4$ alkyl, dimethylamino, cyano, trifluoromethyl, 5- or 6-membered heterocyclyl, 5- or 6-membered heteroaryl, $C_1$-$C_3$ alkoxy, phenyloxy or benzyloxy, or two substituents $R^{1-2}$, together with the carbon atoms to which they are attached, form a 1,3-benzodioxole or a 1,4-benzodioxane.

7. A compound according to claim 1, characterized in that $R^2$ is hydrogen.

8. A compound according to claim 1, characterized in that $R^3$ is hydrogen or amino.

9. A compound according to claim 1, characterized in that $R^4$ is methyl.

10. A compound according to claim 1, characterized in that n is the number zero.

11. A compound according to claim 1, characterized in that n is the number 1, A is phenyl and $R^5$ is fluoro, chloro, trifluoromethyl, alkoxy, $C_1$-$C_4$-alkyl, phenyl or pyridyl, $R^5$ being positioned meta or para to the linkage site of the phenyl ring.

12. A compound according to claim 1, characterized in that $R^6$ is $C_3$-$C_6$-alkyl or 3- to 6-membered cycloalkyl.

13. A compound according to claim 1, characterized in that m is the number zero.

14. A compound according to claim 1, characterized in that A is phenyl, naphthyl, pyridyl, thienyl, quinolinyl or isoquinolinyl.

15. A process for preparing a compound of formula (I) according to claim 1, characterized in that

[A] a compound of the formula

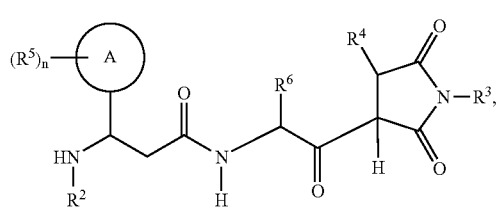

(II)

$R^2$ to $R^6$, A and n are as defined in claim 1, is reacted with a compound of the formula

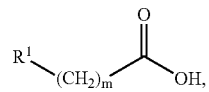

(III)

in which $R^1$ and m are as defined in claim 1, or

[B] a compound of the formula

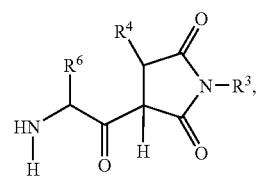

(IV)

in which $R^3$, $R^4$ and $R^6$ are as defined in claim 1, is reacted with a compound of the formula

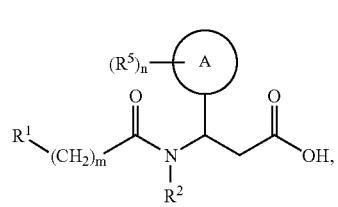

(V)

in which $R^1$, $R^2$, $R^5$, A, m and n are as defined in claim 1.

16. A pharmaceutical composition comprising at least one compound of claim 1 in combination with at least one pharmaceutically acceptable carrier or excipient.

17. A method of controlling bacterial infections in a person or an animal comprising administering to a person or animal, in need thereof, an antibacterially effective amount of at least one compound of claim 1.

18. A method of controlling bacterial infections in a person or an animal comprising administering to a person or animal, in need thereof, an antibacterially effective amount of at least one composition of claim 16.

* * * * *